US012065664B2

(12) United States Patent
Peer et al.

(10) Patent No.: US 12,065,664 B2
(45) Date of Patent: Aug. 20, 2024

(54) METHOD FOR TREATMENT OF A LEUKOCYTE RELATED DISEASE BY DELIVERY OF NUCLEIC ACID MOLECULES TO LEUKOCYTES USING TARGETED LIPID PARTICLES

(71) Applicant: RAMOT AT TEL-AVIV UNIVERSITY LTD., Tel Aviv (IL)

(72) Inventors: Dan Peer, Kiryat Ono (IL); Shiri Weinstein, Tel Aviv (IL); Itai Antoine Toker, Tel Aviv (IL); Srinivas Ramishetti, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 538 days.

(21) Appl. No.: 17/128,736

(22) Filed: Dec. 21, 2020

(65) Prior Publication Data
US 2021/0108228 A1 Apr. 15, 2021

Related U.S. Application Data

(62) Division of application No. 15/571,535, filed as application No. PCT/IL2016/050543 on May 25, 2016, now Pat. No. 10,920,246.

(60) Provisional application No. 62/268,526, filed on Dec. 17, 2015, provisional application No. 62/166,146, filed on May 26, 2015.

(51) Int. Cl.
| | | |
|---|---|---|
| A61K 39/395 | (2006.01) | |
| A61K 9/00 | (2006.01) | |
| A61K 9/51 | (2006.01) | |
| A61K 31/105 | (2006.01) | |
| A61K 31/7105 | (2006.01) | |
| A61K 31/713 | (2006.01) | |
| A61K 47/68 | (2017.01) | |
| A61K 47/69 | (2017.01) | |
| A61K 48/00 | (2006.01) | |
| A61P 35/02 | (2006.01) | |
| C07K 16/28 | (2006.01) | |
| C12N 15/88 | (2006.01) | |

(52) U.S. Cl.
CPC ............ *C12N 15/88* (2013.01); *A61K 9/0019* (2013.01); *A61K 9/513* (2013.01); *A61K 31/105* (2013.01); *A61K 31/7105* (2013.01); *A61K 31/713* (2013.01); *A61K 39/395* (2013.01); *A61K 47/6849* (2017.08); *A61K 47/6911* (2017.08); *A61K 48/0066* (2013.01); *A61P 35/02* (2018.01); *C07K 16/2812* (2013.01); *C07K 16/2896* (2013.01)

(58) Field of Classification Search
None
See application file for complete search history.

(56) References Cited

U.S. PATENT DOCUMENTS

| 10,583,084 B2 | 3/2020 | Peer |
| 2011/0038941 A1 | 2/2011 | Lee |
| 2013/0245107 A1 | 9/2013 | de Fougerolles |
| 2014/0134260 A1 | 5/2014 | Heyes |

FOREIGN PATENT DOCUMENTS

| WO | 2009120247 A2 | 10/2009 |
| WO | 2011154453 A1 | 12/2011 |
| WO | 2013098813 A1 | 7/2013 |

OTHER PUBLICATIONS

Behhke, "Progress towards in vivo use of siRNAs", Molecular therapy: the journal of the American Society of Gene Therapy, pp. 644-670, vol. 13(No. 4) pp. 644-670( Feb. 2006).
Belliveau et al., "Microfluidic Synthesis of Highly Potent Limit-size Lipid Nanoparticles for In Vivo Delivery of siRNA" Molecular therapy. Nucleic acids, pp. 1-9 1:e37 (Aug. 2012).
Buschle et al., "Transfection and gene expression in normal and malignant primary B lymphocytes", Journal of immunological methods, pp. 77-85, vol. 133(No. 1) (Jun. 1990).
Campo & Rule, "Mantle cell lymphoma: evolving management strategies", Blood, pp. 48-55, vol. 125(No. 1) (2015).
Chang et al., "Egress of CD19(+)CD5(+) cells into peripheral blood following treatment with the Bruton tyrosine kinase inhibitor ibrutinib in mantle cell lymphoma patients", pp. 2412-2424, Blood vol. 122(No. 14) (Oct. 2013).
Cheah et al., "Patients with mantle cell lymphoma falling ibrutinib are unlikely to respond to salvage chemotherapy and have poor outcomes" Annals of Oncology, pp. 1175-1179, vol. 26(No. 6), (Feb. 2015).
Chen, Development of lipid nanoparticle formulations of sIRNA for hepatocyte gene silencing following subcutaneous administration:, Journal of Controlled Release, pp. 106-112, vol. 196 (Sep. 2014).
Cohen et al., Localized RNAi therapeutics of chemoresistant grade IV glioma using hyaluronan-grafted lipid-based nanoparticles. ACS nano, pp. 1581-1591, vol. 9(No. 2) (Jan. 2015).
Deckert et al., "SAR650984, a novel humanized CD38-targeting antibody, demonstrates potent antitumor activity in models of multiple myeloma and other CD38+ hematologic malignancies", Clinical cancer research: an official journal of the American Association for Cancer Research, pp. 4574-4583, vol. 20(No. 17) (Jul. 2014).
Dreyling, "Mantle cell lymphoma: biology, clinical presentation, and therapeutic approaches", American Society of Clinical Oncology educational book / ASCO. American Society of Clinical Oncology. Meeting, pp. 191-198 (2014).

(Continued)

*Primary Examiner* — Yunsoo Kim
(74) *Attorney, Agent, or Firm* — BROWDY AND NEIMARK, PLLC

(57) ABSTRACT

Disclosed are targeted lipid based particles for delivery of nucleic acid molecules (such as siRNA) to leukocytes (such as T-Cells and B-cells). Further disclosed are uses of the targeted lipid based particles for treating Leukocytes-associated diseases, such as, cancer.

15 Claims, 19 Drawing Sheets

Specification includes a Sequence Listing.

(56) References Cited

OTHER PUBLICATIONS

Freeley & Long, "Advances in siRNA delivery to T-cells: potential clinical applications for inflammatory disease, cancer and infection", Biochemical Journal, pp. 133-147, vol. 455(No. 2), (2013).
Gilleron et al., "Image-based analysis of lipid nanoparticle-mediated siRNA delivery, intracellular trafficking and endosomal escape" Nature biotechnology, pp. 638-646, vol. 31(No. 7), (Jun. 2013).
Goffinet & Keppler, "Efficient nonviral gene delivery into primary lymphocytes from rats and mice", The FASEB journal, pp. 500-502, vol. 20(No. 3), (Apr. 2006).
Gust et al., "Correction: RNA interference-mediated gene silencing in murine T cells: in vitro and in vivo validation of proinflammatory target genes", Cell Communication and Signaling, pp. 1-8, vol. 6, No. 3 (Aug. 2008).
He et al., "Discovery of siRNA lipid nanoparticles to transfect suspension leukemia cells and provide in vivo delivery capability", Molecular therapy : the journal of the American Society of Gene Therapy, pp. 359-370, vol. 22(No. 2) (Feb. 2014).
Ibrahim et al., "CD38 expression as an important prognostic factor in B-cell chronic lymphocytic leukemia", Blood, pp. 181-186, vol. 98(No. 1) (Jul. 2001).
Jares et al., "Molecular pathogenesis of mantle cell lymphoma" The Journal of clinical investigation, pp. 3416-3423, vol. 122(No. 10) (Oct. 2012).
Jayaraman et al., "Maximizing the potency of siRNA lipid nanoparticles for hepatic gene silencing in vivo", Angewandte Chemie (International ed. in English), pp. 8529-8533, vol. 51(No. 34) (2012).
Kim et al., "RNAi-mediated CCR5 silencing by LFA-1-targeted nanoparticles prevents HIV infection in BLT mice" Molecular therapy : the journal of the American Society of Gene Therapy, pp. 370-376, vol. 18(No. 2) (Dec. 2010).
Klier et al., "Specific lentiviral shRNA-mediated knockdown of cyclin D1 in mantle cell lymphoma has minimal effects on cell survival and reveals a regulatory circuit with cyclin D2", Leukemia pp. 2097-2105, vol. 22(No. 11) (Sep. 2008).
Lee et al., "T cell-specific siRNA delivery using antibody-conjugated chitosan nanoparticles" Bloconjugate chemistry, pp. 1174-1180, vol. 23(No. 6)(2012).
Leung et al., "Lipid nanoparticles for short interfering RNA delivery" Advances in genetics, pp. 71-110, vol. 88 (2014).
Naresh et al., "Optimal processing of bone marrow trephine biopsy: the Hammersmith Protocol", Journal of clinical pathology, pp. 903-911, vol. 59(No. 9)(Feb. 2006).
Neff et al., "An aptamer-siRNA chimera suppresses HIV-1 viral loads and protects from helper CD4+ T cell decline in humanized mice", pp. 1-12, Science translational medicine, vol. 3(No. 66) (Jan. 2011).
Novobrantseva et al., "Systemic RNAi-mediated Gene Silencing in Nonhuman Primate and Rodent Myeloid Cells" Molecular therapy. Nucleic acids pp. 1-13 vol. 1:e4, (2012).
Peer & Lieberman, "Special delivery: targeted therapy with small RNAs" Gene therapy, pp. 1127-1133, vol. 18 (No. 12) (Febraury 2011).
Peer et al., "Nanocarriers as an emerging platform for cancer therapy", Nature nanotechnology, pp. 751-760, vol. 2(No. 12) (Dec. 2007).
Peer et al., "Selective gene silencing in activated leukocytes by targeting siRNAs to the integrin lymphocyte function-associated antigen-1", Proceedings of the National Academy of Sciences, pp. 4095-4100, vol. 104(No. 10)(Mar. 2007).
Peer et al., "Systemic Leukocyte-Directed siRNA Delivery Revealing Cyclin D1 as an Anti-Inflammatory Target" Science, pp. 627-630, vol. 319(No. 5863) (Feb. 2008).
Peer, "Induction of therapeutic gene silencing in leukocyte-implicated diseases by targeted and stabilized nanoparticles: a mini-review", Journal of Controlled Release, pp. 63-68, vol. 148(No. 1)(Jun. 2010).
Peer, "A daunting task: manipulating leukocyte function with RNAi", Immunological reviews, pp. 185-197, vol. 253 (No. 1)(2013).
Peer, "Harnessing RNAi nanomedicine for precision therapy" Molecular and cellular therapies, pp. 1-11, vol. 2 No. 5 (2014).
Perez-Galan et al., "Bortezomib resistance in mantle cell lymphoma is associated with plasmacytic differentiation" Blood, pp. 542-552, vol. 117(No. 2) (Jan. 2011).
Perise-Barrios et al., "Carbosilane dendrimers as gene delivery agents for the treatment of HIV infection" Journal of Controlled Release, pp. 51-57, vol. 184 (Mar. 2014).
Phipps et al., "Daratumumab and its potential in the treatment of multiple myeloma: overview of the preclinical and clinical development", Therapeutic advances in hematology, pp. 120-127, vol. 6(No. 3) (2015).
Ramishetti et al., "Systemic Gene Silencing in Primary T Lymphocytes Using Targeted Lipid Nanoparticles" ACS nano, pp. 6706-6716, vol. 9(No. 7)(Jun. 2015).
Sherr & Roberts, "Living with or without cyclins and cyclin-dependent kinases", Genes & development, pp. 2699-2711, vol. 18(No. 22)(2004).
Song et al., "RNA interference targeting Fas protects mice from fulminant hepatitis" Nature medicine,pp. 347-351, vol. 9(No. 3) (Feb. 2003).
Tam et al., "Advances in Lipid Nanoparticles for siRNA Delivery", Pharmaceutics, pp. 498-507, vol. 5(No. 3) (Sep. 2013).
Tchakarska et al., "The targeting of the sole cyclin D1 is not adequate for mantle cell lymphoma and myeloma therapies", Haematologica, pp. 1781-1782, vol. 94(No. 12)(2009).
Tezgel et al., "Novel protein transduction domain mimics as nonviral delivery vectors for siRNA targeting NOTCH1 in primary human T cells", Molecular Therapy, pp. 201-209, vol. 21 (No. 1)(Jan. 2013).
Todisco et al., "CD38 ligation inhibits normal and leukemic myelopoiesis", Blood, pp. 535-542, vol. 5(No. 2) (Jan. 2000).
Vaisitti et al., "The enzymatic activities of CD38 enhance CLL growth and trafficking: implications for therapeutic targeting", Leukemia pp. 356-368, vol. 29(No. 2)(Jul. 2014).
Wang et al., "Targeting BTK with ibrutinib in relapsed or refractory mantle-cell lymphoma" The New England journal of medicine, pp. 507-516, vol. 369(No. 6)(Aug. 2013).
Weinstein & Peer, "Rnai nanomedicines: challenges and opportunities within the immune system" Nanotechnology, pp. 1-14, vol. 21 (No. 23) (Apr. 2010).
Weinstein et al., "RNA Inhibition Highlights Cyclin D1 as a Potential Therapeutic Target for Mantle Cell Lymphoma" PloS one, pp. 1-5, vol. 7(No. 8)(Jul. 2012).
Weinstein et al., "Harnessing RNAi-based nanomedicines for therapeutic gene silencing in B-cell malignancies" Proceedings of the National Academy of Sciences, pages E16-E22, vol. 113(No. 1)(Dec. 2015).
Wittrup & Lieberman, "Knocking down disease: a progress report on siRNA therapeutics" Nature reviews, pp. 543-552, Genetics, vol. 16(No. 9)(Sep. 2015).
Wong & Comenzo, "CD38 Monoclonal Antibody Therapies for Multiple Myeloma" Clinical lymphoma, myeloma & leukemia, pp. 635-645, vol. 15(No. 11)(Nov. 2015).
Yin et al., "Non-viral vectors for gene-based therapy" Nature reviews. Genetics, pp. 541-555, vol. 15(No. 8) (Jul. 2014).
Yu et al., "Targeted nanoparticle delivery overcomes off-target immunostimulatory effects of oligonucleotides and improves therapeutic efficacy in chronic lymphocytic leukemia" Blood, pp. 136-147, vol. 121(No. 1) (Jan. 2013).
Zhou et al., "Functional in vivo delivery of multiplexed anti-HIV-1 siRNAs via a chemically synthesized aptamer with a sticky bridge" Molecular Therapy, pp. 192-200, vol. 21(No. 1)(Jan. 2013).
Zimmermann et al., "Phase I first-in-humans trial of ALN-TTRsc, a novel RNA interference therapeutic for the treatment of familial amyloidotic cardiomyopathy (FAC)", Journal of Cardiac Failure, vol. 19(No. 8) (Aug. 2013).

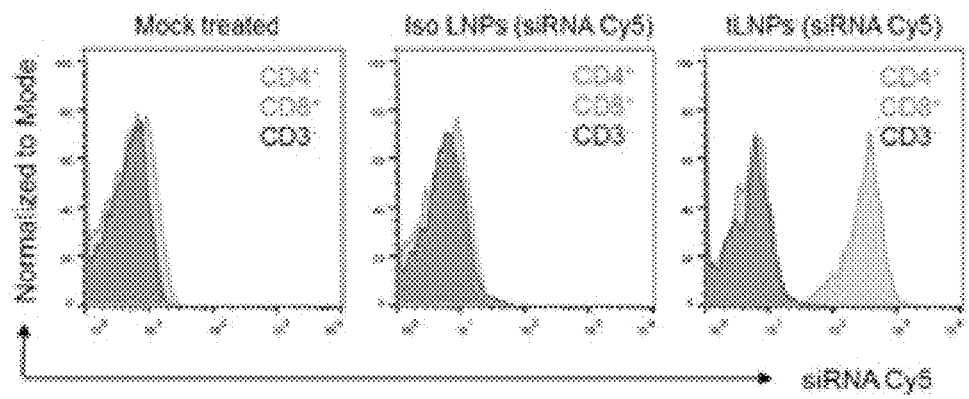
Fig. 5A
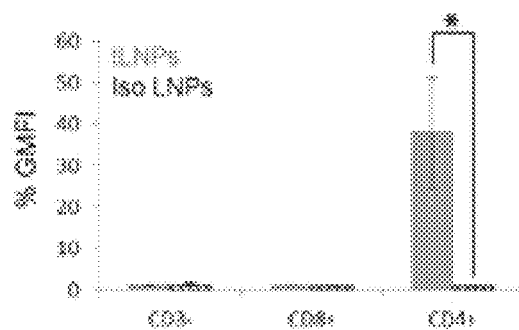
Fig. 5B
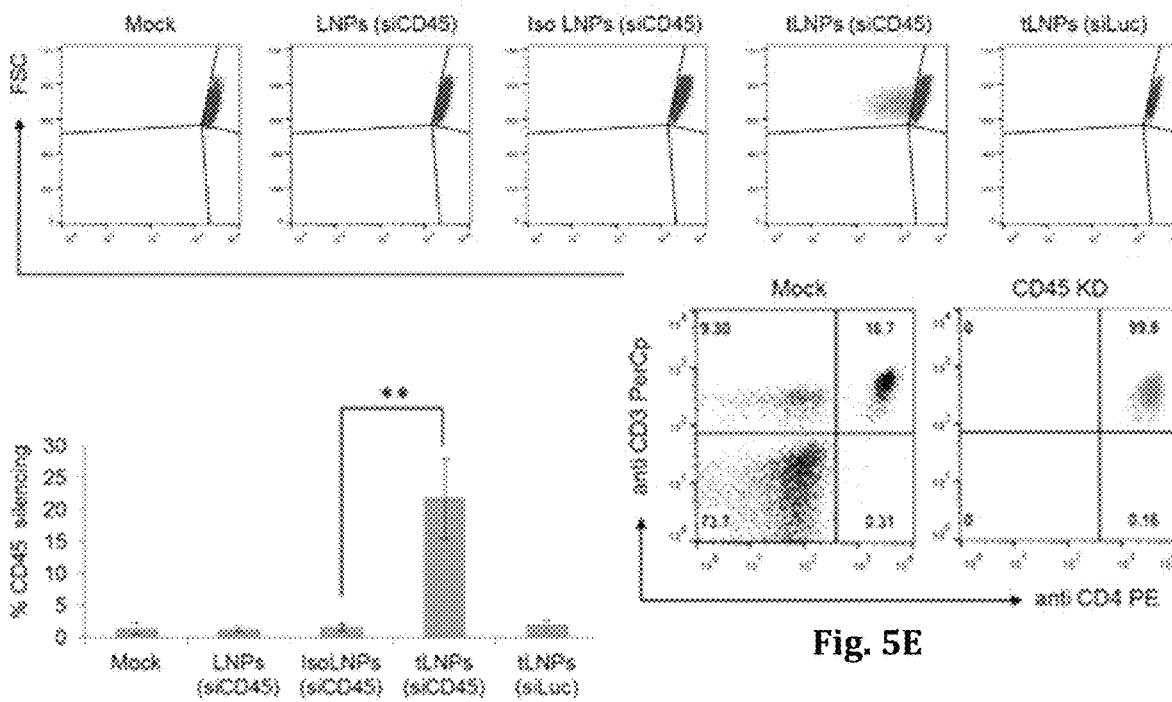
Fig. 5C
Fig. 5D
Fig. 5E

Fig. 8A
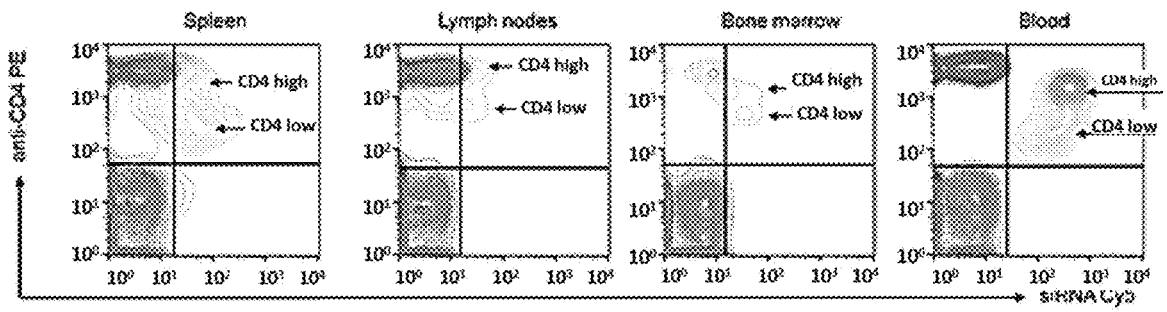
Fig. 8B
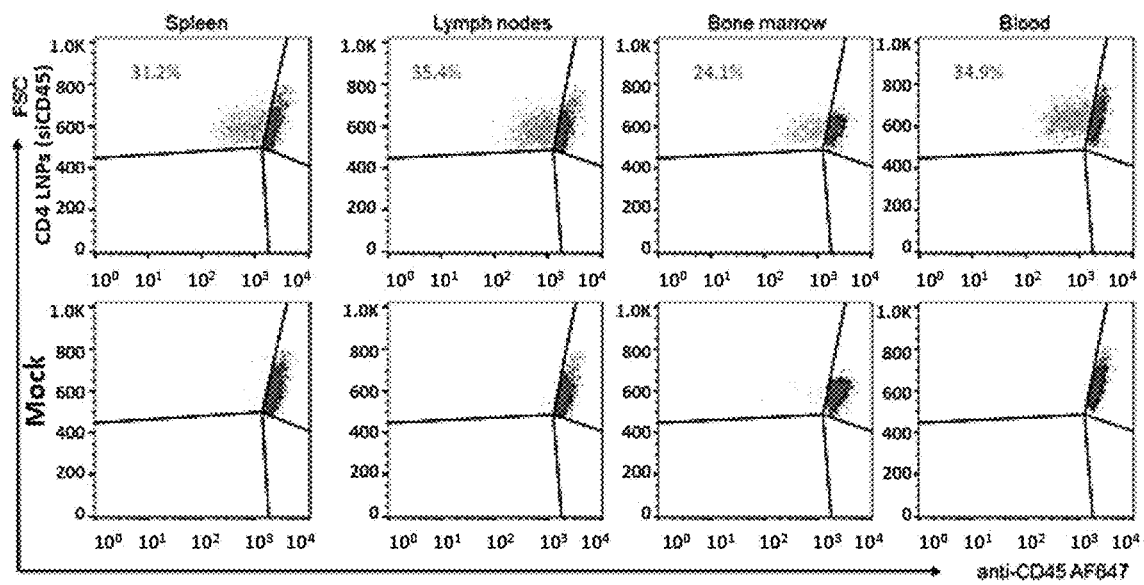
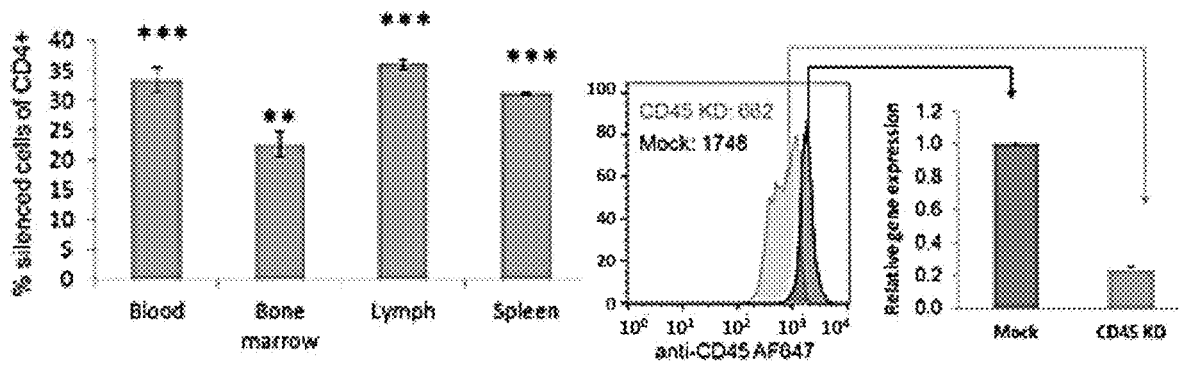
Fig. 8C
Fig. 8D

Fig. 17D
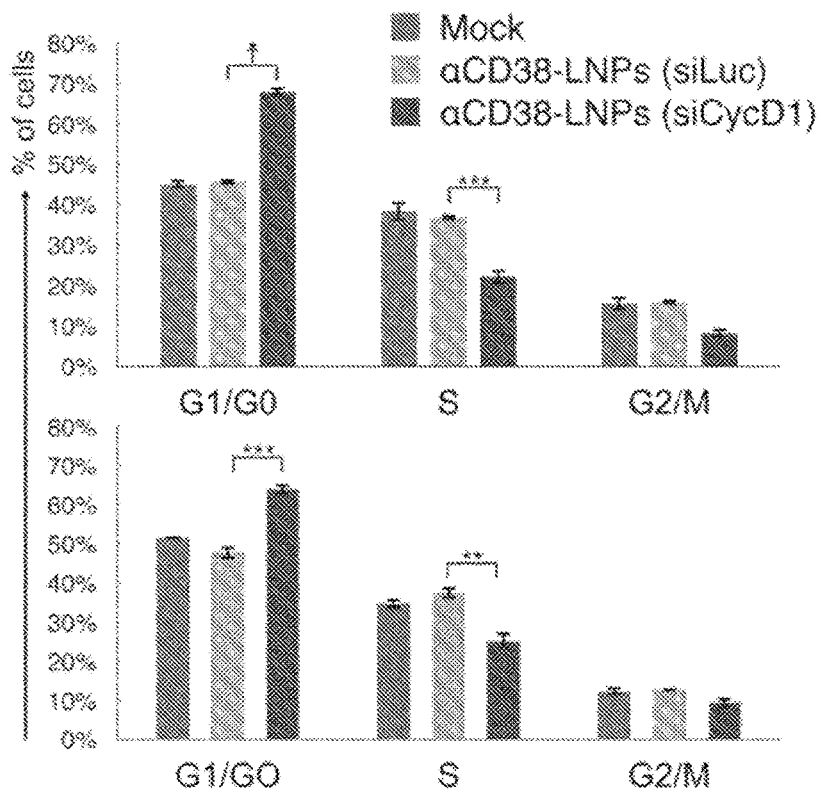
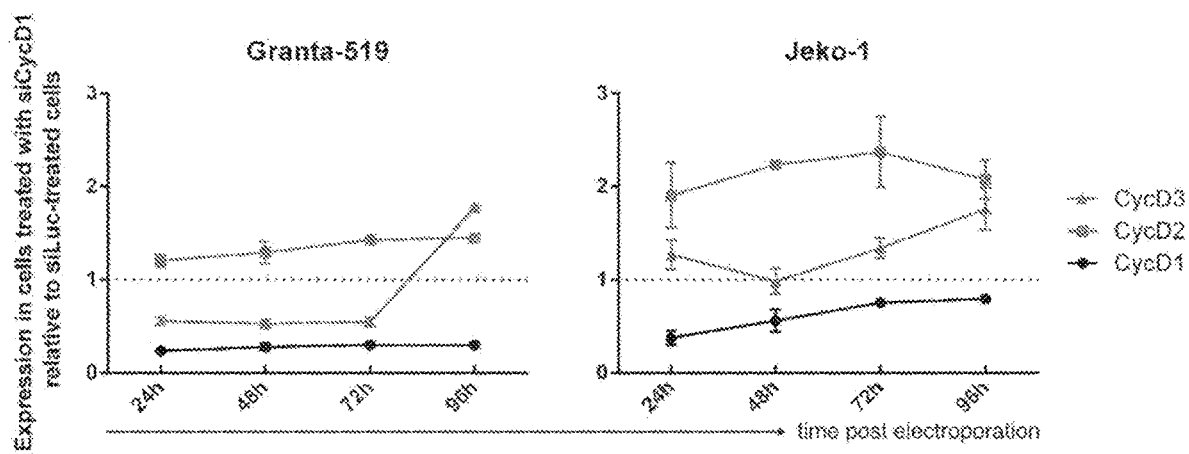
Fig. 17E

METHOD FOR TREATMENT OF A LEUKOCYTE RELATED DISEASE BY DELIVERY OF NUCLEIC ACID MOLECULES TO LEUKOCYTES USING TARGETED LIPID PARTICLES

The Sequence Listing in ASCII text file format of 3,874 bytes in size, created on Dec. 21, 2020, with the file name "2020-12-21 SequenceListing-PEER9A," filed in the U.S. Patent and Trademark Office on even date herewith, is hereby incorporated herein by reference.

FIELD OF THE INVENTION

The invention relates to targeted lipid particles for delivery of nucleic acid molecules to Leukocytes (such as primary T lymphocytes or B lymphocytes) and uses thereof.

BACKGROUND OF THE INVENTION

RNA interference (RNAi) can be activated by introducing synthetic short double-stranded RNA fragments, termed small interfering (si)RNAs, into cells to silence genes bearing complementary sequences. RNAi can serve a tool for evaluating the role of specific genes in cellular and disease processes and for therapeutic applications, by specific silencing of disease-relevant genes in a wide variety of diseases such as cancer, inflammation, neurodegenerative diseases and genetic disorders. However, the efficient, specific and safe delivery of RNAi payloads remains a major challenge facing the application of RNAi therapeutics to most diseases.

Studies have shown significant improvements in methodologies for the recognition and delivery of siRNAs to specific disease-relevant cell types. However, most of these delivery approaches have not been optimized to facilitate the intracellular trafficking of siRNAs into the cytoplasm where they provide the targeting component of the RNA-induced silencing complex (RISC) allowing it to direct the degradation of specific mRNAs.

The use of microfluidic mixing device has greatly increased the efficacy of producing Lipid-based nanoparticles (LNPs) LNPs containing mixtures of lipids, including fusogenic and ionizable amino lipids, to enhance both the encapsulation of siRNAs and endosomal escape once delivered to the target cells. Recent studies have shown the efficacy of utilizing this technology to effectively deliver siRNA to hepatocytes. Compared to most cell types, hepatocytes have been shown to be permissive to in vivo siRNA delivery, including the delivery of naked siRNAs using hydrodynamic injection.

Hematopoietic cells, such as leukocytes in general, and primary T lymphocytes and B-cells, in particular, are notoriously hard to transfect with small interfering RNAs (siRNAs). Modulating immune cells function, such as T cells and B-cells, by down regulating specific genes using RNA interference (RNAi) holds tremendous potential in advancing targeted therapies in many immune related disorders including cancer, inflammation, autoimmunity and viral infections.

CD4+T lymphocytes play essential roles in the immune system through their interaction with antigen presenting cells (APCs) and the secretion of cytokines that regulate and balance the inflammatory response. Although several strategies have been used to knockdown gene expression in T cells in vitro and in vivo, efficient and specific delivery of siRNAs to T cells in therapeutically relevant doses remains a major hurdle to the adoption of this technology for clinical applications.

MCL is an aggressive B-cell malignancy characterized by a t(11:14) chromosomal translocation that juxtaposes the proto-oncogene encoding cyclin D1 (cycD1) to the immunoglobulin heavy chain gene promoter. This leads to constitutive over-expression of cycD1, a protein that is not expressed in healthy B-lymphocytes. Current MCL therapy mainly relies on conventional chemotherapy, anti-CD20 cytotoxic monoclonal antibodies, autologous stem cell transplantation, and more recently, small molecule inhibitors of critical molecular pathways, such as the BTK inhibitor, ibrutinib. Unfortunately, relapse and progressive resistance to treatment lead to short median survival. MCL has one of the worst prognoses among lymphomas. It was previously shown that cycD1 downregulation in MCL cell lines using RNAi inhibits proliferation and causes cell cycle arrest and apoptosis. Yet, the clinical application of this approach is hindered by the lack of appropriate systems that could deliver RNAi payloads to MCL cells in an efficient and safe manner. RNAi therapeutics for B-cell malignancies is especially challenging, since these cells are dispersed and are intrinsically resistant to transfection with nucleic acids. CD38 is expressed on the surface of immature hematopoietic cells, including immature B cells. Its expression is tightly regulated during B cell ontogeny—it is expressed on bone marrow precursors, but not mature B cells. CD38 is expressed on most MCLs.

Several in vivo studies have suggested that LNP-based approaches may be effective for targeting leukocytes. For example, Novobrantseva et al. demonstrated gene knockdown in murine peritoneal macrophages in vivo, and while He et. al showed robust gene silencing in human T cells in vitro, and a moderate level of generalized (i.e. not specific to any lymphocyte population) silencing in spleen and bone marrow hematopoietic tissues.

Nevertheless, there is a need in the art for suitable and efficient, specifically targeted delivery platforms for potent gene silencing using siRNA technology in leukocytes, in particular specific subsets of leukocytes, including primary lymphocytes, such as B-cells and T-cells, and their use in new diagnostic and therapeutic approaches to dampen leukocytes related conditions, such as, inflammation and the harmful immune responses that occur during autoimmunity, lymphotropic viral infections (such as HIV), and/or to treat cancers, such as, blood cancers, including lymphomas, such as MCL.

SUMMARY OF THE INVENTION

According to some embodiments, there are provided targeted lipid-based particles, compositions comprising the same and uses thereof for the efficient, targeted delivery of nucleic acids (such as inhibitory RNA molecules) to leukocytes, such as primary lymphocytes (including B-cells and T-cells).

According to some embodiments, there are provided targeted lipid-based particles, which include a plurality of lipids and a PEG-maleimide moiety/derivative, conjugated to a targeting moiety; and optionally nucleic acid encapsulated within. The targeted lipid-based particles are in particular efficient in specific delivery of nucleic acid molecules, to specific subsets of leukocytes, such as, primary lymphocytes, including T cells (such as, CD4+ T Cells) and B-cells. In some embodiments, the disclosed targeted particles can be utilized in various diagnostic and therapeutic applications of leukocyte-related conditions, such as, cancer, viral infections and autoimmunity.

According to some embodiments, the present invention is based in part on an advantageous composition of lipid-based particles, which enables a specific, targeted delivery of nucleic acid molecules (such as siRNA), to leukocytes (such as lymphocytes), which is a challenging and non-trivial task, since such cells are dispersed and are intrinsically resistant to transfection with nucleic acid molecules. Advantageously, in order to increase the efficacy of nucleic acid molecules (such as siRNA) delivery, the targeted tLNPs are formulated with several lipids designed to improve the stability and efficacy of siRNA delivery, as well as additional moieties, such as PEG and/or maleimide. The targeted LNPs are surface functionalized with targeting moieties (such as, antibodies, peptides or ligands) that specifically recognize cell surface antigens whose expression is restricted to or enriched on specific cell type, and which allow delivery to specific subtypes of leukocytes. In some embodiments, the targeting moiety is an antibody. For example, in some exemplary embodiments, the targeted particles are conjugated to a specific anti-CD4 monoclonal antibody (mAb), which allows specific delivery of the siRNAs encapsulated within the particles only to CD4+T lymphocytes, and not other subtypes of leukocytes. For example, in some exemplary embodiments, the targeted particles are conjugated to a specific anti-CD38 monoclonal antibody (mAb), which allows specific delivery of the siRNAs encapsulated within the particles only to B-cell lymphocytes malignancies (such as MCL), and not other subtypes of leukocytes.

According to some embodiments, the particles disclosed herein are advantageous as they are uniformly sized, while exhibiting a small, nanoscale mean diameter (average diameter of about 58 nm) and extremely high encapsulation rate (close to 100%) of siRNA as the nucleic acid. Further, the preparation method of the particles, which utilize a microfluidic mixer system is advantageous as it allows a temporally efficient process, which avoids the use of extrusion of lipid particles through appropriately sized filters.

According to some embodiments, the particles disclosed herein and methods of use thereof are advantageous since knockdown of lymphatic cells, such as B cells and T-cells has not been previously demonstrated with such lipid-based targeted particles. Likewise, it has not been previously demonstrated that MCL cells can be targeted with lipid-based particles, in vivo, and further, that specific target gene can be knocked-down in these cells and that can in vivo selectively kill these cells.

According to some embodiments, the particles disclosed herein are particularly advantageous for use in hematological tissues. The blood supply in the hematological tissues, where MCL cells mostly reside, including spleen and bone marrow, is made up of sinusoids that allow small nanoparticles tissue access. Selective targeting of lymphoma cells by antibody-targeted delivery is clinically beneficial since it can reduce the total amount of drug required for therapeutic benefit and reduce toxicity to bystander cells.

According to some embodiments, the present invention is further based on the surprising finding that the internalization of the targeted particles and not endosome escape is a fundamental event that takes place as early as one hour after systemic administration, that determine tLNPs efficacy. Thus, contrast to the belief that an obstacle for effective gene silencing by siRNA delivery systems resides in siRNA endosome escape, the findings provided herein demonstrate that the internalization of the siRNA is a bottleneck of leukocytes targeted siRNA delivery.

According to some embodiments, as further exemplified herein, the targeted particles disclosed herein can be advantageously administered systemically (for example, by intravenous administration) to result in efficient binding and uptake into the targeted leukocytes (such as, for example, CD4+T lymphocytes, MCL cells), in several relevant anatomical sites, including, for example, the spleen, inguinal lymph nodes, blood and the bone marrow.

According to some embodiments, the particles disclosed herein comprise a robust and scalable ionizable lipid-based particles system. According to some embodiments, the particles disclosed herein incorporate a plurality of lipids, including fusogenic ionizable lipids (such as, DLin-MC3-DMA, DLinDMA, DLin-KC2-DMA), PEG and maleimide derivatives/moieties, and are further coated/conjugated to targeting antibodies (such as monoclonal antibodies) aimed at specific antigens of the desired leukocyte to be targeted (such as, for example, a T cell surface CD4 receptor, CD8 receptor, CD3 receptor, CD25, CD47, CD147, CD117, CD38 (for B-cells), integrin 7 (for B-cells), and the like) Each possibility is a separate embodiment.

According to some embodiments, the disclosed targeted particles allows the specific targeted delivery of nucleic acid molecules, such as inhibitory RNA molecules to a target leukocyte, to exert a downstream effect on the specific leukocyte sub-type. In some exemplary embodiments, the inhibitory RNA molecules can be used to induce killing of the target cell and/or modulate the fate of the cells, depending on the target gene to be targeted by the inhibitory nucleic acid molecules.

According to some exemplary embodiments, the lipid-based particles may be decorated with a monoclonal antibody against CD38, which is expressed on Human diseased B cells. By targeting such cells with the targeted lipid particles and by selective inhibition of a cell cycle regulator, such as, Cyclin D1, expressed on several types of the hematological malignancies (such as mantle cell lymphoma, and multiple myeloma), death of the specific cell population (and hence the malignancy) is induced.

According to some embodiments, the targeting moiety may include any type of molecule capable of specifically recognize and interact/bind with cell surface antigens whose expression is restricted to or enriched on specific cell. In some embodiments, the targeting moiety may be selected from, but not limited to: antibodies, peptides, ligands, ligand-mimic, agonists and/or antagonists. In some embodiments, the targeting moiety may be any type of antibody, or a fragment thereof. In some embodiments, the targeting antibody is a monoclonal antibody.

According to some embodiments, there is provided a targeted particle for delivery of a nucleic acid to leukocyte cell, the particle comprising a lipid mixture comprising cationic lipid, membrane stabilizing lipid and PEG-maleimide conjugated to a targeting moiety. In some embodiments, the particles encapsulate nucleic acid molecule.

According some embodiments, there is provided a targeted particle for delivery of a nucleic acid to leukocyte cell, the particle comprising: a) a lipid mixture comprising cationic lipid, membrane stabilizing lipid and PEG-maleimide conjugated to a targeting moiety; and b) nucleic acid molecules encapsulated within the particle.

In some embodiments, the particle is for targeted delivery of a nucleic acid to primary lymphocytes. In some embodiments, the lymphocytes are selected from B-cells and T-cells. In some embodiments, the lymphocytes are B-cells. In some embodiments, the lymphocytes are T-cells.

In some embodiments, the targeting moiety is configured to specially target a leukocyte. In some embodiments, the targeting moiety is configured to specifically recognize an antigen expressed by said leukocyte. In some embodiments, the targeting moiety is selected from an antibody, a peptide and/or a ligand. In some embodiments, the targeting moiety comprises an antibody or a fragment thereof. In some embodiments, the antibody is anti-CD-38 antibody. In some embodiments, the targeting antibody is selected from anti-CD-antibody, anti CD8 antibody and anti-CD3 antibody. Each possibility is a separate embodiment. In some embodiments, the targeting antibody is anti-CD4 antibody. In some embodiments, the targeting antibody is anti-CD8 antibody. In some embodiments, the targeting antibody is anti-CD3 antibody.

In some embodiments, the nucleic acid comprises an interfering RNA, selected from, siRNA, miRNA, shRNA, and antisense RNA, modified forms thereof or combinations thereof.

In some embodiments, the cationic lipid may be selected from: DLinDMA, DLin-MC3-DMA, DLin-KC2-DMA, N,N-dimethyl-N',N'-di[(9Z, 12Z)-octadeca-9,12-dien-1-yl] ethane-1,2-diamine, Di-oleyl-succinyl-serinyl-tobramycin, Di-oleyl-adipyl-tobramycin, Di-oleyl-suberyl-tobramycin, Di-oleyl-sebacyl-tobramycin, Di-oleyl-dithioglycolyl-tobramycin, monocationic lipid N-[1-(2,3-Dioleoyloxy)]-N,N,N-trimethylammonium propane (DOTAP), BCAT O-(2R-1, 2-di-O-(1'Z, 9'Z-octadecadienyl)-glycerol)-3-N-(bis-2-aminoethyl)-carbamate, BGSC (Bis-guanidinium-spermidine-cholesterol), BGTC (Bis-guanidinium-tren-cholesterol), CDAN (N'-cholesteryl oxycarbony 1-3,7-diazanonane-1,9-diamine), CHDTAEA (Cholesteryl hemidithiodiglycolyl tris(amino(ethyl)amine), DCAT (0-(1, 2-di-O-(9'Z-octadecanyl)-glycerol)-3-N-(bis-2-aminoethyl)-carbamate), DC-Chol (3β[N—(N', N'-dimethylaminoethane)-carbamoyl] cholesterol), DLKD (O,O'-Dilauryl N-lysylaspartate), DMKD (O,O'-Dimyristyl N-lysylaspartate), DOG (Diolcylglycerol, DOGS (Dioctadecylamido-glycylspermine), DOGSDSO (1,2-Dioleoyl-sn-glycero-3-succinyl-2-hydroxyethyl disulfide ornithine), DOPC (1,2-Dioleoyl-sn-glycero-3-phosphocholine), DOPE (1,2-Dioleoyl-sn-glycerol-3-phosphoethanolamine, DOSN (Dioleyl succinyl ethylthioneomycin), DOSP (Dioleyl succinyl paromomycin), DOST (Dioleyl succinyl tobramycin), 1,2-Uiolcoyl-3-trimethyl ammoniopropane, DOTMA (N'[1-(2,3-Dioleyloxy)propyl]-N,N,N-trimethylammonium chloride), DPPES (Di-palmitoyl phosphatidyl ethanolamidospermine), DDAB and DODAP, or any combination thereof. Each possibility is a separate embodiment.

In some embodiments, the cationic lipid is selected from ionizable lipids, such as, for example, DLinDMA, DLin-MC3-DMA, DLin-KC2-DMA, Di-oleyl-succinyl-serinyl-tobramycin, Di-oleyl-adipyl-tobramycin, Di-oleyl-suberyl-tobramycin, Di-oleyl-sebacyl-tobramycin, N,N-dimethyl-N',N'-di[(9Z, 12Z)-octadeca-9,12-dien-1-yl] ethane-1,2-diamine and Di-oleyl-dithioglycolyl-tobramycin, or any combination thereof. Each possibility is a separate embodiment.

In some embodiments, the membrane-stabilizing lipid is selected from the group consisting of cholesterol, phospholipids (such as, phosphatidylcholine (PC)), cephalins, sphingolipids and glycoglycerolipids In some embodiments, the lipids may further include phosphatidylamine selected from: 1,2-dilauroyl-L-phosphatidyl-ethanolamine (DLPE), 1,2-Dioleoyl-sn-glycero-3-phosphoethanolamine (DOPE) 1,2-Diphytanoyl-sn-glycero-3-phosphoethanolamine (DPhPE) 1,3-Dipalmitoyl-sn-glycero-2-phosphoethanolamine (1,3-DPPE) 1-Palmitoyl-3-oleoyl-sn-glycero-2-phosphoethanolamine (1,3-POPE), Biotin-Phosphatidylethanolamine, 1,2-Dimyristoyl-sn-glycero-3-phosphoethanolamine (DMPE), 1,2-Distearoyl-sn-glycero-3-phosphoethanolamine (DSPE), and Dipalmitoylphosphatidylethanolamine (DPPE).

In some embodiments, the particle further include one or more PEG derivatives. In some embodiments, the additional PEG derivative is selected from: DMG-PEG, PEG-cDMA, 3-N-(-methoxy poly(ethylene glycol)2000)carbamoyl-1,2-dimyristyloxy-propylamine; PEG-cDSA, 3-N-(-methoxy poly(ethylene glycol)2000)carbamoyl-1,2-distearyloxy-propylamine, PEG-Amine, DSPE-PEG, or combinations thereof.

In some embodiments, the maleimide moiety is conjugated to a PEG derivative.

In some embodiments, the lipid mixture comprises DLin-MC3-DMA, cholesterol, DSPC, PEG-DMG and DSPE-PEG-maleimide. In some embodiments, the lipid mixture comprises DLinDMA, cholesterol, DSPC, PEG-DMG and DSPE-PEG-maleimide. In some embodiments, the lipid mixture comprises DLinKC2DMA, cholesterol, DSPC, PEG-DMG and DSPE-PEG-maleimide.

In some embodiments, the percentage of encapsulation of the nucleic acid is over 90%.

In some embodiments, there is provided a composition comprising a plurality of the targeted particles. In some embodiments, there is provided a composition comprising a plurality of the targeted particles encapsulating nucleic acid molecule(s). In some embodiments, there is provided a pharmaceutical composition comprising the plurality of particles in a dosage form suitable for administration via a route selected from oral and parenteral. In some embodiments, the administration is systemic.

According to some embodiments, there is provided a method for treating a leukocyte associated disease, comprising the step of administering to a subject in need thereof a pharmaceutical composition comprising the targeted particles and suitable nucleic acid molecules encapsulated therein. In some embodiments, the leukocyte associated disease is cancer. In some embodiments, the leukocyte associated disease is blood cancer. In some embodiments, the blood cancer is selected from lymphoma, leukemia and multiple myeloma. In some embodiments, the cancer is lymphoma. In some embodiments, the lymphoma is selected from B-cell lymphoma and T-cell lymphoma. In some embodiments, the B-cell lymphoma is selected from Hodgkin's lymphoma and non-Hodgkin's lymphoma. In some embodiments, the B-cell lymphma is selected from Burkitt lymphoma, chronic lymphocytic leukemia/small lymphocytic lymphoma (CLL/SLL), diffuse large B-cell lymphoma, follicular lymphoma, marginal-zone B-cell lymphoma, Nodal marginal zone B cell lymphoma (NMZL), Splenic marginal zone lymphoma (SMZL), Intravascular large B-cell lymphoma, Primary effusion lymphoma, Lymphomatoid granulomatosis, Primary central nervous system lymphoma, ALK-positive large B-cell lymphoma, Plasmablastic lymphoma and mantle cell lymphoma (MCL). In some embodiments, the lymphoma is Mantle cell lymphoma (MCL).

In some embodiments, the T-cell lymphoma is selected from: Peripheral T-cell lymphoma, Anaplastic large cell lymphoma, Angioimmunoblastic Lymphoma, Cutaneous T-cell lymphoma, Adult T-cell Leukemia/Lymphoma (ATLL), Blastic NK-cell Lymphoma, Enteropathy-type T-cell lymphoma, Hematosplenic gamma-delta T-cell Lymphoma, Lymphoblastic Lymphoma, Nasal NK/T-cell Lymphomas and Treatment-related T-cell lymphomas. In some embodiments, for treating the leukocyte associated disease, the siRNA encapsulated within the particles is siRNA against a cell cycle regulator. In some embodiments, the cell cycle regulator may be selected from: Polo-like Kinase 1 (PLK), Cyclin D1, CHK1, Notch pathway genes, PDGFRA, EGFRvIII, PD-L1, RelB, STAT1, STAT3, MCL1, CKAP5, RRM1, SF3A1 and CDK11B, and the like, or combinations thereof. In some embodiments, the cell cycle regulator is Cyclin D1 (CycD1).

According to some embodiments, there is provided use of a pharmaceutical composition for treating a leukocyte-associated disease, the composition comprising: a) targeted particles for delivery of a nucleic acid to a leukocyte, the particle comprising a lipid mixture comprising cationic lipid, membrane stabilizing lipid and PEG-maleimide conjugated to a targeting moiety; and b) nucleic acid encapsulated within the particle. In some embodiments, the pharmaceutical compositions comprises a plurality of particles.

According to some embodiments, there is provided use of a pharmaceutical composition for treating a leukocyte-associated disease, the composition comprising targeted particle for delivery of a nucleic acid to a leukocyte, the particle comprising: a) a lipid mixture comprising cationic lipid, membrane stabilizing lipid and PEG-maleimide conjugated to a targeting moiety; and b) nucleic acid encapsulated within the particle.

In some embodiments, the leukocyte-associated disease is cancer. In some embodiments, the cancer is lymphoma. In some embodiments, the lymphoma is Mantle cell lymphoma (MCL).

In some embodiments, the nucleic acid is siRNA. In some embodiments, the siRNA is directed against a cell cycle regulator. In some embodiments, the cell cycle regulator is Cyclin D1.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 4A—Flow cytometry dot blot analysis of gated live lymphocyte population, dots indicating tLNPs (upper right quartet) and isoLNPs (upper left quartet); FIG. 4B—Corresponding histograms of % GMFI calculated for CD4$^+$ population over CD4$^-$ populations including CD8 and CD19 cells, data presented as mean±SD, n=3, ***p<0.0005; FIG. 4C—Splenocytes were incubated for further 30 min at 37° C. to allow internalization. Cells were stained with Hoechst and calcein for nuclear and cytoplasm detection followed by membrane staining with anti-CD4-AF594. Cells were analyzed by confocal microscopy for internalization (left panel); representative individual images of area (a) shown in the right panels. GMFI. Geometric mean fluorescence intensity; FIG. 4D—Ex vivo specific binding of tLNPs: Splenocytes were collected from mouse and lymphocytes were incubated with tLNPs (siCy5) for 30 min at 4° C., followed by 30 min at room temperature. Cells were washed and stained with anti-CD4-PE (originally red) and anti-CD8-FITC (originally green), then analyzed by confocal microscopy. Merged image (left panel), individual images of each fluorophore (right). tLNPs shown (originally cyan);

FIGS. 5A-E show tLNPs can target blood circulating CD4$^+$ T cells in vivo and induce gene silencing. FIG. 5A—Targeting blood CD4$^+$ T cells in vivo—One hour post i.v. administration of tLNPs (siCy5) or isoLNPs (siCy5), circulating lymphocytes were isolated and stained with a set of antibodies (anti-CD4 PE, anti-CD3 PerCp and anti-CD8 FITC). Representative histograms of flow cytometry analysis of LNPs binding profile in blood lymphocytes from two independent experiments are shown; FIG. 5B—Corresponding bar graphs of the histrograms of FIG. 5A are presented as percent GMFI values over mock, data represent mean±SD, n=3, *p<0.05; FIG. 5C—tLNPs silence CD45 in blood T lymphocytes. Mice were injected with tLNPs (siCD45), saline (mock), tLNPs(siLuc), isoLNPs(siCD45) or LNPs (siCD45) as controls. Five days post i.v. administration, circulating lymphocytes were isolated and stained for CD45 expression. The flow cytometry analysis of dot blots gated for live lymphocytes is shown. Results were mean of two independent experiments, n=5; FIG. 5D—Corresponding histograms of FIG. 5C, of percent CD45 silencing calculated from CD4 gated populations, data represent mean±SD, n=5, **p<0.005; FIG. 5E—CD45 is silenced specifically in CD4$^+$ circulating T cells. Five days after administration of saline or tLNPs (siCD45), circulating lymphocytes were isolated and stained with a set of antibodies. Presented is a Flow cytometry dot blot profile of CD45 silenced cell population gated for CD4$^+$/CD3$^+$ cells, n=5; KD—knock down;

FIGS. 8A-D—tLNPs target and silence CD4$^+$ T cells in hematopoietic organs. FIG. 8A-tLNPs binding CD4$^+$ cells in diverse hematopoietic organs in vivo. One-hour post administration of siCy5 containing tLNPs (originally range) or saline (originally gray), spleen, lymph nodes, bone marrow and blood lymphocytes were isolated and stained with a set of antibodies (anti-CD4 PE, anti-CD3 PerCp and anti-CD8 FITC). Representative dot blot analysis for gated live lymphocytes is presented, data were obtained from two independent experiments, n=5 mice/group; FIG. 8B—CD4 specific silencing in hematopoietic organs. Five days after administration of tLNPs (siCD45) (orange) or saline (gray) administration, spleen, lymph nodes, bone marrow and blood lymphocytes were isolated and incubated with a set of antibodies (anti-CD45 AF647, anti-CD4 PE, anti-CD3 PerCp and anti-CD8 FITC). Representative dot blot analysis for gated live CD4+ lymphocytes; FIG. 8C—Corresponding bar graphs of FIG. 8B, error bars represent mean±SD, n=5 mice/group, *p<0.0005, p<0.005 are compared to mock treated sample; FIG. 8D—The Silencing of CD45 in CD4+ T cells at the mRNA level. Gated CD45$^{KD}$ and mock CD4+ T cells were collected by BD FACSARIAIII™ cell sorter, mRNA was isolated and CD45 mRNA levels were tested by qPCR. All values are normalized to murine PPIB gene expression (endogenous control);

FIG. 10A—Lymphocytes from spleen, blood, lymph and bone marrow were isolated, one hour post administration of tLNPs (siCy5) at 1 mg/kg or 2 mg/kg siRNA dose. Representative histograms of percent GMFI values for Cy5 calculated from gated CD4 populations normalized to mock; FIG. 10B—Five days after the administration of tLNPs (siCD45) at 0.5, 1 and 2 mg/kg siRNA amounts, lymphocytes were collected from different organs, stained and analyzed by flow cytometry. Representative histograms for CD45 silenced CD4 cells (%) from gated CD4+/CD45+ populations. Error bars represents mean±SD, n=3, *p<0.05, ***p<0.0005;

FIG. 11A—Flow cytometry dot blot analysis presenting CD4high, CD4low and CD4-populations; FIG. 11B—Corresponding histograms representing high staining of CD3 for both CD4low and CD4high populations;

FIG. 12A—one hour post tLNPs (siCy5) administration, splenocytes were isolated, stained with anti-Rat Fc followed by anti-CD4 PE and analyzed by flow cytometry, analysis is presented on gated populations; FIG. 12B—Splenocytes collected from tLNPs (siCy5) treated mice were stained with Hoechst, calcein and anti-CD4 PE. Cells were analyzed by confocal microscopy. CD4high and CD4low cells are marked with green and white arrows respectively; FIG. 12C—One hour post administrations of tLNPs or iso LNPs (siCD45), splenocytes were collected, labeled with anti-CD4 PE. CD4+ T cells of isoLNPs, CD4high (green), CD4low (red) cells of tLNPs were separated using BD FACSArieIII™ cell sorter; FIG. 12D—Sorted cells were cultured in vitro for 3 days, then stained with anti-CD45-AF647 and analyzed by flow cytometry; FIG. 12E—Corresponding bar graphs, error bars represent mean±SD, n=3 mice/group, *p=0.006;

FIG. 13A—The distribution of tLNPs in mouse at 1 h and 4 h plotted against GMFI values of Cy5 calculated from gated CD4 population; FIG. 13B—Distribution of tLNPs in CD4low cells after 1 h and 4 h administration of tLNPs. Error bars represents mean±SD, n=3, NS=not significant;

FIG. 14A—Indicated organs were extracted when mice developed hindleg paralysis. Single-cell suspensions were prepared and analyzed for Granta-GFP presence by flow cytometry (GFP+/hCD45+). FIG. 14B—H&E stain on femur bones from untreated and MCL-bearing mice.

FIG. 15A—αCD38 mABb binding to 4 MCL cell lines. Continuous line: αCD38. Dashed lines: isotype control. FIG. 15B—αCD38 mAb binding to MCL cells (CD5+/CD19+) relative to non-MCL leukocytes present in blood samples from MCL patients. Each dot represent one sample (n=5), horizontal bar represents mean (*P<0.05; two-tailed Student's t test for paired values). FIG. 15C—αCD38 mAb internalization upon binding to Granta-519 cells. White scale bar: 20 µm. FIG. 15D—in vivo binding of αCD38 mAb to different organs in representative MCL bearing mouse. Indicated organs were extracted 2 h post αCD38 mAb injection, suspended and analyzed by flow cytometry. αCD38 mAb can be found on most MCL cells (Granta-GFP cells) in the BM.

FIG. 16A—Granta-GFP (left) or Jeko-GFP (right) were co-cultured with TK-1 (murine T-lymphoma) cells and incubated with αCD38-LNPs-siRNA entrapping labeled siRNA. FIG. 16B—Mononuclear cells from 2 blood samples of MCL patients were incubated with αCD38-LNPs-siRNA including labeled siRNA. FIG. 16A and FIG. 16B exhibit siRNA-LNPs binding to non-B cells (originally grey), MCL cells (originally red) or MCL cells in samples incubated with free competing αCD38 mAbs prior to αCD38-LNPs-siRNA incubation (originally purple). FIG. 16C—Granta-519 cells uptake of siRNA delivered via indicated LNPs and visualized by live confocal microscopy. White scale bar: 20 µm.

FIGS. 17A-E—αCD38-LNPs-siRNA mediate active delivery of siRNA specifically into MCL cells and induce anti-tumor gene silencing. FIG. 17A and FIG. 17B—Granta-519 (higher panels) or Jeko-1 (lower panels) were incubated with mock (black), αCD38-LNPs-siLuc (grey) or αCD38-LNPs-siCycD1 (red). 48 h post treatment, cells were analyzed for cycD1 protein expression by flow cytometry. FIG. 17A show representative data from one of five (Granta) or three (Jeko) experiments. Continuous lines: cycD1 staining. Dashed lines: isotype control. Filled histogram: unstained. Complete data are represented in FIG. 17B—Bar plots represent mean±SEM of cycD1 expression normalized to mock (P<0.01; *P<0.001; One-way ANOVA test with Bonferroni correction). FIG. 17C—qRT-PCR quantification of cyclin D1 transcripts in MCL cell lines. RNA was extracted from cells 48 h following treatment with mock, αCD38-LNPs-siLuc or αCD38-LNPs-siCycD1. Bar plots represent mean±SEM of cycD1 expression relative to mock (n=3 independent experiments per cell line, **P<0.01: One-way ANOVA test with Bonferroni correction); FIG.

17D—Cell cycle distribution of cells 48 h post treatments with mock (black), αCD38-LNPs-siLuc (grey) or αCD38-LNPs-siCycD1 (originally red) analyzed by flow cytometry. Bars represent mean percentage SEM of n=4 from two independent experiments per cell line (P<0.01; *P<0.001; †P<10-4; One-way ANOVA test with Bonferroni correction); FIG. 17E—qRT-PCR analysis of CCND1, CCND2 and CCND3 mRNA levels 24, 48, 72 and 96 hours post electroporation in Granta-519 (left) and Jeko-1 (right) cells. Expression was normalized to both eIF3a and eIF3c genes and depicted as mRNA concentration relative to cells electroporated with siLuc. Data are mean±SEM of three independent experiments;

FIG. 18A FIG. 18B—Mice bearing human MCL cells were i.v. injected with mock, isotype- or αCD38-LNPs-siRNAs. Bone marrow cells were extracted 2 h later and analyzed for LNPs binding as detected by siRNA fluorescence via flow cytometry. Human MCL (left) and murine (right) cells were gated separately based on GFP, hCD20 and mCD45 expression. Cells with siRNA fluorescence levels higher than in top 1% cells from mock-treated mouse were considered positive (siRNA-positive cells are colored, cut-off represented by vertical bar). In FIG. 18A, shown are dot plots for one representative animal from each treatment group (isotype—n=2; αCD38 n=3). Number indicates percentage of siRNA-positive cells. Complete results are shown in FIG. 18B. Bar plots represent mean±SEM (ns P>0.05; ***P<0.001; two-tailed Student's t test). FIG. 18C—Survival curves of MCL bearing mice. Corresponding treatments (1 mg siRNA/kg body) were administered at 9 time-points (arrows) via retro-orbital route. n=10 animals per group. P values and significance were determined by Log-rank Mantel-Cox test with Bonferroni correction (*P<0.05); FIG. 18D—Repeated i.v. administration of αCD38-LNPs-siRNA did not affect mice bodyweight. Animals were inoculated and treated as in FIG. 18C. Shown are mean weight SEM of mice (n=10 per group).

DETAILED DESCRIPTION

Definitions

Figure 1A:
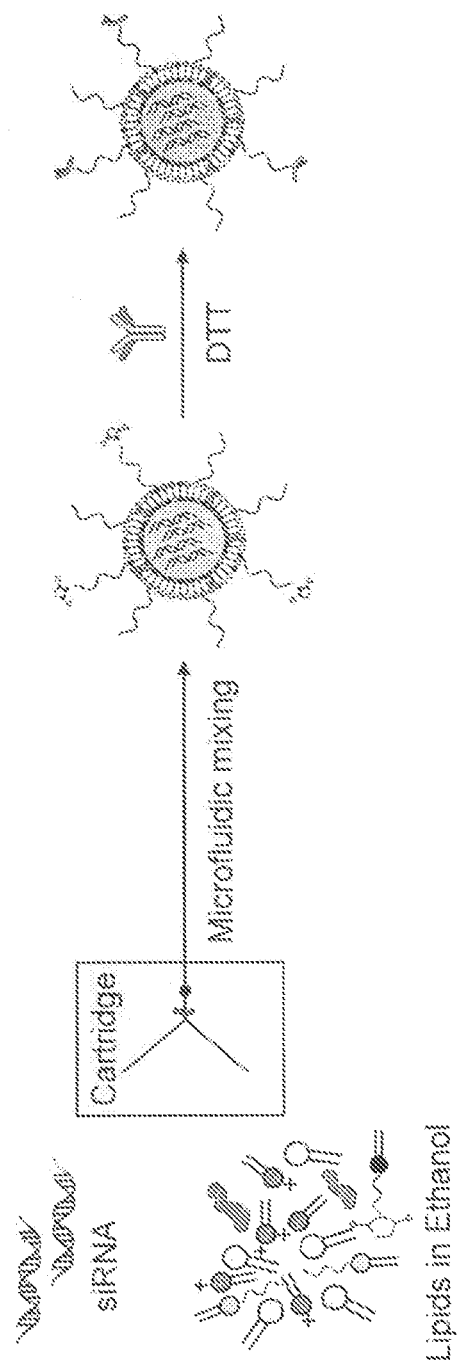
FIG. 1A—Schematic illustration of the preparation of targeted lipid-based particles (LNPs)

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As referred to herein, the terms "nucleic acid", "nucleic acid molecules" "oligonucleotide", "polynucleotide", and "nucleotide" may interchangeably be used herein.

The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, Antisense RNA, and the like. Each possibility is a separate embodiment. The terms further include oligonucleotides composed of naturally occurring bases, sugars, and covalent internucleoside linkages, as well as oligonucleotides having non-naturally occurring portions, which function similarly to respective naturally occurring portions.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "antigen" as used herein refers to a molecule or a portion of a molecule capable of being specifically bound by an antibody. An antigen may have one or more epitopes. In some embodiments, the antigen is a protein specifically expressed by a specific cell. In some embodiments, the antigen is a membranous protein. In some embodiments, the antigen is expressed on the exterior membrane of a cell. In some embodiments, the antigen is a cell surface protein. In some embodiments, the antigen is a cell surface receptor.

The term "antibody" is used in the broadest sense and includes monoclonal antibodies (mAb), including full length or intact monoclonal antibodies, polyclonal antibodies, multivalent antibodies, multi-specific antibodies (e.g., bi-specific antibodies), and antibody fragments long enough to exhibit the desired binding/recognizing activity. An "Antibody fragments" comprise a portion of an intact antibody, generally including an antigen binding site of the intact antibody and thus retaining the ability to bind an antigen.

The term "targeting moiety" is directed to any type of molecule capable of specifically recognizing and interact/bind with cell surface antigens whose expression is restricted to or enriched on specific cell. In some embodiments, the targeting moiety is selected from, but not limited to: antibodies, peptides, ligands, ligand-mimic, agonists and/or antagonists. In some embodiments, the targeting moiety may be any type of antibody, or a fragment thereof. In some embodiments, the targeting antibody is a monoclonal antibody.

The term "construct", as used herein, refers to an artificially assembled or isolated nucleic acid molecule which may include one or more nucleic acid sequences, wherein the nucleic acid sequences may include coding sequences (that is, sequence which encodes an end product), regulatory sequences, non-coding sequences, or any combination thereof. The term construct includes, for example, vector but should not be seen as being limited thereto.

"Expression vector" refers to constructs that have the ability to incorporate and express heterologous nucleic acid fragments (such as, for example, DNA), in a foreign cell. In other words, an expression vector comprises nucleic acid sequences/fragments (such as DNA, mRNA, tRNA, rRNA), capable of being transcribed. Many prokaryotic and eukaryotic expression vectors are known and/or commercially available. Selection of appropriate expression vectors is within the knowledge of those having skill in the art. In some exemplary embodiments, the expression vector may encode for a double stranded RNA molecule in the target site.

The term "expression", as used herein, refers to the production of a desired end-product molecule in a target cell. The end-product molecule may include, for example an RNA molecule; a peptide or a protein; and the like; or combinations thereof.

As used herein, the terms "introducing" and "transfection" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, and the like, or combinations thereof. The transfection of the cell may be performed on any type of cell, of any origin, such as, for example, human cells, animal cells, plant cells, virus cell, and the like. The cells may be selected from isolated cells, tissue cultured cells, cell lines, cells present within an organism body, and the like.

As referred to herein, the term "target site" refers to the location in which the nucleic acid is directed to and/or the site in which the nucleic acid is to exert its biological effect. In some exemplary embodiments, the target site is a cell that may be selected from, but not limited to: a culture cell (primary cell or cell-line derived cell), and a cell within an organism body; a tissue, an organ, a microorganism (such as, for example, virus, bacteria, parasite), and the like. The organism may be any organism, such as, but not limited to: a mammal, such as human or an animal, an animal which is not a mammal (such as, for example, avian, Fish, and the like), and the like. In some exemplary embodiments, the target site is a subcellular location or cellular organelle (such as, for example, nucleus, cytoplasm, and the like). In some embodiments, the target site is a leukocyte, or a subset thereof. In some embodiments, the target site is a specific T-cell. In some embodiments, the target site is a specific B-cell. In some embodiments, the target site is a lymphoma.

The term "treating" and "treatment" as used herein refers to abrogating, inhibiting, slowing or reversing the progression of a disease or condition, ameliorating clinical symptoms of a disease or condition or preventing the appearance of clinical symptoms of a disease or condition. The term "preventing" is defined herein as barring a subject from acquiring a disorder or disease or condition.

The term "treatment of cancer" is directed to include one or more of the following: a decrease in the rate of growth of the cancer (i.e. the cancer still grows but at a slower rate); cessation of growth of the cancerous growth, i.e., stasis of the tumor growth, and, the tumor diminishes or is reduced in size. The term also includes reduction in the number of metastases, reduction in the number of new metastases formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like. In some embodiments, the cancer is a blood cancer.

The term "Leukocytes" is directed to white blood cells (WBCs), produced and derived from a multipotent, hematopoietic stem cell in the bone marrow. The white blood cells have nuclei, and types of white blood cells can be classified in into five main types, including, neutrophils, eosinophils, basophils, lymphocytes, and monocytes, based on functional or physical characteristics. The main types may be classified into subtypes. For example, lymphocytes include B cells, T cells, and NK cells. B-cells, for example, release antibodies and assist activation of T cells. T cells, for example, can be classified to several subtypes, including: T-helper cells (CD4+Th) which activate and regulate T and B cells; cytotoxic T cells (CD8+) that can target and kill virus-infected cells and tumor cells; Gamma-delta T cells (γδ T cells) which can bridge between innate and adaptive immune responses and be involved in phagocytosis; and Regulatory (suppressor) T cells which modulate the immune system, maintain tolerance to self-antigens, and abrogate autoimmune conditions.

As used herein, the term "LNP" is directed to lipid-based nanoparticles. The lipid based particles may be targeted, when conjugated/attached/associated with a targeting moiety, such as, an antibody. In some embodiments, the particles are nano-particles. In some embodiments, the term "tLNP" is directed to the lipids based particles which are attached/coated/conjugated/linked to a targeting moiety. In some embodiments, the LNP encapsulates a nucleic acid.

The terms "maleimide" and "maleimide moiety" may interchangeably be used and are directed to a chemical compound having the formula $H_2C_2(CO)_2NH$. In some embodiments, the maleimide may be bound/conjugated/linked to another derivative, such as, PEG derivative. In some embodiments, a maleimide moiety may include two maleimide groups connected by the nitrogen atoms (Bismaleimides). In some embodiments, stable carbon-sulfur bond can be formed between the maleimide (the double bond thereof) and thiol group(s).

The term "plurality" as used herein is directed to include more than one component.

As used herein, the term "about" refers to +/−10%.

According to some embodiments of the present invention, there is provided a targeted lipid particle for delivery of a nucleic acid to a leukocyte, which comprises a lipid phase (membrane/mixture) comprising a plurality of lipids (including cationic lipid(s), membrane stabilizing lipid(s) and optionally additional lipids, such as, but limited to, ionized lipids and/or phosphatidylethanolamine(s)), one or more PEG-Amine derivatives and maleimide, conjugated to a targeting moiety. In some embodiments, the particles further include (encapsulate) a nucleic acid. In some embodiments, the maleimide is conjugated to a lipid, via PEG derivative. In some embodiments, the disclosed particles are used as an efficient delivery system (both in-vitro and in-vivo) to deliver the nucleic acid molecule to a target leukocyte, such as, a lymphocyte including B-cells and T-cells primary lymphocytes. The target site may be an in-vivo or in-vitro target site.

According to some embodiments, there is provided a cationic particle for delivery of a nucleic acid, comprising: a lipid membrane/mixture comprising a cationic lipid, a membrane stabilizing lipid and maleimide conjugated to a targeting moiety; and a nucleic acid encapsulated/carried within the particles. In some embodiments, the targeting moiety is at least partially coating the external surface of the particles. In some embodiments, the targeting moiety is configured to recognize, target and/or bind a specific antigen or epitope of the target leukocyte, thereby allowing targeting of the particle to the target cell.

According to additional embodiments, the present invention provides a composition comprising a plurality of particles, the particles comprising a lipid phase/membrane/mixture comprising a plurality of lipids comprising at least a cationic lipid, a membrane stabilizing lipid and at maleimide derivative, the maleimide derivative is conjugated to a targeting moiety (such as a targeting antibody); and further encapsulate/carry a nucleic acid within the particles. In some embodiments, the particles further include one or more PEG-derivatives.

Reference is now made to FIG. 1A, which is a schematic illustration of preparation of targeted particles, according to some embodiments. As shown, a mixture of lipids, including maleimide moieties/derivatives is mixed with nucleic acid molecules (exemplary shown as siRNA molecules). After formation of the particles (by mixing in a microfluidic mixer), a targeting moiety (shown as a targeting antibody, which is reduced, for example by thilation with DTT), is conjugated to the maleimide moiety, to thereby form the targeted particles.

Figure 1B:
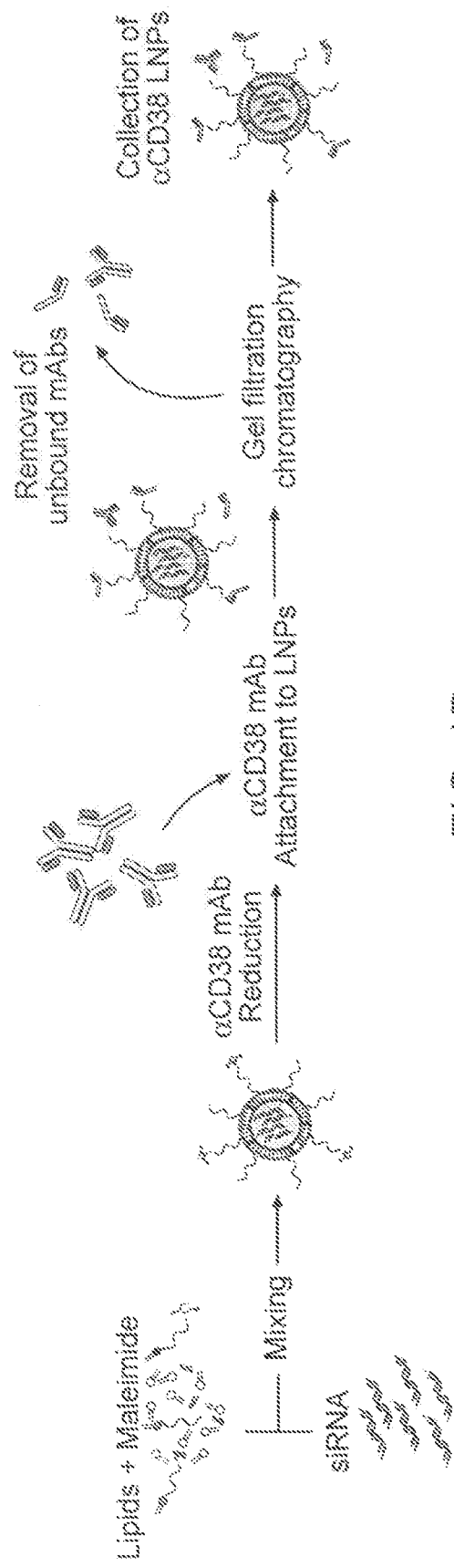
FIG. 1B—Schematic illustration of the preparation of targeted lipid-based particles (LNPs) conjugated to an anti-CD-38 targeting antibody (specifically directed to MCL cells)

Reference is now made to FIG. 1B, which is a schematic illustration of preparation of targeted lipid-based particles (LNPs) conjugated to an anti-CD-38 targeting antibody (for targeting, for example, MCL cells), according to some embodiments. As shown, a mixture of lipids, including maleimide moieties/derivatives is mixed with nucleic acid molecules (exemplary shown as siRNA molecules). After formation of the particles (by mixing in a microfluidic mixer), a targeting antibody (anti-CD38 monoclonal antibody), is reduced (for example by thilation with DTT). The reduced anti-cD38 monoclonal antibody is attached/conjugated to the maleimide moiety, to form the targeted particles. Thereafter, unbound antibodies are removed (for example, by gel-filtration chromatography), to result with the purified anti-CD38 targeted lipids based particles (tLNPs).

According to some exemplary embodiments, the plurality of lipids of the lipid particles may be of natural or synthetic source and may be selected from, but not limited to: cationic lipids, phosphatidylethanolamines, ionized lipids, membrane stabilizing lipids, phospholipids, and the like, or combinations thereof. Each possibility is a separate embodiment.

In some embodiments, the cationic lipid may be selected from ionizable lipid or permanently charged amine cationic lipids.

In some embodiments, the cationic lipids may be synthetic cationic lipids.

In some embodiments, the cationic lipids may be selected from: DLinDMA, DLin-MC3-DMA, DLin-KC2-DMA, Di-oleyl-succinyl-serinyl-tobramycin, Di-oleyl-adipyl-tobramycin, Di-oleyl-suberyl-tobramycin, Di-oleyl-sebacyl-tobramycin, N,N-dimethyl-N',N'-di[(9Z, 12Z)-octadeca-9,12-dien-1-yl] ethane-1,2-diamine, Di-oleyl-dithioglycolyl-tobramycin, monocationic lipid N-[1-(2,3-Dioleoyloxy)]-N,N,N-trimethylammonium propane (DOTAP), BCAT O-(2R-1,2-di-O-(1'Z, 9'Z-octadecadienyl)-glycerol)-3-N-(bis-2-aminoethyl)-carbamate, BGSC (Bis-guanidinium-spermidine-cholesterol), BGTC (Bis-guanidinium-tren-cholesterol), CDAN (N'-cholesteryl oxycarbony 1-3,7-diazanonane-1,9-diamine), CHDTAEA (Cholesteryl hemidithiodiglycolyl tris(amino(ethyl)amine), DCAT (O-(1, 2-di-O-(9'Z-octadecanyl)-glycerol)-3-N-(bis-2-aminoethyl)-carbamate), DC-Chol (3β[N—(N', N'-dimethylaminoethane)-carbamoyl] cholesterol), DLKD (O,O'-Dilauryl N-lysylaspartate), DMKD (O,O'-Dimyristyl N-lysylaspartate), DOG (Diolcylglycerol, DOGS (Dioctadecylamido-glycylspermine), DOGSDSO (1,2-Dioleoyl-sn-glycero-3-succinyl-2-hydroxyethyl disulfide ornithine), DOPC (1,2-Dioleoyl-sn-glycero-3-phosphocholine), DOPE (1,2-Dioleoyl-sn-glycerol-3-phosphoethanolamine, DOSN (Dioleyl succinyl ethylthioneomycin), DOSP (Dioleyl succinyl paromomycin), DOST (Dioleyl succinyl tobramycin), 1,2-Uiolcoyl-3-trimethyl ammoniopropane, DOTMA (N'[1-(2,3-Dioleyloxy)propyl]-N,N,N-trimethylammonium chloride), DPPES (Di-palmitoyl phosphatidyl ethanolamidospermince), DDAB and DODAP, or any combination thereof. Each possibility is a separate embodiment.

In some exemplary embodiments, the cationic lipid may be selected from: DLinDMA, DLin-MC3-DMA, DLin-KC2-DMA, Di-oleyl-succinyl-serinyl-tobramycin, Di-oleyl-adipyl-tobramycin, Di-oleyl-suberyl-tobramycin, N,N-dimethyl-N',N'-di[(9Z, 12Z)-octadeca-9,12-dien-1-yl] ethane-1,2-diamine, Di-oleyl-sebacyl-tobramycin and Di-oleyl-dithioglycolyl-tobramycin. Each possibility is a separate embodiment.

In some exemplary embodiments, the cationic lipid may be selected from:monocationic lipid N-[1-(2,3-Dioleoyloxy)]-N,N,N-trimethylammonium propane (DOTAP), BCAT O-(2R-1,2-di-O-(1'Z, 9'Z-octadecadienyl)-glycerol)-3-N-(bis-2-aminoethyl)-carbamate, BGSC (Bis-guanidinium-spermidine-cholesterol), BGTC (Bis-guanidinium-tren-cholesterol), CDAN (N'-cholesteryl oxycarbony 1-3,7-diazanonane-1,9-diamine), CHDTAEA (Cholesteryl hemidithiodiglycolyl tris(amino(ethyl)amine), DCAT (O-(1, 2-di-O-(9'Z-octadecanyl)-glycerol)-3-N-(bis-2-aminoethyl)-carbamate), DC-Chol (3β[N—(N', N'-dimethylaminoethane)-carbamoyl] cholesterol), DLKD (O,O'-Dilauryl N-lysylaspartate), DMKD (O,O'-Dimyristyl N-lysylaspartate), DOG (Diolcylglycerol, DOGS (Dioctadecylamido-glycylspermine), DOGSDSO (1,2-Dioleoyl-sn-glycero-3-succinyl-2-hydroxyethyl disulfide ornithine), DOPC (1,2-Dioleoyl-sn-glycero-3-phosphocholine), DOPE (1,2-Dioleoyl-sn-glycerol-3-phosphoethanolamine, DOSN (Dioleyl succinyl ethylthioneomycin), DOSP (Dioleyl succinyl paromomycin), DOST (Dioleyl succinyl tobramycin), 1,2-Uiolcoyl-3-trimethyl ammoniopropane, DOTMA (N'[1-(2,3-Dioleyloxy)propyl]-N,N,N-trimethylammonium chloride), DPPES (Di-palmitoyl phosphatidyl ethanolamidospermince), DDAB and DODAP. Each possibility is a separate embodiment.

In some exemplary embodiments, the cationic lipid may be selected from: DLinDMA (1,2-dilinoleyloxy-3-dimethylaminopropane), DLin-MC3-DMA (heptatriaconta-6,9,28, 31-tetraen-19-yl 4-(dimethylamino)butanoate), and DLin-KC2-DMA (2,2-dilinoleyl-4-dimethylaminoethyl-[1,3]-dioxolane). Each possibility is a separate embodiment.

In some exemplary embodiments, the cationic lipid has a pKa in the range of about 6.5-7. In some embodiments, the cationic lipid is selected from, but not limited to: DLinDMA, (with lipid pKa of 6.8), DLin-MC3-DMA (with lipid pKa of 6.44) and DLin-KC2-DMA (with lipid pKa of 6.7), or combinations thereof. Each possibility is a separate embodiment.

In some embodiments, the membrane stabilizing lipids may be selected from, but not limited to: cholesterol, phospholipids (such as, for example, phosphatidylcholine (PC, such as, DSPC (1,2-distearoyl-sn-glycero-3-phosphocholine), DMPC, DPPC, DHPC and DLPC), phosphatidylethanolamine, phosphatidylinositol, phosphatidylserine, phosphatidylglycerol, diphosphatidylglycerols), cephalins, sphingolipids (sphingomyelins and glycosphingolipids), glycoglycerolipids, and combinations thereof. Each possibility is a separate embodiment.

In some embodiments, the Phosphatidylethanolamines may be selected from, but not limited to: 1,2-dilauroyl-L-phosphatidyl-ethanolamine (DLPE), 1,2-Dioleoyl-sn-glycero-3-phosphoethanolamine (DOPE), 1,2-Diphytanoyl-sn-glycero-3-phosphoethanolamine (DPhPE) 1,3-Dipalmitoyl-sn-glycero-2-phosphoethanolamine (1,3-DPPE), 1-Palmitoyl-3-oleoyl-sn-glycero-2-phosphoethanolamine (1,3-POPE), Biotin-Phosphatidylethanolamine, 1,2-

Dimyristoyl-sn-glycero-3-phosphoethanolamine (DMPE), Dipalmitoylphosphatidylethanolamine (DPPE), 1,2-Distearoyl-sn-glycero-3-phosphoethanolamine (DSPE) or combinations thereof. In some embodiments, the Phosphatidylethanolamines may be conjugated to a PEG-Amine derivative. Each possibility is a separate embodiment.

According to some embodiments, the particles (lipid phase thereof), may further include one or more PEG derivatives. In some embodiments, the PEG derivatives may be conjugated to one or more additional molecules, such as, a lipid. In some embodiments, the PEG derivative is selected from, but not limited to: PEG-DMG, cDMA 3-N-(-methoxy poly(ethylene glycol)2000)carbamoyl-1,2-dimyristyloxy-propylamine; PEG-cDSA, 3-N-(-methoxy poly(ethylene glycol)2000)carbamoyl-1,2-distearyloxy-propylamine, DSPE-PEG, PEG-maleimide, DSPE-PEG-maleimide, or combinations thereof. Each possibility is a separate embodiment.

In some embodiments, the maleimide derivative/moiety may be conjugated, attached or linked to a PEG-derivative, which may be by itself conjugated, linked and/or attached to a lipid.

According to some embodiments, the ratio between the various lipids in the particle may vary. In some embodiments, the ratio is a molar ratio. In some embodiments, the ratio is a weight ratio. In some embodiments, each of the lipid groups may be at molar ratio/a weight ratio of about 1%-99%.

According to some embodiments, the weight ratio between the nucleic acid and the lipid mixture may be adjusted so as to achieve maximal biological effect by the nucleic acid on the target site. In some embodiments, the ratio between the nucleic acid and the lipid phase may be 1:1. For example, the weight ratio between the nucleic acid and the lipid phase may be 1:2. For example, the weight ratio between the nucleic acid and the lipid phase may be 1:5. For example, the weight ratio between the nucleic acid and the lipid phase may be 1:10. For example, the weight ratio between the nucleic acid and the lipids phase may be 1:16. For example, the weight ratio between the nucleic acid and the lipid phase may be 1:20. In some embodiments, the weight ratio between the nucleic acid and the lipid phase is about 1:1 to 1:30 (w:w).

In some embodiments, the particles are nanoparticles. In some embodiments, the particles (including the nucleic acid encapsulated within) and the targeting moiety on the surface particles have a particle size (diameter) in the range of about 10 to about 500 nm. In some embodiments, the particles have a particle size (diameter) in the range of about 10 to about 350 nm. In some embodiments, the particles have a particle size (diameter) in the range of about 50 to about 250 nm. In some embodiments, the particles have a particle size (diameter) in the range of about 10 to about 200 nm. In some embodiments, the particles have a particle size (diameter) in the range of about 20 to about 200 nm. In some embodiments, the particles have a particle size (diameter) in the range of about 50 to about 200 nm. In some embodiments, the particles have a particle size (diameter) in the range of about 70 to about 140 nm. In some embodiments, the particles have a particle size (diameter) in the range of about 75 to about 200 nm. In some embodiments, the particles have a particle size (diameter) in the range of about 90 to about 200 nm. In some embodiments, the particles have a particle size (diameter) in the range of about 100 to about 200 nm. In some embodiments, the particles have a particle size (diameter) in the range of about 120 to about 200 nm. In some embodiments, the particles have a particle size (diameter) in the range of about 150 to about 200. In some embodiments, the particles have a particle size (diameter) in the range of about 50 to about 150 nm. In some embodiments, the particles have a particle size (diameter) in the range of over about 10 nm. In some embodiments, the particles have a particle size (diameter) of over about 20 nm. In some embodiments, the particles have a particle size (diameter) of over about 30 nm. In some embodiments, the particles have a particle size (diameter) of over about 40 nm. In some embodiments, the particles have a particle size (diameter) of over about 50 nm. In some embodiments, the particles have a particle size (diameter) of over about 60 nm. In some embodiments, the particles have a particle size (diameter) of over about 70 nm. In some embodiments, the particles have a particle size (diameter) of over about 80 nm. In some embodiments, the particles have a particle size (diameter) of over about 90 nm. In some embodiments, the particles have a particle size (diameter) of over about 100 nm. In some embodiments, the particles have a particle size (diameter) of over about 200 nm. In some embodiments, the particles have a particle size (diameter) of not more than about 500 nm. In some embodiments, the particles (including the nucleic acid encapsulated within) have a particle size (diameter) in the range of about 5 to about 200 nm. In some embodiments, the particles (including the nucleic acid encapsulated within) have a particle size (diameter) in the range of about 70 to about 140 nm. In some embodiments, the particles (including the nucleic acid encapsulated within) have a particle size (diameter) in the range of about 50 to about 60 nm. In some embodiments, the particles (including the nucleic acid encapsulated within) have a particle size (diameter) in the range of about 55 to about 58 nm. In some embodiments, the size is a hydro dynamic diameter.

According to exemplary embodiments, the particles may be comprised of a cationic lipid (such as, for example, DLinDMA, DLinMC3-DMA or DlinKC2-DMA), cholesterol, 1,2-Distearoyl-sn-glycero-3-phosphocholine (DSPC), PEG derivative (such as DMG-PEG) and PEG-maleimide conjugated to a lipid (such as DSPE-PEG-maleimide); at various mol:mol ratios, and further conjugated to a targeting moiety, wherein the targeting moiety is conjugated, linked, attached to the maleimide moiety. For example, the lipid phase may be comprised of: DLinMC3/DSPC/cholesterol/DMG-PEG/DSPE-PEG-Maleimide (mol/mol 50:10:38:1.5:0.5). For example, the lipid phase may be comprised of: DLinMC3-DMA/Chol/DSPC/DMG-PEG/DSPE-PEG-maleimide (mol/mol 50:38:10:1.95:0.05). For example, the lipid phase may be comprised of: DLinKC2-DMA/Chol/DSPC/DMG-PEG/DSPE-PEG-maleimide (mol/mol 50:38:10:1.95:0.05). For example, the lipid phase may be comprised of: DLinKC2-DMA/Chol/DSPC/DMG-PEG/DSPE-PEG-maleimide (mol/mol 45:30:23:1.5:0.5).

According to some embodiments, the lipid phase may comprise about 30-60% (mol:mol) cationic lipids. For example, the cationic lipid(s) may comprise about 40-50% (mol:mol) of the lipid phase.

According to some embodiments, the lipid phase may comprise about 20-70% (mol:mol) membrane stabilizing lipids. For example, the membrane stabilizing lipids may comprise about 40-60% of the lipid phase. In some embodiments, more than one type of membrane stabilizing lipid may be used in the lipid phase. For example, the membrane stabilizing lipid may include cholesterol (being about 30-50% (mol:mol) of the lipid phase), and a phospholipid (such as, for example, DSPC), that may be about 5-15% (mol:mol) of the lipid phase.

According to some embodiments, the lipid phase may comprise about 0.01-3% (mol:mol) of PEG-maleimide (optionally conjugated to a lipid). For example, the PEG-maleimide may comprise about 0.05-0.6% of the lipid mixture.

According to some embodiments, an additional PEG-derivative (conjugated to a lipid) may comprise about 0.5-10% of the lipid phase composition. For example, the additional PEG derivative may comprise about 1.5-3% of the lipid phase.

According to some embodiments, there is provided a method for the preparation of targeted particle(s) for delivery of a nucleic acid to leukocytes, the method comprising one or more of the steps of:
 a) mixing a plurality of lipids, including, cationic lipid, membrane stabilizing lipid and PEG-maleimide conjugated to a phospholipid, in an organic solvent at a desired ratio;
 b) adding nucleic acids to the mixture in a suitable solution at a desired ratio;
 c) mixing the lipid mixture and the nucleic acids in a microfluidic micromixer to form particles;
 d) dialyzing the particles to remove undesired solvents;
 e) incubating the particles with a suitable targeting moiety to generate targeted particles;
 f) removing unconjugated/un-bound targeting moieties, optionally by gel filtration;
 g) filtration of reconstituted t-conjugated particles encapsulating nucleic acid molecules;

According to some exemplary embodiments, there is provided a method for the preparation of targeted particle(s) for delivery of a nucleic acid to leukocytes, the method comprising one or more of the steps of:
 a) mixing a plurality of lipids, including, cationic lipid, membrane stabilizing lipid and PEG-maleimide conjugated to a phospholipid, in an organic solvent at a desired ratio;
 b) adding nucleic acids to the mixture in a suitable solution at a desired ratio;
 c) mixing the lipid mixture and the nucleic acids in a microfluidic micromixer to form particles;
 d) dialyzing the particles to remove undesired solvents;
 e) incubating the particles with reduced targeting antibodies to generate targeted particles;
 f) removing unconjugated antibodies, optionally by gel filtration;
 g) filtration of reconstituted t-conjugated particles encapsulating nucleic acid molecules;

In some embodiments, the lipids are suspended in an acidic aqueous buffer, such as, ethanol. In some embodiments, the nucleic acid is in an acetate buffer solution.

In some embodiments, the nucleic acid may be mixed with the lipid mixture in a microfluidizer mixer to form particles encapsulating/carrying the nucleic acid.

In some embodiments, the targeting moiety may be manipulated prior to interacting with the lipid particles, for example, by reduction. In some exemplary embodiments, when the targeting moiety is an antibody, it reduced by a reducing agent, such as, DTT. In some embodiments, the targeting antibody is incubated with the particles after it has been reduced. In some embodiments, the thiolized targeting antibody is incubated with the particles to form a conjugate with the maleimide moiety.

According to some embodiments, the method for the preparation of the targeted particles may include various modifications to finely adjust the components of the composition, as well as the ratio between the components, so as to obtain the most effective composition. The modifications may include, for example, such parameters as, but not limited to: the specific lipids used for the formation of the lipid composition, the ratio between the lipids of the lipid compositions, the identity of the nucleic acid to be encapsulated, the ratio between the nucleic acid and the lipid composition, the specific targeting moiety used, the pH at which reactions are performed, the temperatures at which reactions are performed, the conditions at which the reactions are formed, the time length of various steps, and the like, or any combination thereof.

According to some embodiments, the method for the preparation of the particles of the present invention may beneficially result in uniformly distributed particle size.

According to some embodiments, the particles formed by the methods of the present invention may be lyophilized or dehydrated at various stages of formation.

According to some embodiments, the targeted particles of the present disclosure can be used in the treatment of various leukocytes-associated pathological conditions.

According to some embodiments, the particles may be administered as is. In some embodiments, the particles may be administered in a solution. In some embodiments, the particles may be formulated to a suitable pharmaceutical composition to be administered by any desired route of administration. Exemplary routes of administration include such routes as, but not limited to: topical, oral or parenteral. Depending on the intended mode of administration, the compositions used may be in the form of solid, semi-solid or liquid dosage forms, such, as for example, tablets, suppositories, pills, capsules, powders, liquids, suspensions, or the like, preferably in unit dosage forms suitable for single administration of precise dosages. The pharmaceutical compositions may include the cationic particles, a pharmaceutical acceptable excipient, and, optionally, may include other medicinal agents, pharmaceutical agents, carriers, adjuvants, and the like. It is preferred that the pharmaceutically acceptable carrier be one which is inert to the nucleic acid encapsulated within the particles and which has no detrimental side effects or toxicity under the conditions of use. In some embodiments, the administration is localized. In some embodiments, the administration is systemic.

In some embodiments, injectable formulations for parenteral administration can be prepared as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, and the like. Aqueous injection suspensions may also contain substances that increase the viscosity of the suspension, including, for example, sodium carboxymethylcellulose, sorbitol, and/or dextran. Optionally, the suspension may also contain stabilizers. The parenteral formulations can be present in unit dose or multiple dose sealed containers, such as ampules and vials, and can be stored in a freeze-dried (lyophilized) condition requiring only the addition of the sterile liquid carrier, such as, for example, water, for injections immediately prior to use. In some embodiments, parenteral administration includes intravenous administration.

In other embodiments, for oral administration, a pharmaceutically acceptable, non-toxic composition may be formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include solutions, suspensions, tablets, dispersible tablets, pills, capsules, powders, sustained release formulations and the like. Formulations suitable for oral administration can consist of liquid solutions such as effective amounts of the compound(s) dissolved in diluents such as water, saline, or orange juice; sachets, lozenges, and troches, each containing a predetermined amount of the active ingredient as solids or granules; powders, suspensions in an appropriate liquid; and suitable emulsions. Liquid formulations may include diluents such as water and alcohols, (such as, for example ethanol, benzyl alcohol, and the polyethylene alcohols), either with or without the addition of a pharmaceutically acceptable surfactant, suspending agents, or emulsifying agents.

In determining the dosages of the particles to be administered, the dosage and frequency of administration may be selected in relation to the pharmacological properties of the specific nucleic acids encapsulated within the particles.

In some embodiments, there is provided a composition, which include a plurality of particles, wherein the various particles may encapsulate a similar or different nucleic acid molecule (such as a similar or different type of molecule, a similar or different sequence of the nucleic acid, and the like, or combinations thereof).

In some exemplary embodiments, particles comprising a nucleic acid, such as, for example, siRNA, miRNA, shRNA, anti-sense RNA, and the like, may be used in the treatment of various leukocyte-associated conditions, depending on the identity of the nucleic acid, the specific target leukocyte, and the like. In some embodiments, the nucleic acid encapsulated within the particles may be a nucleic acid capable of inducing silencing of a target gene. In some embodiments, the target gene may be any gene, the expression of which is related to the condition to be treated. In some embodiments, the target gene may be a gene selected from, but not limited to: growth factors (such as EGFR, PDGFR), genes related to angiogenesis pathways (such as VEGF, Integrins), genes involved in intracellular signaling pathways and cell cycle regulation (such as PI3K/AKT/mTOR, Ras/Raf/MAPK, PDK1, CHK1, PLK1, Cyclins, STAT1, STAT3, MCL1, CKAP5, RRM1, SF3A1 and CDK11B). In some embodiments, a combination of nucleic acids, each having one or more targets may be encapsulated within the particles. Each possibility is a separate embodiment.

According to some embodiments, exemplary leukocyte-associated conditions that may be treated by the targeted particles may be selected from, but not limited to: various types of cancer, various infections (such as, for example, viral infection, bacterial infection, fungal infection, and the like), autoimmune diseases, neurodegenerative diseases, inflammations, and the like.

In some exemplary embodiments, the targeted particles comprising a nucleic acid (such as, siRNA or miRNA, shRNA, anti-sense RNA, modified mRNA, guided RNA, or the like), may be used for the treatment of cancer.

In some embodiments, cancer is a disorder in which a population of cells has become, in varying degrees, unresponsive to the control mechanisms that normally govern proliferation and differentiation. In some embodiments, the cancer is a blood cancer. Non-limiting examples of blood cancers are lymphoma, leukemia and multiple myeloma. Lymphomas may be divided into two categories: Hodgkin lymphoma and non-Hodgkin lymphoma. Most non-Hodgkin lymphomas are B-cell lymphomas, that grow quickly (high-grade) or slowly (low-grade). There are about 14 types of B-cell non-Hodgkin lymphomas, including, but not limited to: Burkitt lymphoma, chronic lymphocytic leukemia/small lymphocytic lymphoma (CLL/SLL), diffuse large B-cell lymphoma, follicular lymphoma, marginal-zone B-cell lymphoma, Nodal marginal zone B cell lymphoma (NMZL), Splenic marginal zone lymphoma (SMZL), Intravascular large B-cell lymphoma, Primary effusion lymphoma, Lymphomatoid granulomatosis, Primary central nervous system lymphoma, ALK-positive large B-cell lymphoma, Plasmablastic lymphoma and mantle cell lymphoma (MCL). Each possibility is a separate embodiment. T-cell lymphomas include such cancers as, but not limited to: Peripheral T-cell lymphoma, Anaplastic large cell lymphoma, Angioimmunoblastic Lymphoma, Cutaneous T-cell lymphoma, Adult T-cell Leukemia/Lymphoma (ATLL), Blastic NK-cell Lymphoma, Enteropathy-type T-cell lymphoma, Hematosplenic gamma-delta T-cell Lymphoma, Lymphoblastic Lymphoma, Nasal NK/T-cell Lymphomas, Treatment-related T-cell lymphomas, and the like. Each possibility is a separate embodiment.

In some exemplary embodiments, the nucleic acid that may be used for the treatment of cancer are directed against a target gene, which is involved in the regulation of cell cycle. In some exemplary embodiments, the target gene may be Polo-like Kinase 1 (PLK), Cyclin D1, CHK1, Notch pathway genes, PDGFRA, EGFRvIII, PD-L1, RelB, STAT1, STAT3, MCL1, CKAP5, RRM1, SF3A1 and CDK11B, and the like, or combinations thereof. Each possibility is a separate embodiment.

According to some embodiments the particles disclosed herein are particularly useful to specifically target and silence gene expression in leukocytes cells, such as, B-cells and T-cells. In some embodiments, the particles may be administered systemically.

In some exemplary embodiments, the leukocytes cells are CD4+ T cells. As exemplified herein, the targeted NLPs can effectively silence an exemplary gene, CD45, in CD4+ T cells at much lower doses (mg/Kg body) than any non-targeted system to leukocytes. In some embodiments, this silencing is detected in all the major tissues that harbor T cells (blood, spleen, bone marrow and inguinal lymph nodes). In some embodiments, CD45 silencing was restricted to the CD4+ T cells and was not observed in other lymphocyte subsets. In some embodiments, the decrease in CD45 expression is at the protein and/or mRNA levels.

According to some embodiments, there is a CD4+ T cell subset in which uptake of the tLNPs was less efficient. According to some embodiments, and as exemplified herein two distinct CD4+ T cells populations that differ in their tLNPs uptake ability can be identified. Distinct population of CD4 T cells (CD4low) was permissive for tLNPs internalization followed by siRNA cytoplasmic diffusion, while the remaining of the CD4+ cells harbor tLNPs (CD4high) on their surface without proceeding to internalization.

According to some embodiments, tLNPs internalization and not endosome escape is a central event that define tLNPs efficacy. According to some embodiments, the internalization of the tLNPs take place within a short time (for example, in the range of 30-120 minutes) post systemic administration of the particles.

According to some embodiments, there is provided a method for the treatment of leukocyte-related cancer, comprising the step of administration to a subject in need thereof the targeted particles of the present disclosure or a pharmaceutical compositions comprising the same. In some embodiments, there is provided the use of the particles of the present disclosure or a pharmaceutical composition comprising the same, for the treatment of leukocyte-related cancer. In some embodiments, the particles encapsulate a nucleic acid capable of inducing growth inhibition or killing of the cancer cells, thereby treating the leukocyte-related cancer.

According to some embodiments and as exemplified herein, Mantle Cell Lymphoma (MCL) is used herein as a prototypic blood cancer for demonstrating the targeting and therapeutic abilities of the particles disclosed herein. MCL is an aggressive B-cell lymphoma that overexpresses cyclin D1 with relatively poor prognosis. Thus, down-regulation of cyclin D1 using RNA interference (RNAi) can be used as a therapeutic approach to this malignancy. According to some embodiments, and as exemplified herein, targeted lipid-based nanoparticles (LNPs) coated with anti-CD38 monoclonal antibodies are specifically targeted to and taken up by human MCL cells in the bone marrow of xenografted mice. According to some embodiments, when carrying siRNAs against cyclin D1, CD38-targeted LNPs induce gene silencing in MCL cells to result in prolonged survival of tumor-bearing mice with no observed adverse effects.

According to some embodiments, there is provided a method of treating MCL, by administering an effective amount of the targeted particles of the present invention (or a pharmaceutical composition comprising the same), whereby the targeted lipid based particles are coated (conjugated) to an anti-CD38 antibody (such as a monoclonal antibody). In some embodiments, the particles encapsulate/carry a nucleic acid molecule capable of killing or inhibit growth of the MCL cells. In some embodiments, the nucleic acid molecule encapsulated within the particles is an siRNA. In some embodiments, the siRNA is directed against a cell cycle regulator. In some embodiments, the siRNA is directed against cyclin D1.

According to some embodiments, there is provided a use of the targeted particles of the present invention for treating MCL, the particles (or a pharmaceutical composition comprising the same) are coated/conjugated to an anti-CD38 antibody, such as, an anti-CD38 monoclonal antibody. In some embodiments, the targeted particles carry/encapsulate an siRNA molecule directed against a cell cycle regulator, such as, Cyclin D1.

According to some embodiments, and as exemplified herein, CD38 is a suitable target for antibody-mediated delivery of therapeutic siRNAs to MCL. LNPs-siRNA coated with an anti-CD38 monoclonal antibody (αCD38 mAb) exhibit specific MCL binding in vitro (in MCL cell lines and MCL primary lymphomas) and in vivo (in mice xenografted with a human MCL cell line). CD38-targeted LNPs (αCD38-LNPs) entrapping siRNA against cycD1 (siCycD1) are specifically taken up by MCL xenografts. αCD38-LNPs-siCycD1 induced gene silencing and suppressed tumor cell growth in vitro, and prolonged the survival of MCL-bearing mice.

According to some embodiments, αCD38-LNPs-siRNA can be used for treating MCL and other CD38-expressing hematological malignancies. According to some embodiments, there is provided a method of treating CD38-expressing hematological malignancies, the method comprising administering the αCD38-LNPs-siRNAs or pharmaceutical compositions comprising the same to a subject in need thereof.

According to some embodiments, αCD38-LNPs-siRNA that encapsulate siRNAs against cycD1 can prolong the survival subjects afflicted with MCL.

According to some embodiments, to achieve specificity for targeting MCL cells, the LNPs can be coated with an anti-CD38 mAb (such as, clone THB-7). In some embodiments, such mAb recognizes the surface protein CD38, which is found on immature leukocyte precursors, but overexpressed in MCL tumor cells and other B-cell hematological malignancies, such as in CLL (where it correlates with poor prognosis) and multiple myeloma. According to some embodiments, the THB-7 αCD38 mAbs can be used as a MCL-targeting moiety without displaying significant anti-tumor activity by themselves. In some embodiments, an anti-CD38 antibody which displays an anti-tumor effect by itself, may be used as a targeting moiety for the particles, in which case, a synergistic effect on the targeted cells may be observed. In some embodiments, an anti-CD38 antibody can mediate active delivery of siRNAs into the cytoplasm of targeted cells.

In some embodiments, αCD38-LNPs-siRNA may be internalized and induce gene silencing in various CD38-implicated diseases.

In some embodiments the αCD38-antibody is a THB-7 monoclonal antibody.

According to some embodiments, systemic administration of targeted lipid-based nanoparticles coated with antibodies targeting the CD38 cell marker can specifically target (bind) MCL cells and induce an inhibitory effect within the cells, by the inhibitory siRNA encapsulated within the particles. In some embodiments, the particles can provide protection in vivo and in-vitro) to the nucleic acid molecules encapsulated therein.

According to some embodiments, the disclosed targeted particles exhibit a safety profile, as repeated systemic administration did not affect body weight.

According to some embodiments, the targeted particles disclosed herein are particularly useful for MCL cells, other lymphomas and most hematopoietic cells, which are dispersed throughout the body and are not easily transfected by conventional lipid-based transfection reagents. The targeted particles disclosed are scalable, safe, efficient and allow high selectivity to subsets of leukocyte cells, in-vivo.

According to some embodiments, matching of the appropriate targeting moiety to the surface receptor expressed on the target cells can be performed to determine the targeting specificity of the particles. For example, it is possible to use different antibodies as targeting moieties for MCL cells and other B cell malignancies (including those that do not express the CD38 protein). In some embodiments, when matching the appropriate targeting moiety to the target cell, consideration may be taken as some receptors might cluster on the cell surface and induce an outside-in signaling event that could lead to proliferation, rather to inhibition of cellular growth.

According to some embodiments, the particles disclosed herein may be used as a diagnostic platform or a research tool for using in vivo gene knockdown to study leukocyte (such as, B cells and T-cells) biology.

In some embodiments, when treating a related condition, administration of the targeted particles carrying a nucleic acid may be performed in combination with one or more additional treatments. For example, when treating cancer, such combination therapy may be used to increase tumor susceptibility to chemotherapy and irradiation.

In some embodiments, for treating cancer, silencing nucleic acids (such as, siRNA, miRNA, shRNA, and the like) that target genes such as, but not limited to: Cyclins, MGMT, Cx43, HeR1/EGF-R46, VEGF44, BCL-2, STAT1, STAT3, MCL1, CKAP5, RRM1, SF3A1, CDK11B Toll-like receptors, and the like, may be used and may further provide synergistic responses.

In some embodiments, when treating a condition, repeated administration of the targeted particles may be performed, wherein the dosages administered and the composition of the nucleic acid encapsulated therein may be identical, similar or different. In some embodiments, the administration may be prolong (such as over the course of 1-120 hours).

The term comprising includes the term consisting of.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods:
Materials

Lipids: All lipids used for LNPs production (Cholesterol, DSPC and DSPE PEG-Mal) were purchased from Avanti Polar lipids (USA). Dlin-MC3-DMA was synthesized according to Cohen et. al.

Monoclonal antibodies: FITC anti-mouse CD8 (clone 5H10-1), PerCP anti-mouse CD3 (clone 145-2C11), PE anti-mouse CD19 (clone 6D5) and PE anti-mouse CD4 (clone GK1.5) were purchased from BioLegend. Anti-mouse CD4 (clone YTS.177) and Rat IgG2a isotype (clone 2A3) were purchased from bioxcell. monoclonal antibodies THB-7 (mouse IgG1 anti-hCD38) and MOPC-21 (mouse IgG1 isotype ctrl) were purchased from BioXcell (USA).

Secondary antibody Alexa Flour® 647 AffinityPure F(ab')2 fragment Donkey anti-rat IgG (H+L) (minimal cross-reaction to Mouse) was purchased from Jackson ImmunoResearch Laboratories.

siRNA molecules were designed and screened by Alnylam Pharmaceuticals (USA).

Chemically modified siRNAs sequences:

```
CD45 siRNA:
Sense strand:
                                        (SEQ ID NO: 1)
cuGGcuGAAuuucAGAGcAdTsdT Anti-Sense strand:
                                        (SEQ ID NO: 2)
UGCUCUGAAAUUcAGCcAGdTsdT Luc siRNA (siLuc):
Sense strand:
                                        (SEQ ID NO: 3)
cuuAcGcuGAGuAcuucGAdTsdT Anti-Sense strand:
                                        (SEQ ID NO: 4)
UCGAAGuACUcAGCGuAAGdTsdT Alexa-647-labeled siRNA possessed the same
sequence as siLuc.
Cyclin D1 siRNA (siCycD1)
Sense strand
                                        (SEQ ID NO: 5)
GUAGGACUCUCAUUCGGGATT
```

2'-OMe modified nucleotides are in lower case, and phosphorothioate linkages are represented by "s".

Cells: Granta-519 and Jeko-1 cells were purchased from DSMZ (Germany) and TK-1, Mino and Rec-1 cells were purchased from the American Type Culture Collection (ATCC) and cultured as recommended.

Preparation of Lipid-Based Nanoparticles (LNPs) Entrapping siRNAs

LNPs were prepared by using microfluidic micro mixture (Precision NanoSystems, Vancouver, BC, Canada) as described by Cohen et. al. One volume of lipid mixtures (Dlin-MC3-DMA, DSPC, Chol, DMG-PEG and DSPE-PEG Mal at 50:10:38:1.5:0.5 mole ratio or Dlin-MC3-DMA, Chol, DSPC, DMG-PEG, DSPE-PEG-Mal at 50:38:10:1.95: 0.05 molar ratio, 9.64 nM total lipid concentration) in ethanol and three volumes of siRNA (1:16 w/w siRNA to lipid) containing acetate buffer solutions were mixed by using dual syringe pump (Model 5200, kD Scientific, Holliston, MA) to drive the solutions through the micro mixer at a combined flow rate of 2 mL/minute (0.5 mL/min for ethanol and 1.5 mL/min for aqueous buffer). For labeled LNPs, 10% of Alexa-647 labeled siRNA were incorporated. For Cy5 labeled particles, 10% Cy5 labeled non-targeted siRNA was used. The resultant mixture was dialyzed against PBS (pH 7.4) for 16 h to remove ethanol.

Conjugation of Targeting Antibodies with LNPs (tLNPS)

CD4 IgG (clone YTS 177) or Isotype mAbs (clone X63) were reduced with 1 mM DTT for 30 min at room temperature. THB-7, isotype mAbs (MOPC-21) were reduced with DTT (1 mM and 5 mM, respectively) for 30 minutes shaking in 37° C. DTT was removed by using 7K cut off Zeba spin desalting columns (Thermo, USA) according to manufacturer protocol.

The thiolized mAbs were incubated with the Maleimide functionalized LNPs for 1-2 h in gentle shaking at room temperature and optionally overnight at 4° C.

Removal of unconjugated mAbs was performed by loading the LNPs on gel filtration chromatography columns containing sepharose CL-4B or CL-6B beads (Sigma-Aldrich, USA) with phosphate buffer saline (PBS) as a mobile phase. The beads-column was washed with 0.1M NaOH and readjusted with PBS prior to sample loading. The mAbs-LNPs-siRNA were reconcentrated via 10 k or 100 k Amicon Ultra-4 tubes (Millipore, USA) and optionally filtered through a 0.2 m membrane (Sartorius, Germany).

Size, ζ-Potential and Ultrastructure Analysis of αCD38-LNPs-siRNA

LNPs size distribution and ζpotential were determined by dynamic light scattering using a Malvern nano ZS ζ-sizer (Malvern instruments, UK). For size measurements, LNPs were diluted 1:20 in PBS. All utilized samples showed a polydispersity index (PDI) lower than 0.2. For ζ potential measurements, LNPs were diluted 1:200 in DDW. Size and shape of LNPs were analyzed by transmission electron microscopy (TEM). LNPs in PBS were placed on a formvar/carbon coated copper grid, air-dried and stained with 2% aqueous uranyl acetate. The analysis was performed with a Philips Tecnai F20 field emission TEM operated at 200 kV (USA). In some cases, as indicated, size and zeta potential measurements were performed in water.

Transmission Electron Microscopy (TEM) Analysis

A drop of aqueous solution containing LNPs (with or without mAbs) were placed on the carbon coated copper grid and dried. The morphology of LNPs was analyzed by Joel 1200 EX (Japan) transmission electron microscopy.

Confocal Microscopy Analysis:

One hour post administration of tLNPs, splenocytes were collected as mentioned above and stained with Hoechst (nucleus) and Calcein (Cytoplasm) labeling followed by anti-CD4-PE for membrane staining. Cells were washed and images were taken by Nikon C2 (Nikon Instruments inc., USA) confocal microscopy.

Dot Blot Analysis

Several concentration of Rat anti-CD4 (clone YTS.177) along with LNPs, tLNPs and IsoLNPs were blotted on nitrocellulose membrane. After blocking in 5% low-fat milk, the membrane was incubated with AffiniPure F(ab')$_2$ Fragment ANTI-RAT conjugated to Horseradish Peroxidase (Jackson immunoResearch) for 30 min in RT. ECL (Thermo Scientific Pierce) was used as a substrate solution.

Cell Sorting and qPCR

Five days after tLNPs (siCD45) were injected and splenocytes were isolated and stained with anti-CD4 PE and anti-CD45 AF647. As a control, mock treated splenocytes were stained with anti-CD4 PE. CD4$^+$, CD45$^{low}$ population from tLNP treated mice was collected CD4$^+$ cells were collected from mock mice as a control with FACSARIA (BD). mRNA was isolated using EZ-RNA (Biological industries, Israel) and cDNA was prepared using cDNA Synthesis kit (quanta biosciences) mouse PPIB was used as endogenous control. Primers sequence: mPPIB FW: 5' CCA TCG TGT CAT CAA GGA CTT C 3' (SEQ ID NO: 6); mPPIB Rev: 5' GAT GCT CTT TCC TCC TGT GCC 3' (SEQ ID NO: 7); mCD45 FW: 5' TCT TAC ACC ATC CAC TCT GGG C 3' (SEQ ID NO: 8); mCD45 Rev: 5' GCT TCG TTG TGG TAG CTA TGG TT 3' ((SEQ ID NO: 9).

Quantitative Real-Time PCR

Total RNA was isolated using EZ-RNA kit (Biological Industries, Israel) and cDNA was generated with qScript™ cDNA Synthesis Kit (Quanta, MD, USA) according to the manufacturers' instructions. qRT-PCR was performed with Fast SYBR® Green Master Mix and the ABI StepOnePlus™ instrument (Life Technologies). Expression of cyclins was normalized to the two "house-keeping" genes eIF3a & eIF3c using the multiple endogenous controls option. This option allows the software to treat all endogenous controls as a single population, and calculates the experiment-appropriate mean to establish a single value against which the target of interest is normalized. The primers used for amplification are listed below (5' to 3'):

```
CCND1
F:
                                       (SEQ ID NO: 10)
GAGGAGCCCCAACAACTTCC;

R:
                                       (SEQ ID NO: 11)
GTCCGGGTCACACTTGATCAC.

CCND2
F:
                                       (SEQ ID NO: 12)
CGCAAGCATGCTCAGACCTT;

R:
                                       (SEQ ID NO: 13)
TGCGATCATCGACGGTGG.

CCND3
F:
                                       (SEQ ID NO: 14)
CTGACCATCGAAAAACTGTGCAT;

R:
                                       (SEQ ID NO: 15)
ACCTCCCAGTCCCGCAA.

eIF3a
F:
                                       (SEQ ID NO: 16)
TCCAGAGAGCCAGTCCATGC;

R:
                                       (SEQ ID NO: 17)
CCTGCCACAATTCCATGCT.

eIF3c
F:
                                       (SEQ ID NO: 18)
ACCAAGAGAGTTGTCCGCAGTG;

R:
                                       (SEQ ID NO: 19)
TCATGGCATTACGGATGGTCC.
```

Electroporation 1 nmole of each the siRNA duplexes (siLuc or siCycD1) were electroporated into 10×10$^6$ Granta-519 or Jeko-1 cells using the Amaxa 4D-nuclefactor system (CM-119 program, SF solution).

In Vitro Cellular Uptake

Freshly isolated spelnocytes were incubated for 30 min at 4° C. with tLNPs (siCy5) followed by washing with PBS and incubation for 30 min at 37° C. to allow internalization. After, cells were stained with anti-CD4 PE and anti CD8-FITC. Cells were then analyzed by Nikon confocal microscope.

In Vivo tLNPs Biodistribution

Mice were intravenously injected with tLNPs (siCy5) at 1 mg/kg siRNA per body weight of mouse. After one hour mice were sacrificed to collect blood, spleen, lymph nodes and bone marrow cells.

Isolation of Lymphocytes: Blood were collected in heparin coated collection tubes and the leukocytes isolated by density centrifugation using ficoll paque plus (GE healthcare). Single cell suspensions of splenocytes were prepared by mincing of spleens and passing through a 70 μm cell strainer (BD bioscience). RBCs were lysed using ACK lysis buffer and the resulting cells were resuspended in PBS. Inguinal lymph nodes were isolated and minced to make single cell suspension. Cells were washed twice with PBS followed by passing through a 70 um cell strainer. Cells were stained with a secondary Alexa 647 conjugated anti-Rat Fc antibody at 4° C. for 30 min; tLNPs were detected on the surface of the cells by Alexa 647-anti-Rat Fc and/or by Cy5. Cells were then washed with PBS containing 1% FBS and incubated with labeled anti-CD4, CD8, and CD3 antibodies for 30 min at 4° C. Cells were washed and analyzed on a Becton Dickinson FACScalibur flow cytometer with CellQuest software (Becton Dickinson, Franklin Lakes, NJ). Data analysis was performed using FlowJo software (Tree Star, Inc., OR, USA). In addition, cells were imaged on a Nikon confocal microscope.

In Vivo Silencing 8-6 weeks old C57BL6/J mice were obtained from the Animal Breeding Center, Tel Aviv University (Tel Aviv, Israel). All animal protocols were approved by the Tel Aviv Institutional Animal Care and Use Committee. Mice were maintained and treated according National Institutes of Health guidelines. tLNPs or isotype LNPs containing siRNA against CD45 or luciferase were injected intravenously (1 mg/kg siRNA). Mice were euthanized after 5 days and organs were collected for further analysis.

In Vivo Immune Activation

LNPs were injected intravenously into C57BL mice. Lipopolysaccharide (LPS, Sigma) at a concentration of 1 mg/mL (100 µL) was used as a positive control. Blood was collected 2 hr after injection. Serum was separated and stored at −80° C. prior to cytokine analysis. Serum samples were analyzed for cytokine levels according to manufacturer protocol using the Milliplex® MAP kit (Millipore). The quantification was done based on standard curves for each cytokine.

In Vitro Binding Experiments

THB-7 (antiCD38) mAb was labeled with Alexa Fluor(R) 647 protein labeling kit (Invitrogen, USA). Binding of the labeled mAb to MCL cell lines was assessed by flow cytometry (BD FACScalibur, USA, with CellQuest software for data collection and FlowJo software for data analysis). To determine the specific binding of αCD38-LNPs-siRNA, MCL cell lines expressing GFP and murine T-lymphoma TK1 cell line ($0.5 \times 10^6$ each) were incubated together on ice with either 1% fetal calf serum PBS or with the buffer including 1 µg of free αCD38 mAb. After 15 minutes, αCD38-LNPs-siRNA with labeled siRNA were added (0.5 g total siRNA) for 30 additional minutes. Cells were collected for flow cytometry analysis after 3 rounds of PBS wash. Cell populations were separately gated based on GFP fluorescence.

In Vitro Internalization Experiments $0.5 \times 10^6$ Granta cells were incubated in 50 µL of 1% serum PBS on 4 degrees with alexa-647 αCD38 or isotype control mAbs for 10 minutes and then incubated for 2 h at 37° C. (5% CO2). Then, cells were washed twice, stained with PE-hCD20 mAbs (Biolegend, 302306) for 30 minutes on ice, washed and subjected to confocal microscopy analysis. For assessing the internalization of αCD38-LNPs-siRNA, $0.5 \times 10^6$ Granta cells were incubated in 50 µL of 1% serum PBS on ice with αCD38-, isotype- or uncoated siRNA-LNPs including labeled siRNA (500 ng of total siRNA). After 10 minutes, cells passed through 3 rounds of PBS wash and were re-incubated in fresh medium for 4 h at 37° C. (5% CO2). Then, cells were washed, stained with PE-hCD20 mAbs for 30 minutes on ice, washed and subjected to confocal microscopy analysis. All pictures were obtained on live cells using the Nikon Eclipse C2 configured with NI-E microscope and processed with NIS-elements software using X40 objective magnification (Nikon, Japan).

In Vitro Gene Silencing $0.3 \times 10^6$ Granta-519 or Jeko-1 cells were placed in tissue culture 24-wells plates with 0.5 mL of full medium. αCD38-LNPs-siCycD1 or αCD38-LNPs-siLuc were added to the wells (2 µg of siRNA for each condition). After 18 h incubation in standard culture conditions, cells were washed 3 times and re-incubated in fresh medium in culture conditions. 48 h following initial exposure to treatments, cells were collected for cycD1 protein quantification, mRNA quantification or cell cycle measuring. cycD1 intracellular staining was performed according to the BD Pharmingen™ Transcription Factor Buffer set instructions using rabbit anti human cycD1 monoclonal antibody (Cell marque, 241R-16) or isotype control (Jackson ImmunoResearch, 011-000-003) at 0.68 µg/mL. Cells were washed and incubated with 2 µg/mL of Alexa647 Donkey anti-rabbit antibody (Jackson ImmunoResearch, 711-605-152) for 30 minutes at 4° C., washed twice and analysed by flow cytometry. The geometric mean of detected Alexa Fluor®-647 fluorescence intensity for at least 5000 cells was used as the compared value for each sample. cycD1 relative expression for each treatment group was derived from the quotient of the value of cycD1 staining divided by the value of isotype ctrl staining.

Cell Cycle Studies

The transfected cells were washed with ice-cold PBS, and fixed with 70% ethanol for 1 h. Then, the cells were washed twice with cold PBS and incubated for 10 min at 37° C. in 250 µL PBS with 10 µg/mL propidium iodide (PI), 2.5 µg/mL DNase-free RNase A (Sigma, USA) and 0.01% Triton-X. PI fluorescence was assessed by flow cytometry. Analyzes by FlowJo™ were performed on t least 9000 cells per samples after gating out debris and cell duplets based on the FL2-Area/FL2-Width channels. Cell cycle distributions were obtained via the application of the Dean-Jett-Fox model on gated cells with RMS scores ranging between 1.5 and 2.5.

Ex Vivo Binding with Human MCL Primary Samples

Peripheral blood samples were obtained from MCL patients treated at the Rabin medical center, (Petah Tikva, Israel) and the Chaim Sheba Medical Center at Tel Hashomer, (Ramat Gan, Israel) in accordance with institutional review board-approved informed consent. Mononuclear cells were extracted from full blood samples using Ficoll-Paque™ PLUS (GE Healthcare, UK). $1 \times 10^6$ of cells from the primary sample were incubated with targeted LNPs and free competing αCD38 mAb as described in the in vitro binding experiments. After 3 rounds of wash, cells were stained with CD19 (Biolegend, 302219) and CD45 (Biolegend, 304008) mAbs for 30 minutes on ice. Membranal staining was used during analysis to separate B-lymphocytes (CD19+/CD45+) from non-B leukocytes populations (CD19−/CD45+) while assessing for siRNA fluorescence.

Human MCL Xenograft Mouse Model

To enable easier identification of the MCL cells in vivo, Granta-519 cells were stably infected with pTurbo-GFP retroviral particles (kindly supplied by Prof. Eran Bacharach). The infected cells were sorted according to their GFP expression, and the highest GFP population (Granta-GFP) was collected and grew.

For modeling MCL in vivo, Female C.B-17/IcrHsd-Prkdcscid mice were purchased from Harlan laboratories (Jerusalem, Israel). The mice were housed and maintained in laminar flow cabinets under specific pathogen-free (SPF) conditions in the animal quarters of Tel Aviv University and in accordance with current regulations and standards of the Israel Ministry of Health. All animal protocols were approved by Tel Aviv University Institutional Animal Care and Use Committee.

$2.5 \times 10^6$ Granta-519 or Granta-GFP cells were intravenously injected into 8 weeks old mice. Mice were monitored daily and killed when disease symptoms appeared (15% reduction in body weight or hind leg paralysis). Different tissues and organs (liver, kidney, lungs, spleen, blood, bone marrow, and if existed, solid tumor) were collected with respect to the different experiments, and processed into single cell suspensions. To identify the MCL cells, cell suspensions were analyzed by flow cytometry, using PE mouse anti human CD45 antibody, PE or alexa 647 mouse anti human CD20 (Biolegend, 302318) antibodies and/or GFP expression. Femour bones were fixed, sliced, decalcified and stained with H&E as described before (38).

In Vivo Binding of αCD38 mAb

MCL xenograft mice were intravenously injected with 30 µg of Alexa-647 labeled αCD38 or isotype control mAbs at day of hind-leg paralysis appearance. 2 h later, mice were scarified and liver, kidneys, lungs, spleen and bone marrow were harvested and processed into single cell suspensions. αCD38 fluorescence on cells was assessed by flow cytometry.

In Vivo Binding of Targeted LNPs

At day 24 post tumor injection, either saline, isotype- or αCD38-LNPs-siCycD1 including labeled siRNA (1.25 mg siRNA/kg body) were administered i.v. via the tail vein. After 2 h, mice were sacrificed and cells from the bone marrow extracted. Single cell suspensions were prepared by passing the cells through 70 m cell strainers (BD) and washing with PBS. Cells were stained with Alexa Fluor®-488-hCD20 (Biolegend, 302316) and PE-mCD45 (Biolegend 103106) mAbs for 30 minutes and washed prior to analysis. Human MCL cells (GFP+/hCD20+/mCD45−) and murine cells (GFP−/hCD20−/mCD45+) were gated separately and assessed for siRNA fluorescence. The cells from the mock-treated mouse were used as a baseline for negative fluorescence, while cells in other groups were considered positive to siRNA fluorescence if exhibiting higher values than the 99th percentile's value of mock.

Survival Experiment

The survival experiment was performed in Charles Rivers Laboratories, Tranent, Scotland, in accordance with local ethical requirements. 30 MCL xenograft mice were divided into 3 treatment groups: untreated (mock), αCD38-LNPs-siLuc and αCD38-LNPs-siCycD1. The different treatments (1 mg siRNA/kg body) were injected via retro-orbital route 9 times (days 5, 8, 12, 15, 19, 22, 26, 29, 33). Mice displaying loss of 15% bodyweight or limb paralysis were euthanized.

Statistical Analysis

In experiments with multiple groups, one-way ANOVA with Bonferroni correction was sued. For the comparison of two experimental groups, two-tailed Student's t test was used. Differences between or among groups are labeled as n.s. for not significant, * for p<0.05,  for p<0.005 and * for p<0.0005. A value of P<0.05 was considered statistically significant. Analyzes were performed with Prism 6 (Graphpad Software).

Figure 2A:
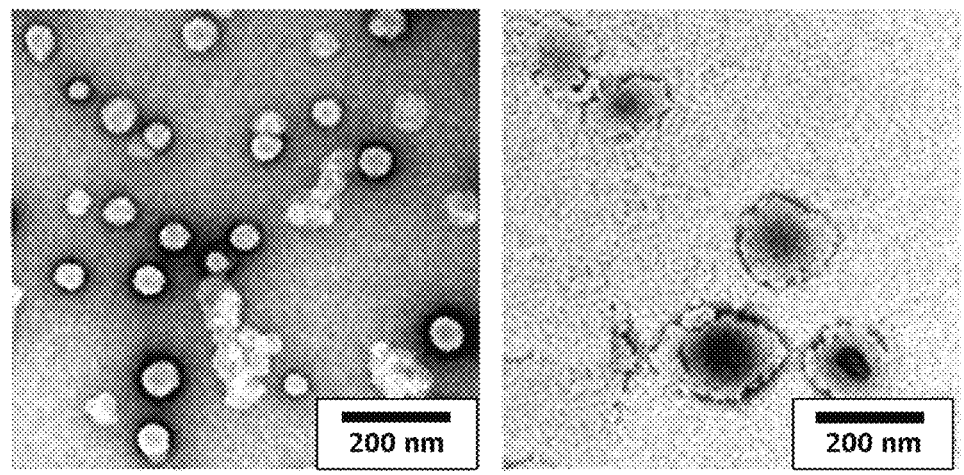
FIG. 2A—Transmission electron microscopy (TEM) images of unconjugated LNPs (lipid based particles not conjugated to a targeting antibody), (left-hand panel) or antibody-targeted lipid-based particles (tLNPs) (right-hand panel)

Example 1: Preparation and Characterization of Targeted-Lipid Nanoparticles (tLNPs), Targeted to T-Cells To prepare the effective siRNA delivery system for T cells, which include siRNA-encapsulated LNPs a microfluidic mixer system (Nanoassemblr) was used. The particles were prepared as detailed above. The mixing of acidified siRNAs (pH 4) with a mixture of lipids (cholesterol, DSPC, PEG-DMG, Dlin-MC3-DMA and DSPE-PEG-maleimide; illustrated in FIG. 1), resulted in the production of highly uniform-sized nanoparticles (NPs) that had a mean diameter of ~58 nm measured by dynamic light scattering (DLS). Since the pKa of Dlin-MC3-DMA lipid is 6.44, it is expected to provide a minimal or neutral charge at physiological pH (7.4) and indeed the zeta potential of the LNPs was shown to be about −9 mV (Table 1). The particles hydrodynamic diameter was also confirmed using transmission electron microscopy (TEM), as shown in FIG. 2 (left hand panel). To construct T-cells targeted LNPs (tLNPs), DTT reduced monoclonal antibodies (mAbs) against CD4 (clone YTS.177) were chemically conjugated to the maleimide functional group of the LNPs. This procedure resulted in tLNPs with a mean diameter of ~130 nm and a zeta potential of ~−10 mV (Table 1). This size was also validated using TEM (FIG. 2, right hand panel) and the increase in size of tLNPs could be explained by the chemical conjugation of the mAb followed by concentration of the LNPs using an Amicon centrifugal filter. siRNA encapsulation efficiency was tested using a Ribogreen assay. An encapsulation efficiency of close to 100%, was determined, since no free siRNA was detected.

Figure 3:
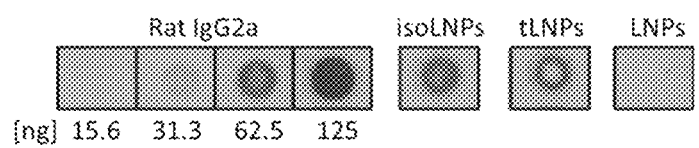
FIG. 3—Images of Dot blot analysis for antibody presence on the surface of isoLNPs (isotype-control mAb), tLNPs (targeted particles) or LNPs (no antibody) as a control.

Antibody presence on the surface of LNPs was confirmed using a dot plot assay, as shown in FIG. 3.

TABLE 1

Characterization of LNPs by dynamic light scattering and Zeta potential measurements. Data are presented as mean ± SD of six independent measurements.

| | LNPs | CD4-tLNPs |
|---|---|---|
| Hydro dynamic diameter (d · nm) | 58 ± 6 | 129 ± 5 |
| PDI | 0.1 ± 0.05 | 0.12 ± 0.02 |
| Zeta potential (mV) | −9.3±0.3 | −10 ± 0.5 |
| siRNA encapsulation (%) | 95 ± 2 | 95 ± 9 |

Example 2—Preparation and Characterization of Targeted-Lipid Nanoparticles (tLNPs), Targeted to B-Cells (MCL Cells)

Figure 2B:
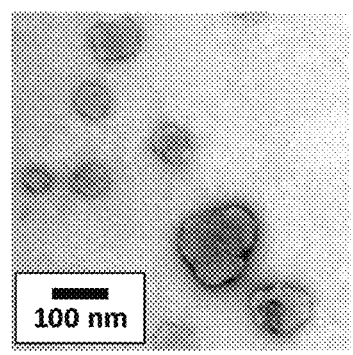
FIG. 2B—Transmission electron microscopy image of αCD38-LNPs-siRNA. White scale bar: 100 nm.

Lipid-nanoparticles (LNPs) encapsulating siRNAs using a microfluidic mixing system as described were constructed (FIG. 1B). The lipid mixture included the lipid Dlin-MC3-DMA (50 mol %), cholesterol (38%), DSPC (10%), DMG-PEG (1.95%) and DSPE-PEG-Maleimide (0.05%). αCD38 mAb (clone THB-7) was reduced to allow its chemical conjugation to maleimide groups present in the LNPs and then incubated with the LNPs. The αCD38-LNPs-siRNA had a mean diameter of ~116 nm with a narrow size distribution (PDI~0.157) as measured by dynamic light scattering (DLS, Table 2). ζ-potential measurements showed a slight negative surface charge, as expected, at physiological pH (21). Transmission electron microscopy (TEM) analysis of the LNPs indicated a globular shape and size distribution in accordance with the DLS measurements (FIG. 2B).

TABLE 2

Characterization of α CD38-LNPs-siRNA by dynamic light scattering and ζ - potential measurements.

| Hydrodynamic diameter | 116 ± 7.9 nm |
| Polydispersity index | 0.157 ± 0.017 |
| ζ Potential | −5.83 ± 1.1 mV |

Data are represented as mean±s.d. out of 12 (size & PDI) or 2 (ζ-potential) measurements for independently produced batches. All individual measurements included 3 technical replicates.

Example 3: Specific Binding of tLNPs to CD4+ T Cells Ex Vivo

Figure 4A:
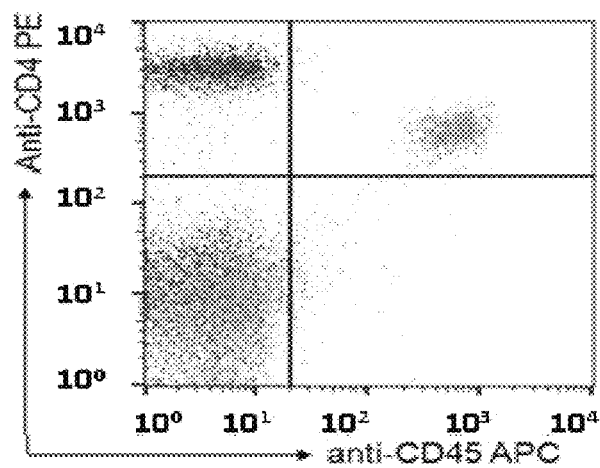
FIGS. 4A-D show tLNPs binding and internalization into CD4$^+$ T cells ex-vivo. Primary splenocytes were incubated with tLNPs (siCy5) or isoLNPs (siCy5) as a control for 30 min. CD4$^+$ cells were then labeled with anti-CD4 PE.
Figure 4B:
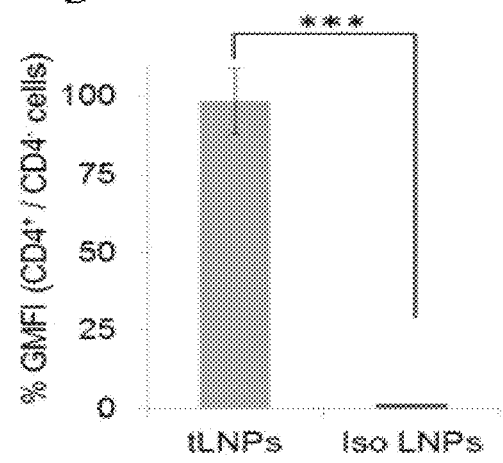

For the siRNA to be delivered to the cell, the targeting moiety should induce internalization of the nucleic acid encapsulated within the particles. To test whether tLNPs can mediate specific targeting of siRNA to CD4⁺ cells and induce internalization, tLNPs or LNPs coated with an isotype control mAb (isoLNPs) encapsulating Cy5 labeled-siRNA (siCy5) were used to treat a heterogeneous population of primary C57BL/6 splenocytes ex vivo. To measure binding to the target cells, tLNPs (siCy5) or isoLNPs (siCy5) were incubated with heterogeneous population of splenocytes, and analyzed by flow cytometry. As shown in FIG. 4A, significant and robust binding to CD4⁺ cells was observed for tLNPs ((orange) dots; right upper quartet) treated mice, while no significant binding was observed for isoLNPs treated mice (grey dots; upper left quartet). Non-specific binding to either CD8⁺ cells or B cells (left lower quartet) for mice treated tLNPs/isoLNPs was observed (FIG. 4A). Representative bar graphs are shown in FIG. 4B demonstrating that significant amount (~100%) of CD4⁺ cells bind tLNPs, as compared to isoLNPs (~1%).

Figure 4C:
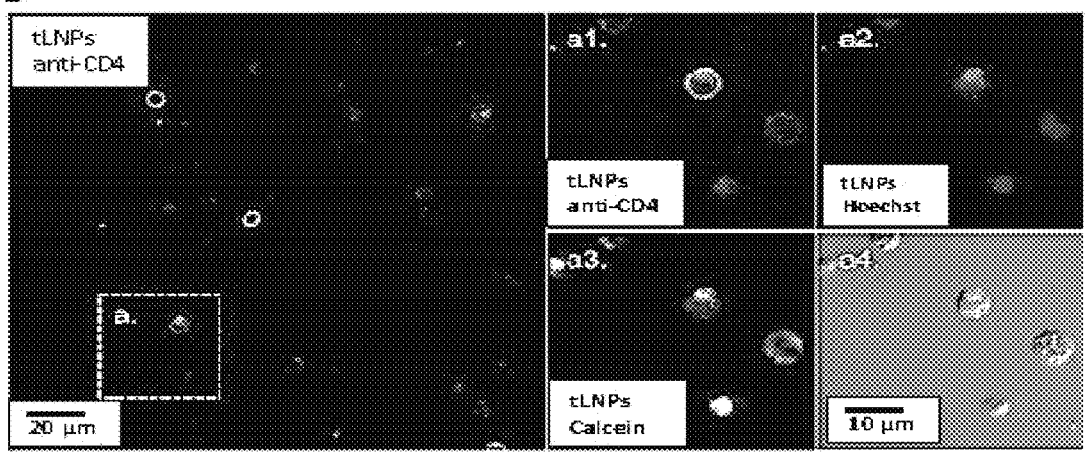
Figure 4D:
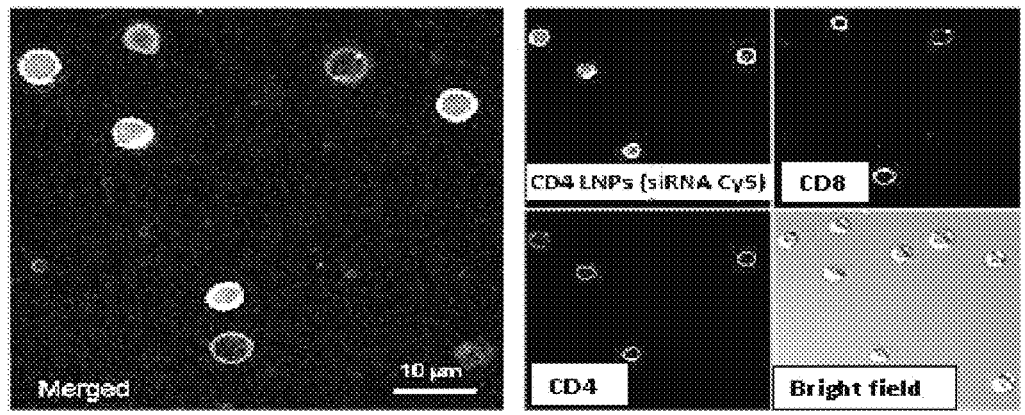

To test the tLNPs uptake, an additional stage of incubation at 37° C. for 30 min was added following tLNPs binding. Confocal microscopy was used to demonstrate the uptake of tLNPs into the target cells. As shown in FIG. 4C, the uptake of tLNPs exclusively into CD4⁺ cells based on co-labeling of the siCy5 containing cells with anti-CD4-PE (for membrane), calcein and Hoechst (for cytoplasm and nuclei staining) to validate tLNPs internalization. tLNPs specificity was also validated by labeling CD8⁺ T cell subset, that unlike CD4⁺, did not demonstrate tLNPs uptake (Supporting information Figure S2). Hence, anti-CD4 mAb coated LNPs are suitable to deliver siRNAs into CD4⁺ cells.

Example 4: Targeted Silencing in Blood Circulating CD4⁺ T Cells

To examine the capability of tLNP delivering siRNAs to silence gene expression in CD4⁺ T cells in vivo, tLNPs containing siRNAs against CD45 (tLNPs (siCD45)) were prepared. CD45, a cell surface tyrosine phosphatase, was chosen since it is a pan-leukocyte marker and thus can be used for testing specific silencing in different leukocyte subsets. First, it was tested whether tLNPs can target circulating CD4⁺ T cells. Mice were intravenously injected with tLNPs (siCy5) or isoLNPs (siCy5) as control. One hour post administration, blood was harvested, stained for markers of different leukocytes subsets and analyzed by flow cytometry. The results shown in FIG. 5A demonstrate that, remarkably, all CD4⁺ cells bound tLNPs, while none of the other leukocytes subsets examined showed Cy5 labeling compared to isoLNPs or mock treated control groups. Representative bar graphs are shown in FIG. 5B.

After confirming in vivo binding, the ability of tLNPs (siCD45) to knockdown CD45 expression in C57BL/6 mice was tested. To this end, several LNPs were used as controls, including tLNPs that were constructed using siRNA against luciferase (tLNPs(siluc)) and isoLNPs (siCD45) or LNPs (siCD45) (unmodified, non-conjugated LNPs). Five days post administration, blood was harvested and cells were stained for CD45. As shown in FIG. 5C, only mice treated with tLNPs (siCD45) resulted in CD45 silencing in leukocytes compared to the control groups. Representative histograms showing a significant reduction of CD45 levels in mice treated with tLNPs compared to isoLNPs and other control groups are presented in FIG. 5D. The data presented was performed in triplicates and reproduced with two independent experiments and with two different productions of LNPs. To test the specificity of silencing, the cells harvested from the treated animals were stained with anti-CD3 PerCP and anti-CD4 PE antibodies (FIG. 5E). Remarkably, almost 100% of the silenced cells were CD4⁺ T cells. Accordingly, a very high specificity using the tLNPs in circulating CD4⁺ T cells was obtained.

Figure 6:
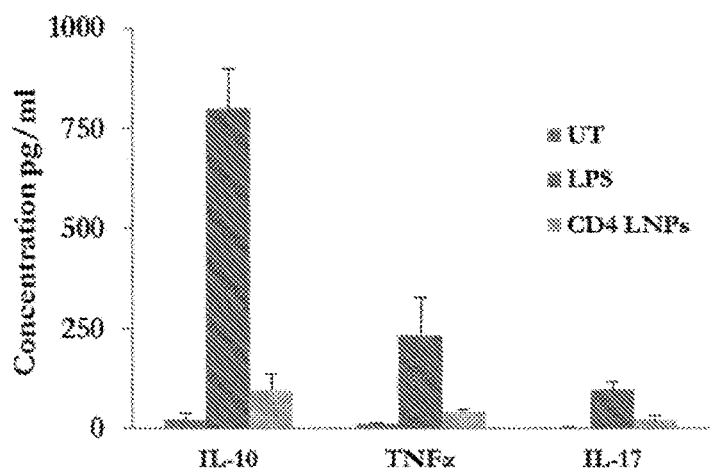
FIG. 6—In vivo immune activation study. Serum was collected from mice injected with tLNPs (siCD45) or LPS and analyzed for pro inflammatory cytokines by ELISA. Bar graphs show the concentration (pg/ml) of IL-10. TNF-alpha, and IL-17 as determined by ELISA.

Next, the tLNPs were tested for immune toxicity. To this aim, a panel of cytokines, including, TNF-α, IL-17 and IL-10 were tested, in mice treated with either the tLNPs (siCD45) or LPS, a potent TLR activator, as a positive control. As shown in FIG. 6, only a mild elevation of cytokines was observed in tLNPs (siCD45) treated mice over untreated mice.

Figure 7:
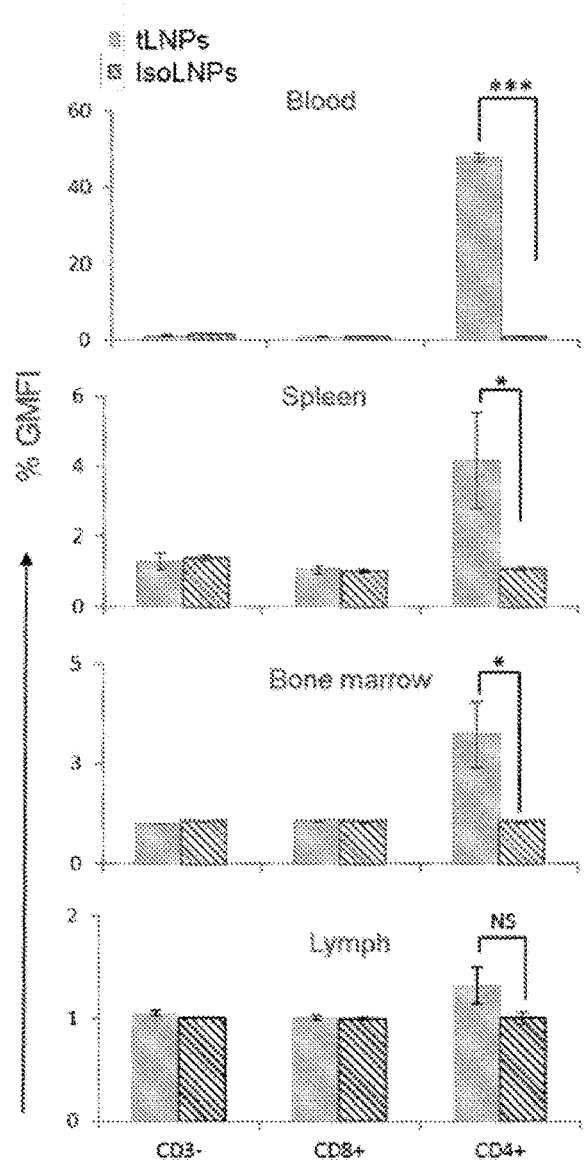
FIG. 7—Bio-distribution of tLNPs and isoLNPs: One hour post administration of tLNPs (siCy5) or isoLNPs (siCy5), lymphocytes were isolated from spleen, blood, lymph and bone marrow. Cell were stained for anti-CD4-PE and analyzed by flow cytometry. Represent histograms of percent GMFI values for Cy5 calculated form CD4 gated populations normalized to mock. Error bars represents mean±SD, n=3, NS—not significant, *p<0.05, ***p<0.0005.

Example 5—tLNPs Induce Gene Silencing in CD4⁺ T Cells in Different Hematopoietic Organs One of the challenges associated with leukocyte targeted therapies is that in order to manipulate all leukocytes of a specific subset, such as CD4⁺ T cells, the delivery agent needs to reach diverse organs within the body, since leukocyte are distributed across multiple tissues, including spleen, lymph nodes and bone marrow. To determine the breadth of siRNA delivery across lymphoid tissues, a systematic examination of the binding of tLNPs to CD4⁺ T cells in different hematopoietic organs was performed. Mice were injected intravenously with tLNPs (siCy5) or isoLNPs (siCy5). One hour post injection, cells from the spleen, inguinal lymph nodes and bone marrow were isolated and stained with a set of antibodies to detect different leukocytes subsets (anti-CD3, anti-CD4 and anti-CD8). Remarkably, all CD4⁺ T cells from each of the tissues tested showed specific binding of the tLNPs, while no binding to any of the organs has observed in mice treated with isoLNPs (FIG. 7). Although all the tissues showed binding to the CD4⁺ T cells, the binding level in different organs was heterogeneous.

Figure 9:
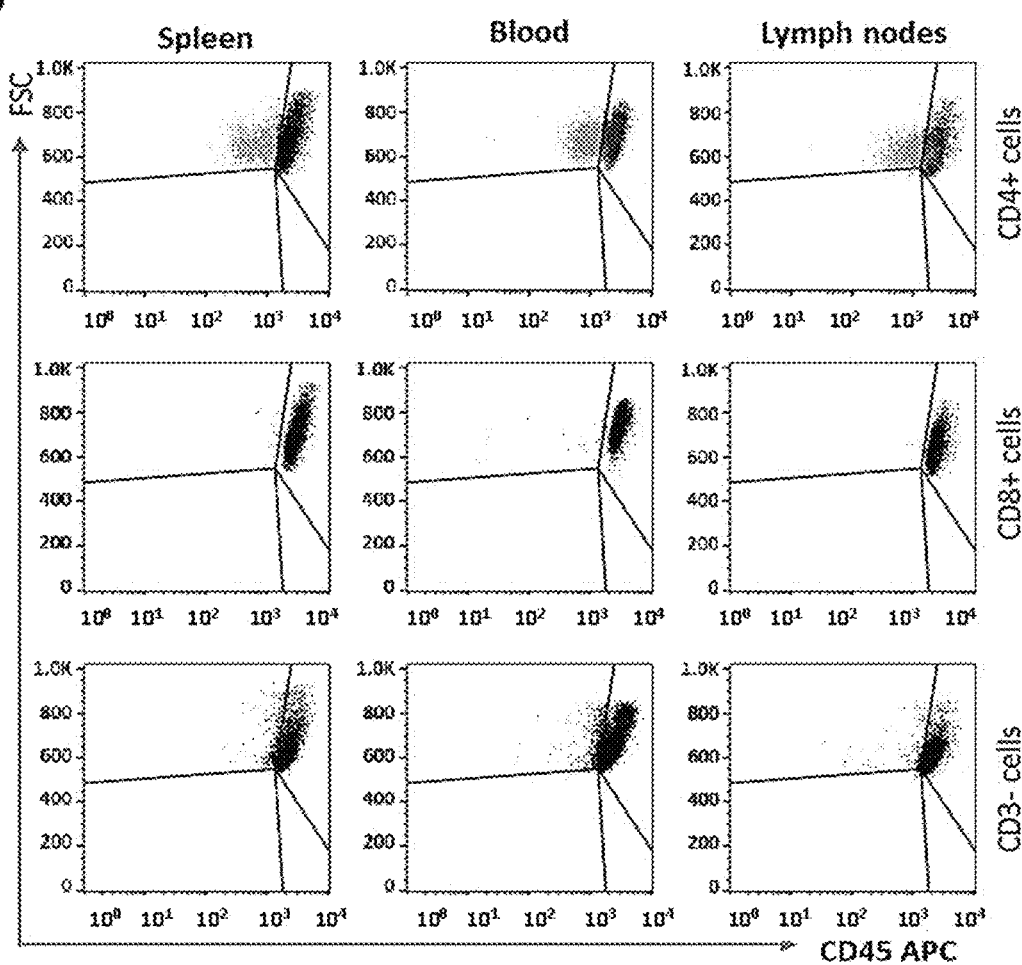
FIG. 9—tLNPs inducing gene silencing in CD4+ cells specifically in hematopoietic organs. Five days after tLNPs (siCD45) administration, spleen, lymph and blood lymphocytes were isolated and incubated with a set of antibodies (anti-CD45 APC, anti-CD4 PE, anti-CD3 PerCp and anti-CD8 FITC). Representative dot blot analysis for gated live CD4+, CD8+ or CD3− lymphocytes is presented. Silenced cells (originally orange) and unsilenced cells (originally gray) are shown.

As shown in FIG. 8A, the highest binding was observed in blood circulating CD4⁺ T cells, while the lowest binding was observed in lymph nodes. This heterogeneity could result from different tLNPs kinetics across different tissues. After demonstrating the selective binding of the tLNPs to CD4⁺ T cells in all the tested organs, its ability to induce potent gene silencing was examined. Five days post i.v. administration of tLNPs (siCD45), cells from blood, spleen, lymph nodes and bone marrow were isolated and co-stained for CD45, CD3, CD8 and CD4 expression. Flow cytometry analysis of the CD3⁺, CD4⁺ cell populations clearly shows specific CD45 knockdown from each of these analyzed tissues (FIG. 8B). As shown in FIG. 8C, the most effective silencing was observed in CD4⁺ T cells of lymph nodes with 36% of the cells staining negative for CD45 compared to the mock treated cells followed by the peripheral blood (35%), spleen (31%) and bone marrow (24%). The results presented in FIG. 8D show the silencing of CD45 in CD4⁺ T cells at the mRNA level. Notably, other cell types showed no decrease in their CD45 expression levels (FIG. 9).

Figure 10A:
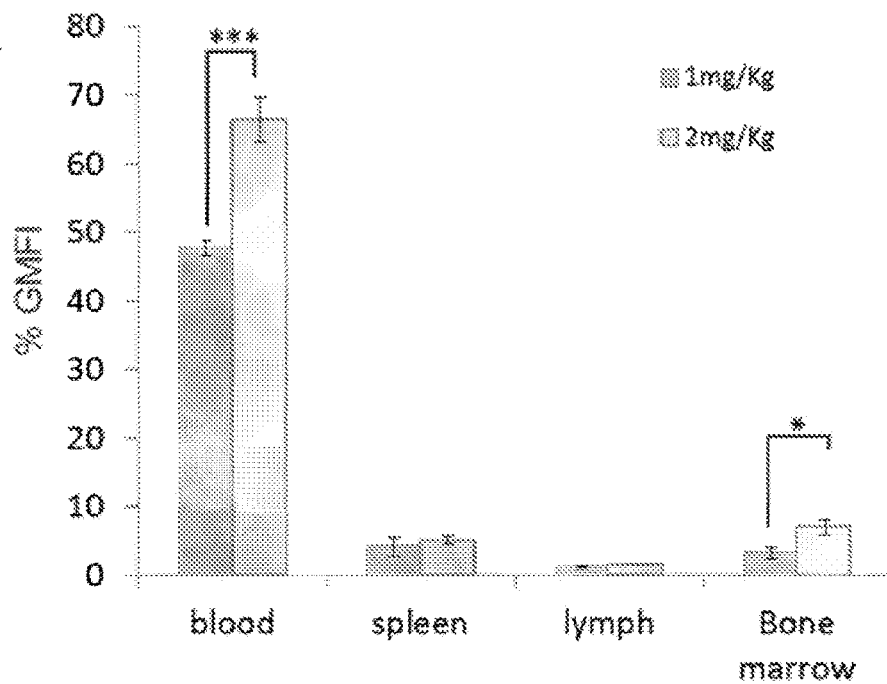
FIGS. 10A-B—Dose dependent bio-distribution and silencing.
Figure 10B:
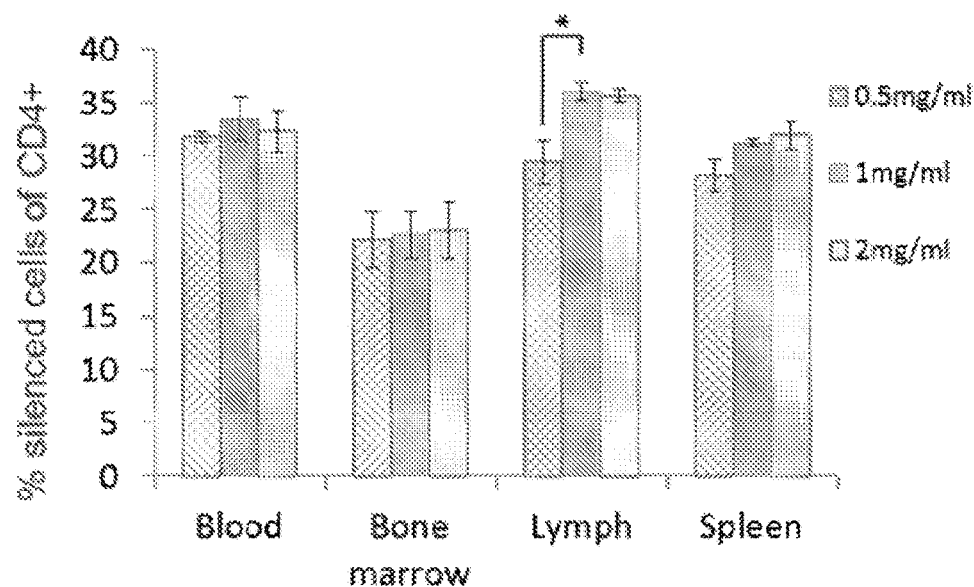

To examine whether tLNPs amount is a limiting factor, the binding and silencing efficacy of tLNPs at higher tLNPs doses (2 mg/kg siRNA) was tested. As shown in FIG. 10A, a significant higher specific binding in blood and bone marrow (FIG. 10A) of the mice treated with 2 mg/kg siRNA compared with the dose frequently used (1 mg/kg) is observed. A functional experiment using higher dose of tLNPs (siCD45) did not result in higher silencing. As shown in FIG. 10B, a dose response experiment using 0.5, 1 and 2 mg/kg siRNA, showed a significant advantage to 1 mg/kg compare with 0.5 mg/kg in the lymph nodes, without any significant change in silencing with 2 mg/kg dose. To further validate siRNA silencing, CD4⁺ T cells, CD45$^{KD}$ (KD—knock down) cells from the spleen of the tLNPs treated animals and CD4+ cells from mock treated animals were isolated by using Cell sorter (BD FACSAriaIII™) CD45 mRNA expression levels were analyzed by quantitative real time PCR (qRT-PCR). As shown in FIG. 8D, a significant (~80%) decrease in CD45 mRNA levels was observed in CD4+ T cells collected from tLNPs treated mice compared with mock treated CD4+ T cells.

Figure 11A:
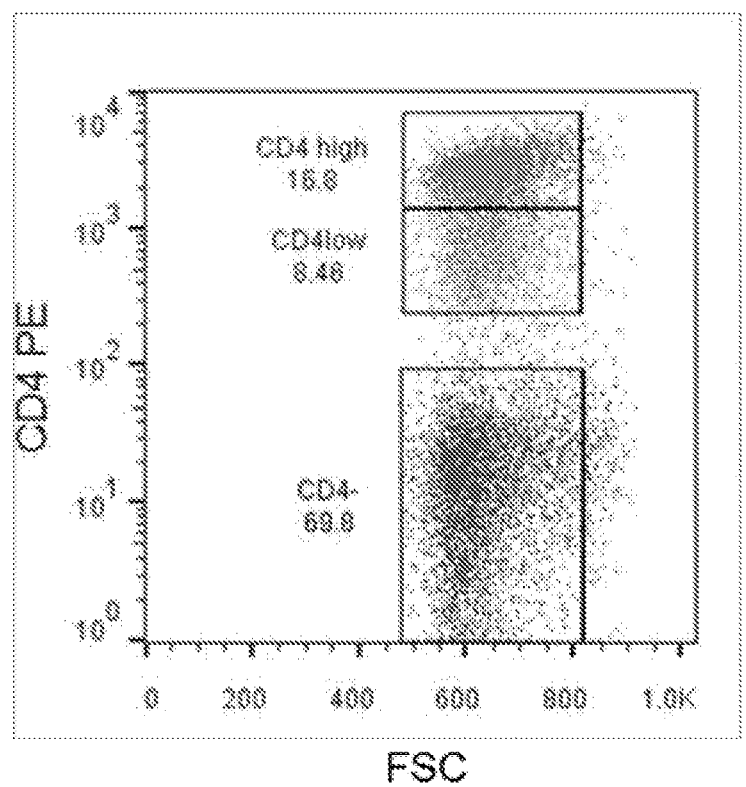
FIGS. 11A-B: CD4low T cells are positive for CD3. One hour after tLNPs (siCD45) administration, splenocytes were isolated and incubated with anti-CD4 PE and anti-CD3 PerCp.
Figure 11B:
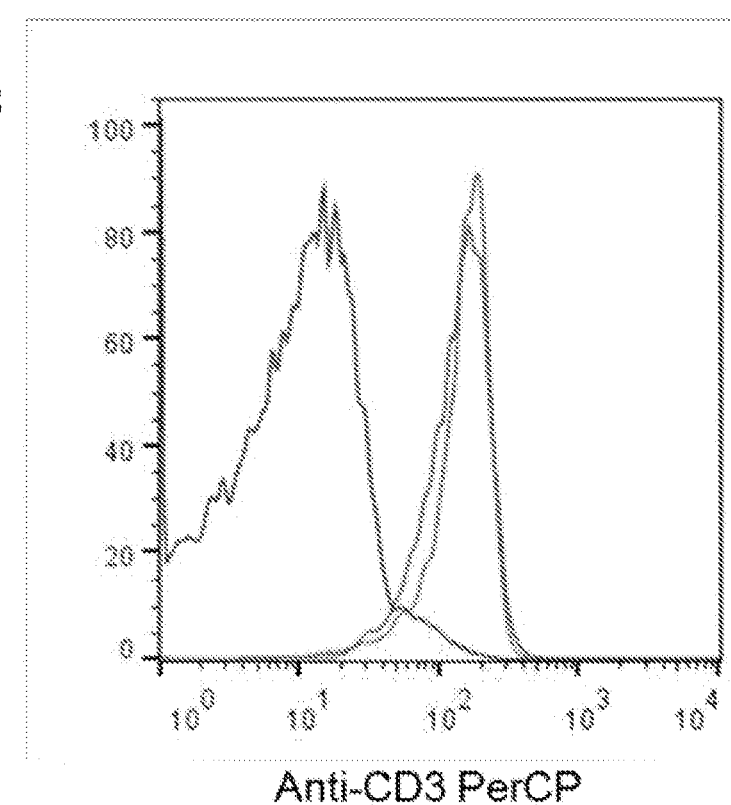
Figure 12A:
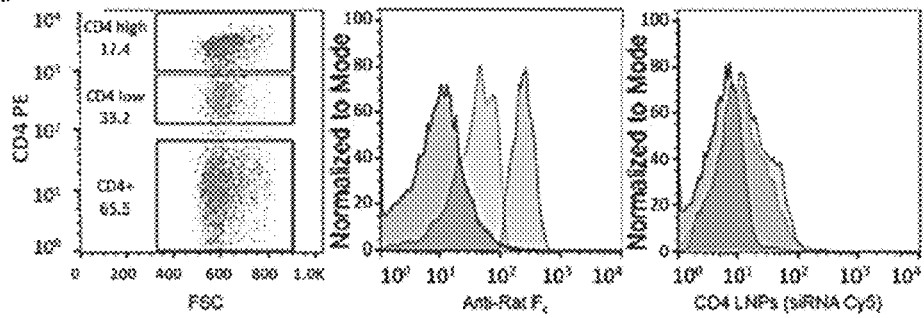
FIGS. 12A-E: LNPs internalization by CD4 subset followed by functional silencing.
Figure 12B:
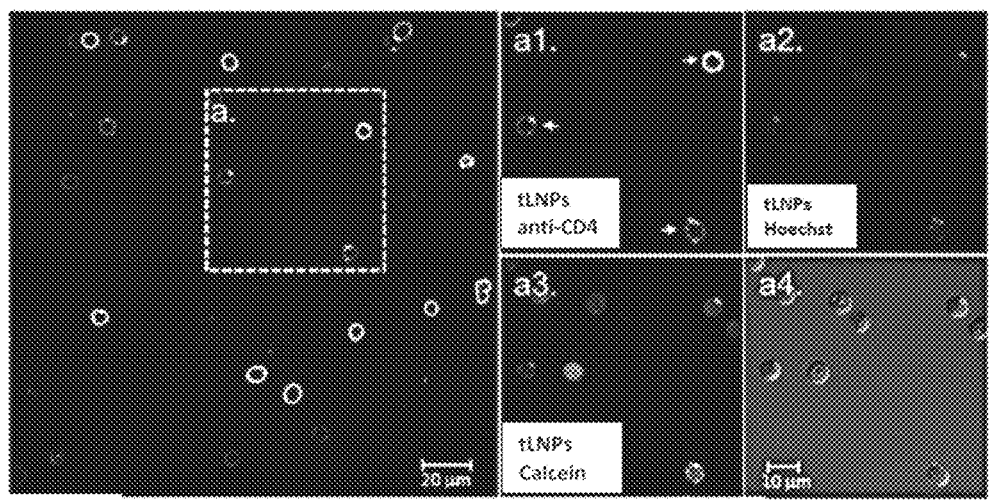

Example 6—tLNPs are Internalized by Distinct CD4 Subset Followed by Functional Silencing After establishing tLNPs as a platform strategy to specifically silence genes of interest using siRNAs in circulating and resting CD4+T lymphocytes (using the pan leukocyte surface marker CD45 as a gene model), the mechanism that underlie the differences between the two CD4+ T cell populations that differ in their response to the tLNPs was investigated. One demonstrate CD45 silencing and the other do not alter its CD45 expression levels. Intriguingly, two distinct CD4+ T cell populations were noticed in all tissues tested in binding experiments after 1 h (FIG. 8A) or 4 h after tLNPs administration. One shows high CD4 PE staining, as in mock cells ($CD4^{high}$) and the other presents low CD4 PE staining ($CD4^{low}$). $CD4^{low}$ population represents CD4+ T cells and not a different population of cells since this population of cells stained positively for the T cell co-receptor CD3 encompassing both the $CD4^{high}$ and $CD4^{low}$ cell populations (FIGS. 11A-B). This $CD4^{low}$ population of cells was not found in the untreated mice. Since the percent of the $CD4^{low}$ population resembled the silencing percent obtained in the silencing assays, it was tested whether the reduction in anti-CD4 PE can be a result of CD4 receptor sequestering from the membrane due to tLNPs internalization, followed by silencing. To determine if there was a correlation between low CD4 surface expression and tLNP internalization, the level of internalized tLNPs (siCy5) was tested by both flow cytometry and confocal microscopy analysis. For flow cytometer assay a secondary antibody (anti-Rat Fc) directed against the fragment crystallizable (Fc) region of the CD4 mAb of tLNPs was used. This experimental method is not designed to detect internalizing particles but rather cell surface bound particles. Flow cytometry analysis clearly demonstrates that although the amount of siCy5 is similar between $CD4^{low}$ and $CD4^{high}$ cells, $CD4^{low}$ population has less tLNPs on the surface, since $CD4^{low}$ have reduced staining of anti-Rat Fc compared to $CD4^{high}$ population (FIG. 12A). These results were validated by confocal microscopy, in which cytoplasm, nuclei and CD4 membrane were stained with calcein, Hoechst and anti-CD4 respectively to insure tLNPs cytoplasmic localization. As shown in FIG. 12B, $CD4^{low}$ cells have effectively internalized the tLNPs (siCy5), on the other hand, $CD4^{high}$ cells had lower levels of internalized tLNPs (siCy5) with the majority of tLNPs located on the surface (FIG. 12B). Therefore, these results demonstrate that two populations of CD4 cells ($CD4^{low}$ and $CD4^{high}$ cells) in the tLNP treated samples may reflect the degree of internalization and sequestration of the CD4 molecules. This could suggest that there may be differences between CD4+ cells populations in their ability to endocytose the tLNPs and may explain the CD45 knockdown efficiency as seen in FIG. 8B.

Figure 12C:
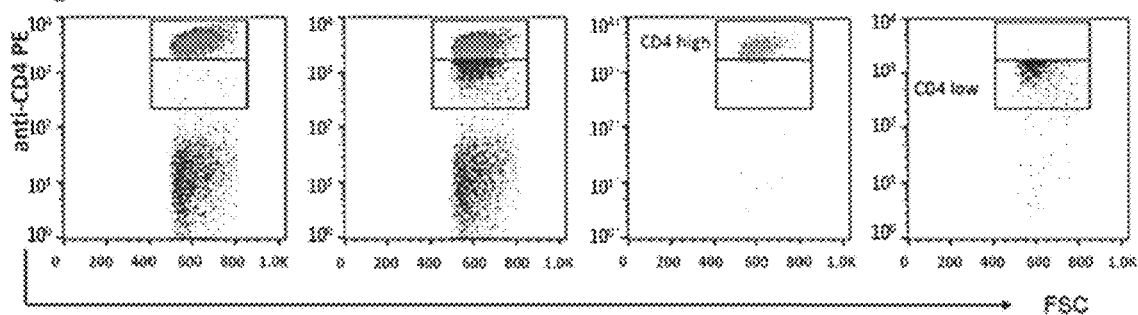
Figure 12D:
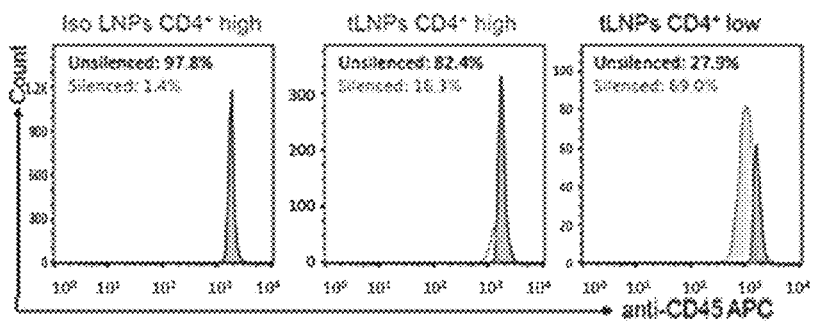
Figure 12E:
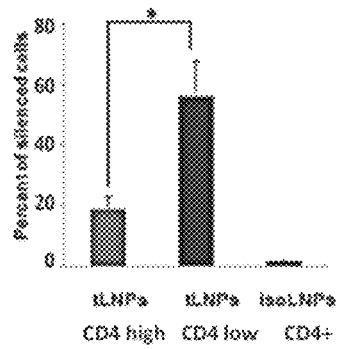

Next, it was aimed to confirm that $CD4^{low}$ cells not only internalize the tLNPs, but also that this internalization leads to silencing. This will determine that the bottleneck for gene silencing in CD4 cells using tLNPs system is the internalization step. For this purpose, an experiment in which $CD4^{low}$ and $CD4^{high}$ populations are separated by FACS Sorter (FIG. 12C), one hour after administration of tLNPs (siCD45) in vivo and CD45 expression levels are tested after 3 days in culture. As a control, CD4+ cells from mice treated with iso LNPs (siCD45), in which no $CD4^{low}$ population was observed were sorted. Remarkably, up to 70% silencing was observed in $CD4^{low}$ populations compared with 16% in $CD4^{high}$ population. Neglected 2% silencing was observed in $CD4^{high}$ population of isoLNPs treated group (FIG. 12E).

Figure 13A:
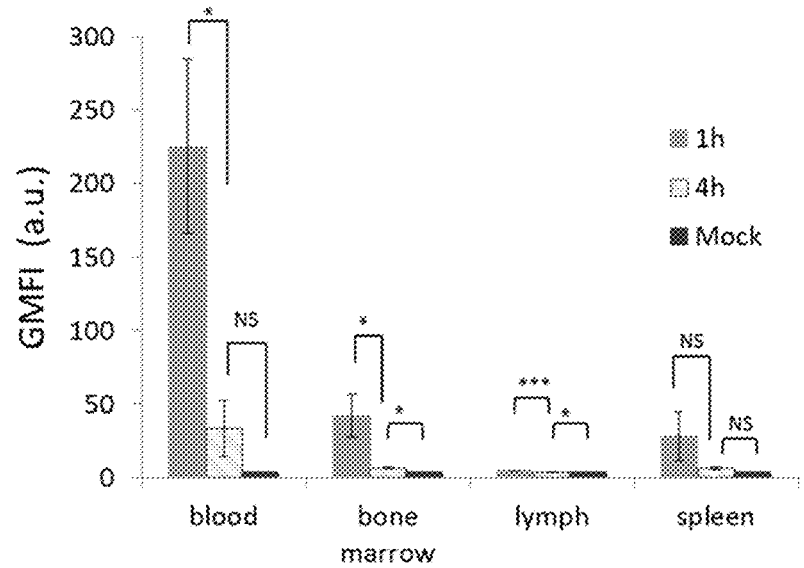
FIGS. 13A-B: Bio distribution of tLNPs. Mice were injected tLNPs (siCy5) and splenocytes were isolated at 1 h and 4 h time points, stained with anti-CD4-PE and analyzed by flow cytometry.
Figure 13B:
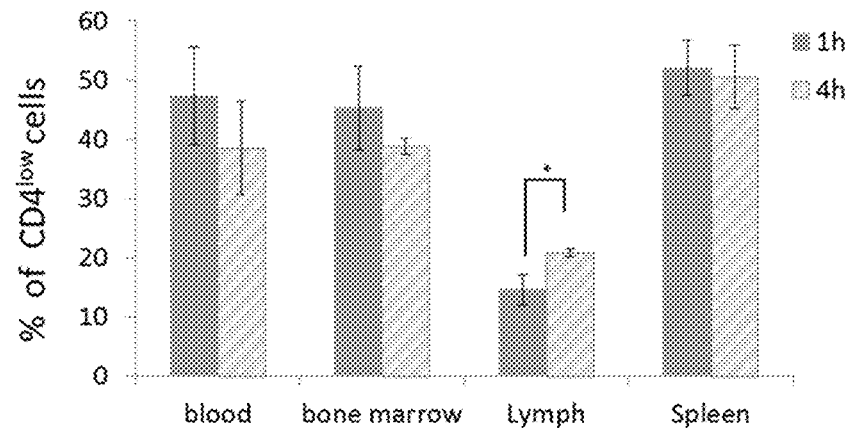

Revealing that $CD4^{low}$ is the silenced population also contributes to decipher how lymph node $CD4^{+\ T\ cells}$ exhibit high knockdown efficacy while showing the lowest tLNPs uptake. Following uptake of the particles at the single cell level is limited when using siCy5 due to degradation of the florescence dye along with florescence decay due to low endosomal pH. Indeed Cy5 labeling is dramatically decrease among all tissues 4 h post administration (FIG. 13A), however since $CD4^{low}$ represent the silenced cells that internalize the tLNPs, their fate may be followed. Interestingly, after 4 hours a significant increase of 5.5% in $CD4^{low}$ in lymph nodes accompanied by a trend of a $CD4^{low}$ decrease in other tissues can be detected (FIG. 13B). This might imply that more tLNPs accumulate in the lymph after 4 hours or that CD4 cells have migrated to the lymph.

Figure 14A:
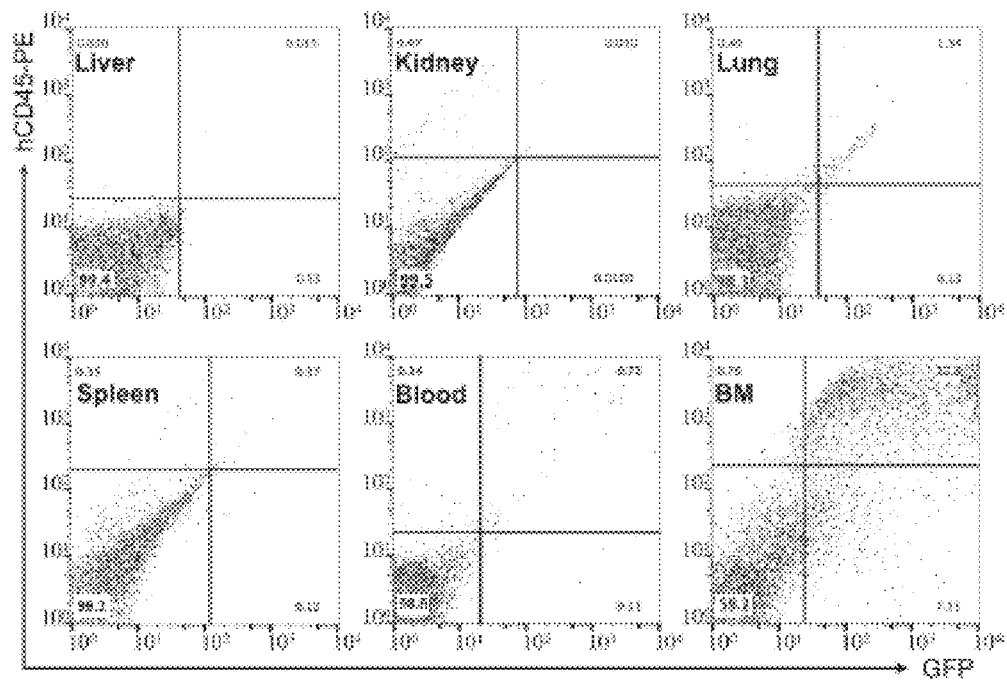
FIGS. 14A-B—MCL-xenograft model. Granta-GFP cells were i.v. injected into CB-17 SCID mice.
Figure 14B:
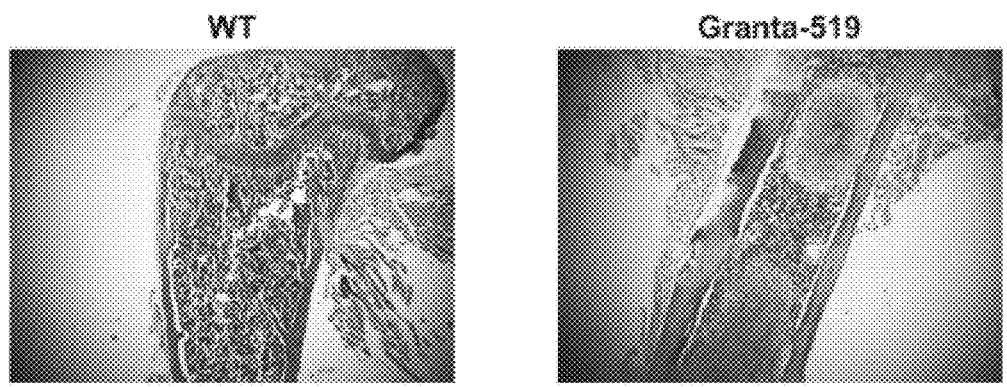

Example 7—Model Establishment—MCL Cells are Mainly Engrafted in the Bone Marrow of SCID Mice To test the ability of αCD38-LNPs-siCycD1 to target dispersed MCL cells, an animal model of disseminated MCL in which MCL cells home to the bone marrow (BM), as in the advanced stages of the human disease was established. Granta-519 cells ($2.5 \times 10^6$) stably expressing GFP (Granta-GFP) were injected intravenously (i.v.) into 6-8 weeks old female C-mB-17 SCID mice. These mice developed hind-leg paralysis after 24 to 30 days, at which time liver, lungs, spleen, kidney, blood and BM cells were harvested to assess the distribution of MCL cells by flow cytometry. Granta-GFP cells consistently homed to the bone marrow (FIG. 14A). There were also some tumor cells in the lung, but very few in the liver, kidney, spleen or circulation. Bone marrow tumors that displaced normal bone marrow were prominent in H&E stained femoral slices, as shown in FIG. 14B.

Example 8—CD38—a Receptor Target for MCL

Figure 15A:
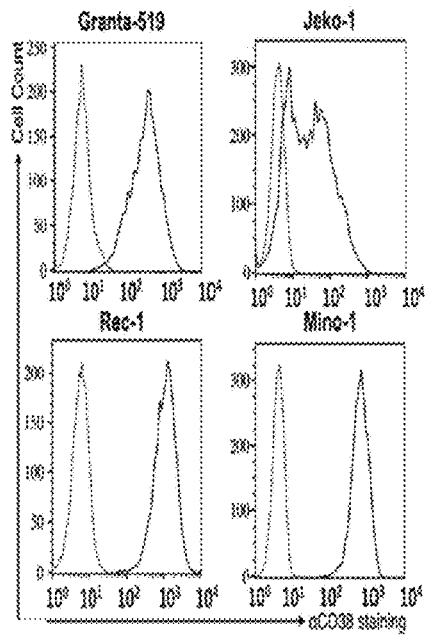
FIGS. 15A-D—αCD38 mAb targets MCL cells and induces cellular internalization.
Figure 15B:
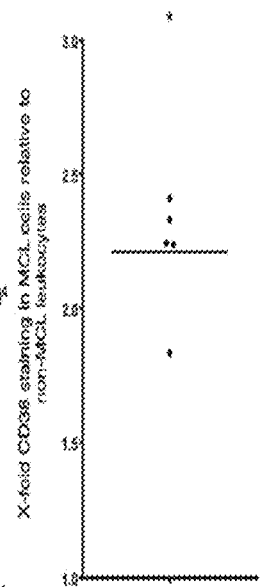
Figure 15C:
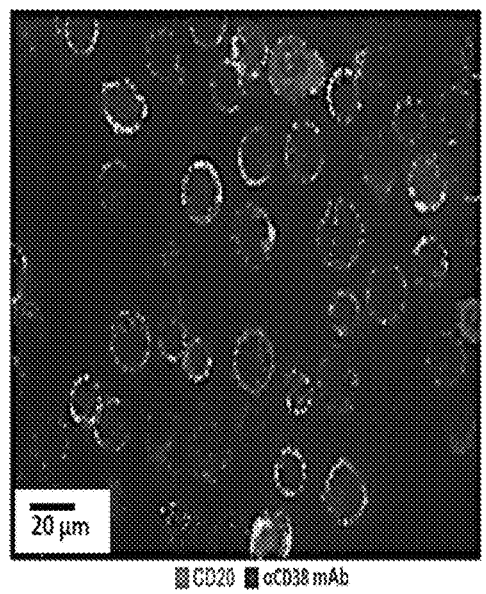
Figure 15D:
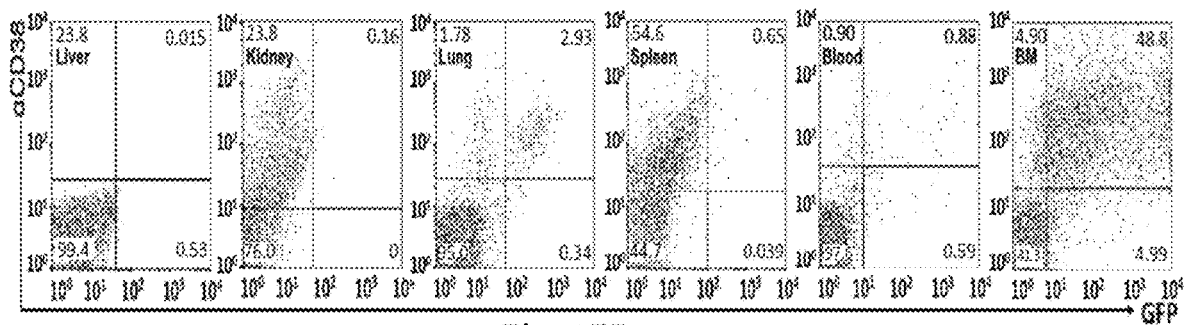

Targeting siRNAs selectively to tumors requires the identification of a cell surface receptor that is over-expressed on tumor cells compared to most other tissues, whose binding leads to endocytosis and release of endocytosed siRNAs into the target cell cytoplasm. Consistent with previous reports (Chang et. al.), it was found that CD38 is highly and broadly expressed on four tested MCL lines (FIG. 15A) and on human primary MCL samples (FIG. 15B). In vitro incubation of Granta-519 cells with fluorescently labeled CD38 mAb (clone THB-7, αCD38) led to internalization of the antibody-receptor complex (FIG. 15C). Next, labeled αCD38 mAb binding after i.v. injection into mice bearing Granta-GFP lymphomas was checked (FIG. 15D). Virtually all of the GFP+ lymphoma cells in the BM and lung bound the antibody. While only few normal GFP− liver, blood or lung bound αCD38, about half of GFP− spleen cells and a quarter of kidney cells bound it, but the staining was generally less intense than for the GFP+ tumor cells. These findings indicate the potential of THB-7 mAb and the CD38 receptor to serve as targeting moiety and target receptor, respectively, for specific delivery of LNPs to MCL in vivo.

Example 9—αCD38-LNP-siRNA Specifically Bind and Internalize into MCL Cells

Figure 16A:
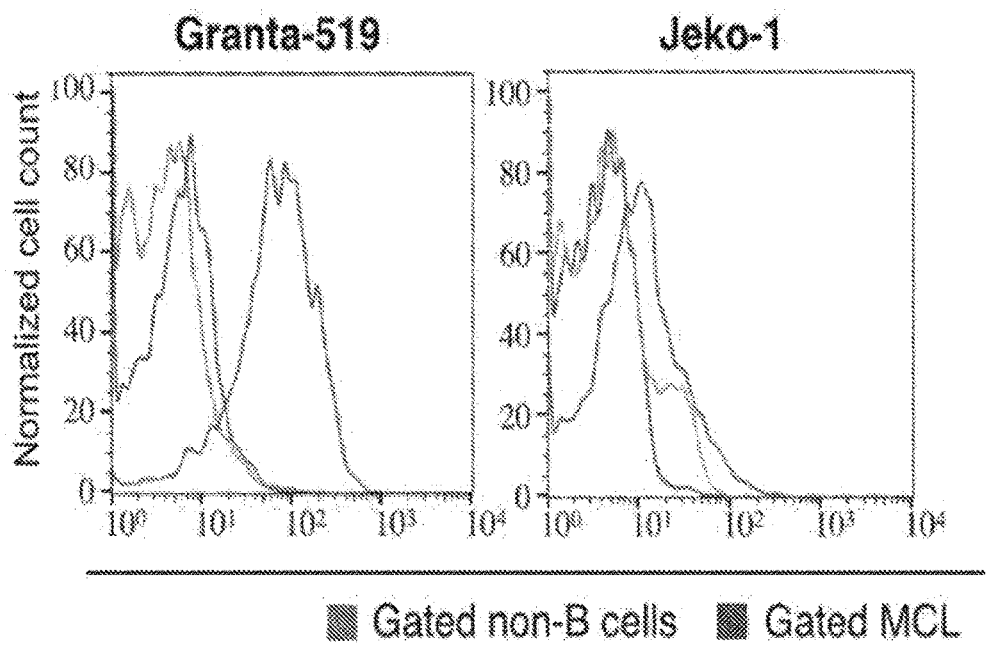
FIGS. 16A-C. αCD38-LNPs-siRNA mediate active delivery of siRNA specifically into MCL cells.
Figure 16B:
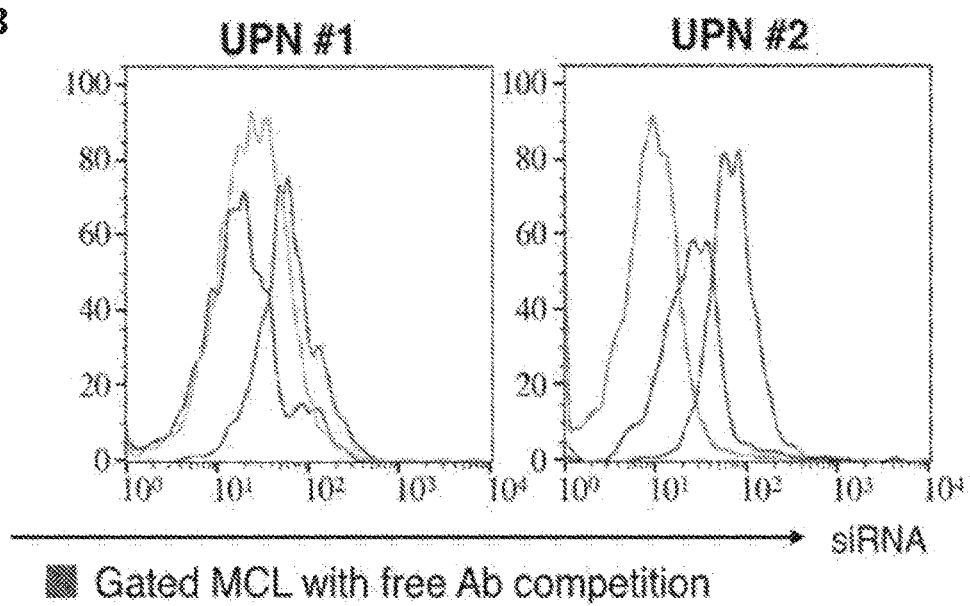
Figure 16C:
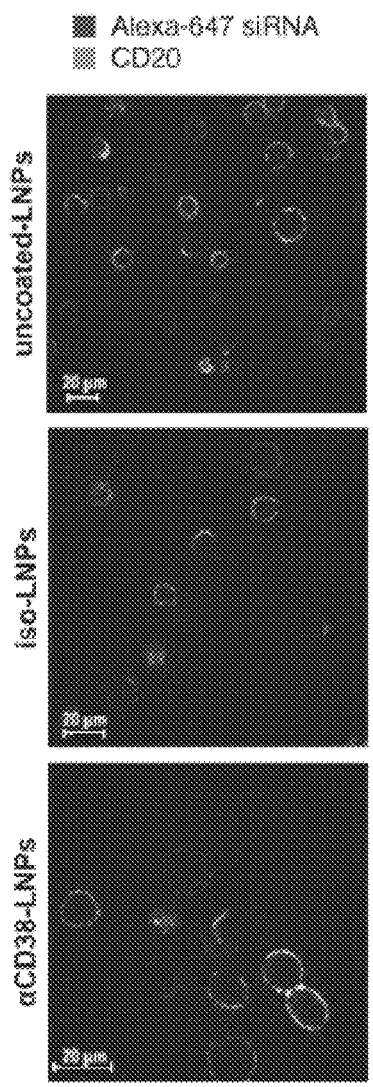

To test whether αCD38-LNPs-siRNA specifically bind to MCL cells, human MCL were co-cultured with CD38- (negative) mouse T lymphoma TK-1 cell lines and the mixtures were with αCD38-LNPs-siRNA (as prepared in Example 2) containing fluorescently labeled siRNAs (FIG. 16A). siRNA uptake was determined by flow cytometry. αCD38-LNPs-siRNA selectively bound to the MCL cell lines, as indicated by higher fluorescence intensity levels in those cells. Moreover, addition of free unlabeled αCD38 mAbs to the co-cultures decreased particles' binding to background levels, indicating that binding was via CD38. Similar results were obtained using two primary human MCL samples (FIG. 16B). Next, incubated Granta-519 cells were incubated with LNPs that were uncoated or coated with αCD38 or an isotype control antibody and entrapped fluorescently labeled siRNAs. Following incubation, the cells were imaged by confocal microscopy using αCD20 to stain their cell surface (FIG. 16C). Bound and internalized siRNA was only detected with the αCD38-coated LNPs.

Figure 17A:
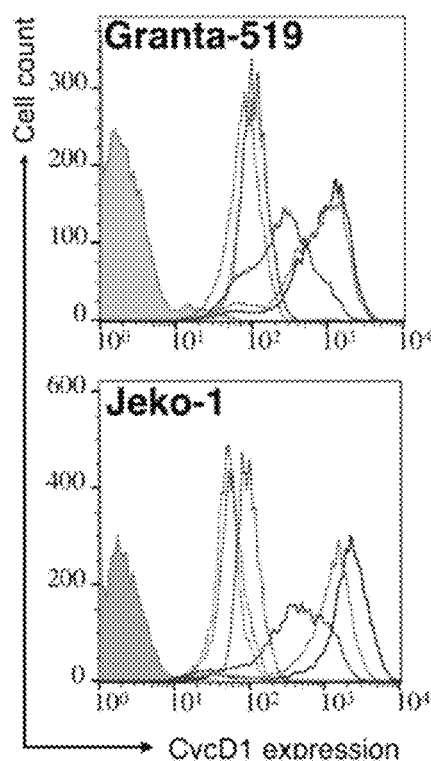
Figure 17B:
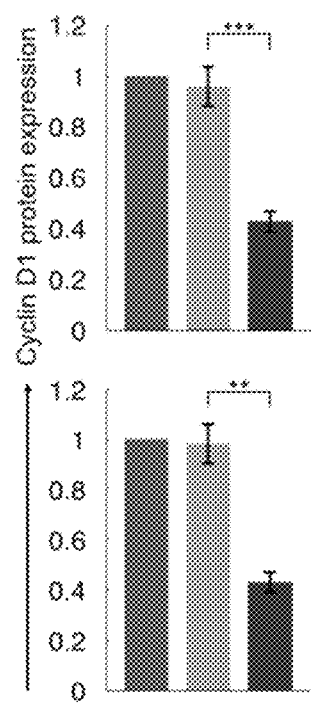
Figure 17C:
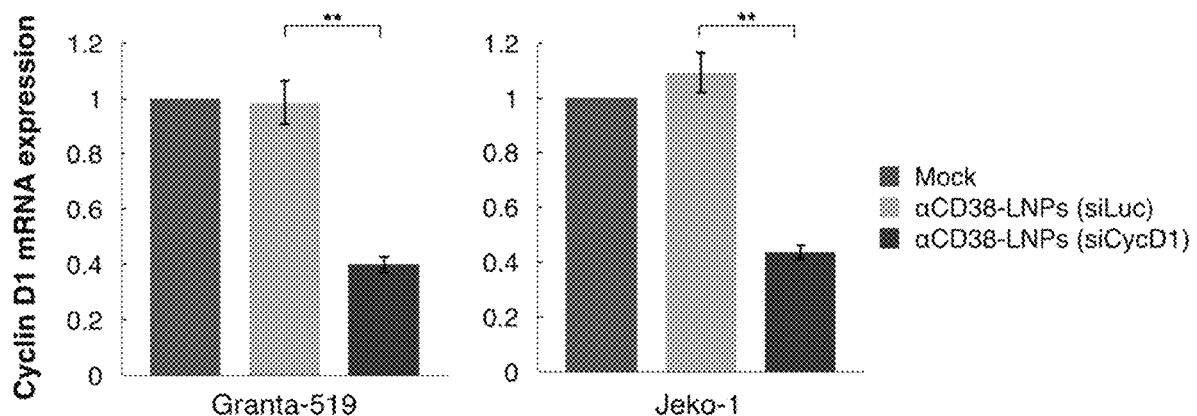

Example 10—αCD38-LNPs-siCycD1 Induce Robust Gene Knockdown and Cell Cycle Arrest Next it was examined whether αCD38-LNPs loaded with cycD1 siRNA (siCycD1), or as control luciferase siRNA (siLuc), could mediate gene silencing in two MCL cell lines, Granta-519 and Jeko-1 (FIG. 17A and FIG. 17B). When these MCL cell lines were treated with αCD38-LNPs-siCycD1 they exhibited an average 55.7% (P<0.001) and 56% (P<0.002) reduction in CycD1 protein levels determined by flow cytometry compared to αCD38-LNPs-siLuc. The latter particles did not significantly affect CycD1 levels. CycD1 knockdown was also confirmed at the mRNA level by qRT-PCR (FIG. 17C). The reduction in CycD1 levels in the αCD38-LNPs-siCycD1 incubated cells caused a cell cycle arrest in the Go/G phase (FIG. 17D). This effect was evident even though down regulation of cycD1 induced compensatory elevation of other D cyclins expression. As shown in FIG. 17E, qRT-PCR analysis of CCND1, CCND2 and CCND3 mRNA levels 24, 48, 72 and 96 hours post electroporation in Granta-519 (left) and Jeko-1 (right) cells reveales that Cyclin D2 was consistently overexpressed following treatment with siCycD1. Cyclin D3 exhibited lower or stable expression following treatment, before a pronounced increase at Day 4 post electroporation. Expression was normalized to both eIF3a and eIF3c genes and depicted as mRNA concentration relative to cells electroporated with siLuc.

CycD1 overexpression is a prominent genetic hallmark and tumorigenic factor in MCL. The relevance of selective cycD1 silencing in MCL has been questioned before due to compensatory elevation of cyclin D2 expression. As shown, it was detected that the down-regulation of cycD1 expression induces a compensatory upregulation of cyclin D2 expression (FIG. 17E). A similar compensatory expression pattern regarding cyclin D3 was detected as well. The compensatory expression of these genes did not mask the effects of cycD1 silencing in MCL cells (as demonstrated in FIGS. 17B and 17D). Studies have shown that the compensatory activity of other D cyclins allow cycD1 knockouts mice to be viable and to show only limited developmental defects. Therefore it is reasonable that undesired non-specific uptake of αCD38-LNPs-siCycD1 by non-MCL bystander cells would exhibit only low or no adverse effects.

Example 11—αCD38-Coated LNPs Specifically Target MCL Cells In Vivo

Figure 18A:
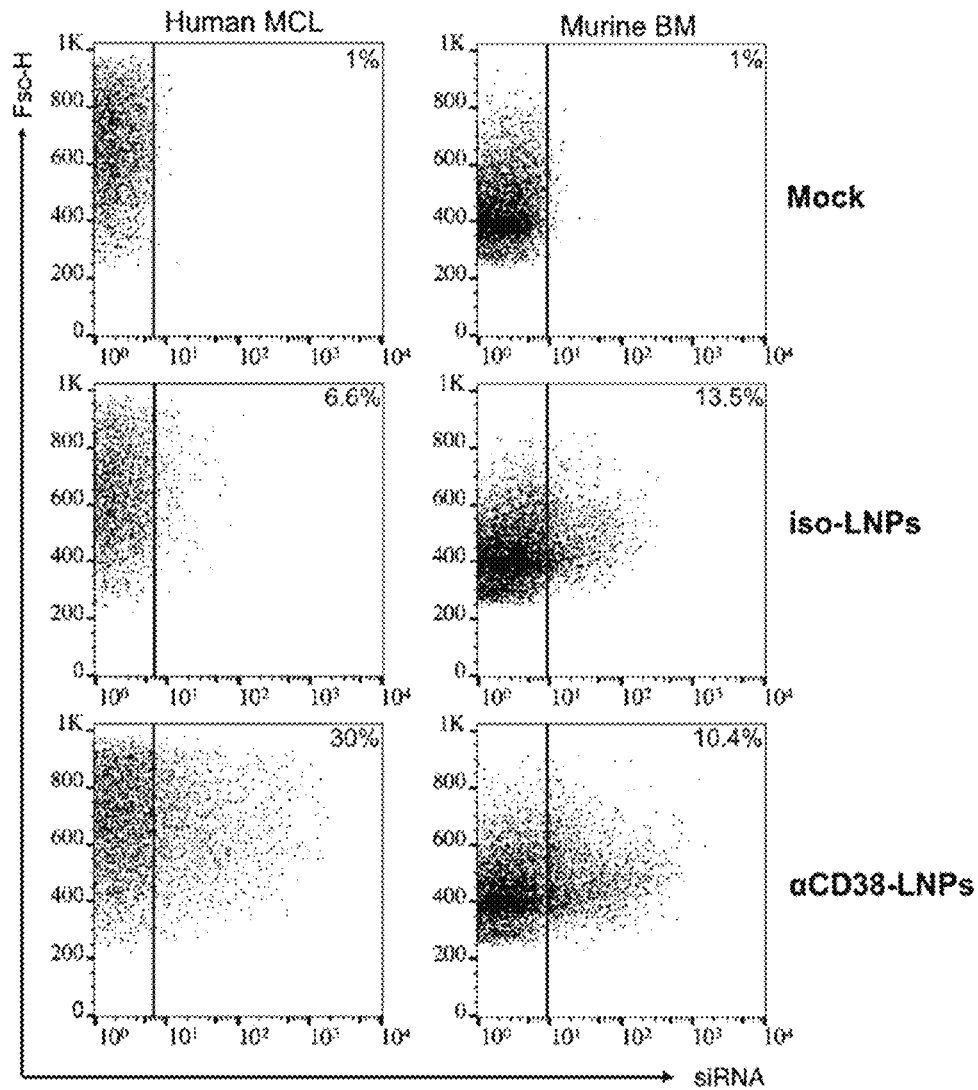
FIGS. 18A-D. αCD38-LNPs-siCycD1 target MCL xenografts in the BM and prolong the survival of diseased mice.
Figure 18B:
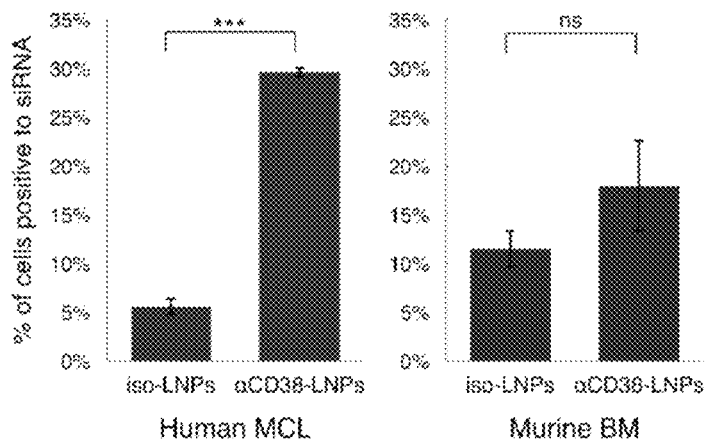

The ability of αCD38-LNP-siRNA to deliver siRNAs into Granta-519 xenografts in vivo, was tested. When hind leg paralysis appeared, MCL-bearing mice were mock treated or treated i.v. with LNPs, loaded with fluorescently labeled siRNAs, those were coated with αCD38 or an isotype control antibody. BM was extracted 2 hours later and analyzed by flow cytometry for siRNA uptake into mouse CD45+ cells and the human tumor, stained with anti-human CD20 antibody (FIG. 18A and FIG. 18B). Fluorescent siRNAs were detected in ~30% of MCL cells in mice treated with αCD38-LNP-siRNA, compared to ~6% of isotype-LNPs-siRNA (P<0.0002). Although about 15% of mouse BM cells were labeled with the fluorescent siRNA, there was no significant difference in siRNA accumulation between mice treated with αCD38 or control antibody-coated LNPs (P=0.38). Thus αCD38-LNPs-siRNA specifically bind to MCL cells in the BM in vivo.

Figure 18C:
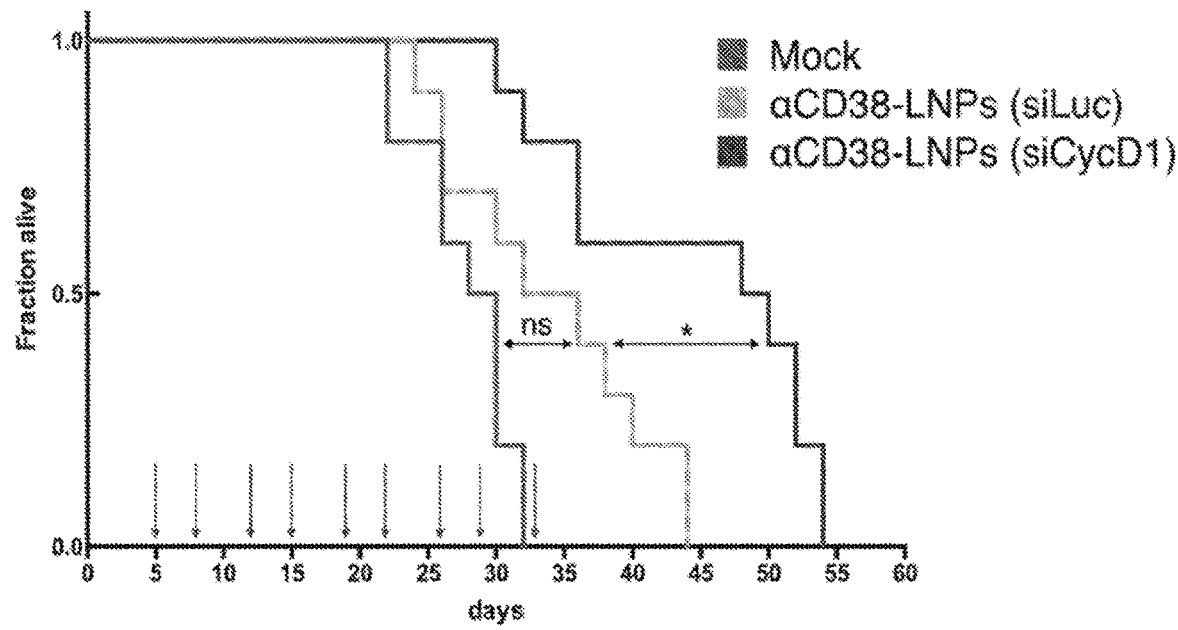
Figure 18D:
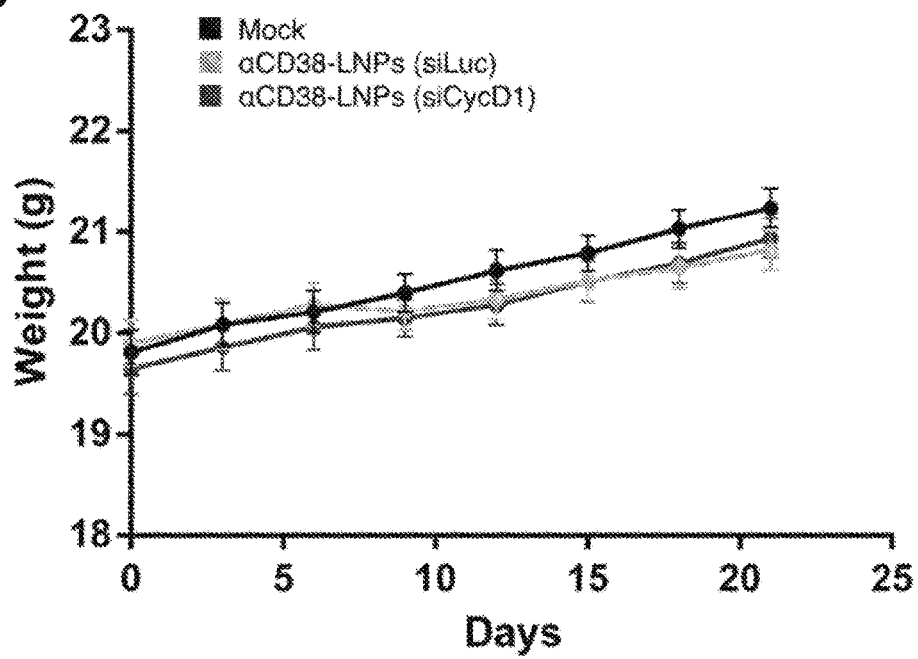

Example 12—CD38-LNPs-siCycD1 Induce Therapeutic Gene Silencing in MCL Cells in Vivo The therapeutic effect of CD38-LNPs-siCycD1 on the survival of MCL-bearing mice was tested. Mice (n=10/group) were treated biweekly with 9 i.v. injections of 1 mg/kg siRNA, starting 5 days after tumor inoculation. Control mice were mock treated or treated with CD38-LNPs-siLuc. No loss in body weight was observed during the first 21 days of the experiment, indicating that the treatments did not induce major adverse effects (FIG. 18D). Treatment with αCD38-LNPs-siCycD1 increased median survival from 34 to 49 days (P=0.0087) compared to αCD38-LNPs-siLuc treatment (FIG. 18C). Survival of mice treated with the luc-targeting control LNPs was not significantly different from survival of mock treated mice. These findings demonstrate the beneficial therapeutic effect of using siCycD1 in vivo in MCL-bearing mice.

REFERENCES

Behlke M A (2006) Progress towards in vivo use of siRNAs. *Molecular therapy: the journal of the American Society of Gene Therapy* 13(4):644-670.

Peer D & Lieberman J (2011) Special delivery: targeted therapy with small RNAs. *Gene therapy* 18(12):1127-1133.

Peer D (2013) A daunting task: manipulating leukocyte function with RNAi. *Immunological reviews* 253(1):185-197.

Jares P, Colomer D, & Campo E (2012) Molecular pathogenesis of mantle cell lymphoma. *The Journal of clinical investigation* 122(10):3416-3423.

Wang M L, et al. (2013) Targeting BTK with ibrutinib in relapsed or refractory mantle-cell lymphoma. *The New England journal of medicine* 369(6):507-516.

Campo E & Rule S (2015) Mantle cell lymphoma: evolving management strategies. *Blood* 125(1):48-55.

Cheah C Y, et al. (2015) Patients with mantle cell lymphoma failing ibrutinib are unlikely to respond to salvage chemotherapy and have poor outcomes. *Annals of oncology: official journal of the European Society for Medical Oncology/ESMO*.

Dreyling M (2014) Mantle cell lymphoma: biology, clinical presentation, and therapeutic approaches. *American Society of Clinical Oncology educational book ASCO. American Society of Clinical Oncology. Meeting*:191-198.

Weinstein S, et al. (2012) RNA Inhibition Highlights Cyclin D1 as a Potential Therapeutic Target for Mantle Cell Lymphoma. *PloS one* 7(8):e43343.

Peer D (2014) Harnessing RNAi nanomedicine for precision therapy. *Molecular and cellular therapies* 2:5.

Wittrup A & Lieberman J (2015) Knocking down disease: a progress report on siRNA therapeutics. *Nature reviews. Genetics* 16(9):543-552.

Weinstein S & Peer D (2010) RNAi nanomedicines: challenges and opportunities within the immune system. *Nanotechnology* 21(23):232001.

He W, et al. (2014) Discovery of siRNA lipid nanoparticles to transfect suspension leukemia cells and provide in vivo delivery capability. *Molecular therapy: the journal of the American Society of Gene Therapy* 22(2):359-370.

Jayaraman M, et al. (2012) Maximizing the potency of siRNA lipid nanoparticles for hepatic gene silencing in vivo. *Angewandte Chemie (International ed. in English)* 51(34):8529-8533.

Tam Y Y, Chen S, & Cullis P R (2013) Advances in Lipid Nanoparticles for siRNA Delivery. *Pharmaceutics* 5(3): 498-507.

Zimmermann T, et al. (Phase I First-in-Humans Trial of ALN-TTRsc, a Novel RNA Interference Therapeutic for the Treatment of Familial Amyloidotic Cardiomyopathy (FAC). *Journal of Cardiac Failure* 19(8):S66.

Cohen Z R, et al. (2015) Localized RNAi therapeutics of chemoresistant grade IV glioma using hyaluronan-grafted lipid-based nanoparticles. *ACS nano* 9(2):1581-1591.

Ramishetti S, et al. (2015) Systemic Gene Silencing in Primary T Lymphocytes Using Targeted Lipid Nanoparticles. *ACS nano* 9(7):6706-6716.

Chang B Y, et al. (2013) Egress of CD19(+)CD5(+) cells into peripheral blood following treatment with the Bruton tyrosine kinase inhibitor ibrutinib in mantle cell lymphoma patients. *Blood* 122(14):2412-2424.

Belliveau N M, et al. (2012) Microfluidic Synthesis of Highly Potent Limit-size Lipid Nanoparticles for In Vivo Delivery of siRNA. *Molecular therapy. Nucleic acids* 1:e37.

Leung A K, Tam Y Y, & Cullis P R (2014) Lipid nanoparticles for short interfering RNA delivery. *Advances in genetics* 88:71-110.

Peer D, Zhu P, Carman C V, Lieberman J, & Shimaoka M (2007) Selective gene silencing in activated leukocytes by targeting siRNAs to the integrin lymphocyte function-associated antigen-1. *Proceedings of the National Academy of Sciences* 104(10):4095-4100.

Yin H, et al. (2014) Non-viral vectors for gene-based therapy. *Nature reviews. Genetics* 15(8):541-555.

Novobrantseva T I, et al. (2012) Systemic RNAi-mediated Gene Silencing in Nonhuman Primate and Rodent Myeloid Cells. *Molecular therapy. Nucleic acids* 1:e4.

Peer D, Park E J, Morishita Y, Carman C V, & Shimaoka M (2008) Systemic Leukocyte-Directed siRNA Delivery Revealing Cyclin D1 as an Anti-Inflammatory Target. *Science* 319(5863):627-630.

Kim S S, et al. (2010) RNAi-mediated CCR5 silencing by LFA-1-targeted nanoparticles prevents HIV infection in BLT mice. *Molecular therapy: the journal of the American Society of Gene Therapy* 18(2):370-376.

Deckert J, et al. (2014) SAR650984, a novel humanized CD38-targeting antibody, demonstrates potent antitumor activity in models of multiple myeloma and other CD38+ hematologic malignancies. *Clinical cancer research: an official journal of the American Association for Cancer Research* 20(17):4574-4583.

Ibrahim S, et al. (2001) CD38 expression as an important prognostic factor in B-cell chronic lymphocytic leukemia. *Blood* 98(1):181-186.

Vaisitti T, et al. (2015) The enzymatic activities of CD38 enhance CLL growth and trafficking: implications for therapeutic targeting. *Leukemia* 29(2):356-368.

Perez-Galan P, et al. (2011) Bortezomib resistance in mantle cell lymphoma is associated with plasmacytic differentiation. *Blood* 117(2):542-552.

Wong S W & Comenzo R L (2015) CD38 Monoclonal Antibody Therapies for Multiple Myeloma. *Clinical lymphoma, myeloma & leukemia* 15(11):635-645.

Phipps C, Chen Y, Gopalakrishnan S, & Tan D (2015) Daratumumab and its potential in the treatment of multiple myeloma: overview of the preclinical and clinical development. *Therapeutic advances in hematology* 6(3): 120-127.

Todisco E, et al. (2000) CD38 ligation inhibits normal and leukemic myelopoiesis. *Blood* 95(2):535-542.

Buschle M, et al. (1990) Transfection and gene expression in normal and malignant primary B lymphocytes. *Journal of immunological methods* 133(1):77-85.

Klier M, et al. (2008) Specific lentiviral shRNA-mediated knockdown of cyclin D1 in mantle cell lymphoma has minimal effects on cell survival and reveals a regulatory circuit with cyclin D2. *Leukemia* 22(11):2097-2105.

Tchakarska G, Le Lan-Leguen A, Roth L, & Sola B (2009) The targeting of the sole cyclin D1 is not adequate for mantle cell lymphoma and myeloma therapies. *Haematologica* 94(12):1781-1782.

Sherr C J & Roberts J M (2004) Living with or without cyclins and cyclin-dependent kinases. *Genes & development* 18(22):2699-2711.

Naresh K N, et al. (2006) Optimal processing of bone marrow trephine biopsy: the Hammersmith Protocol. *Journal of clinicalpathology* 59(9):903-911.

Gust, T. C.; Neubrandt, L.; Merz, C.; Asadullah, K.; Zugel, U.; von Bonin, A. RNA Interference-Mediated Gene Silencing in Murine T cells: In vitro and In vivo Validation of Proinflammatory Target Genes. *Cell Commun. Signaling.* 2008, 6, 3.

Freeley, M.; Long, A. Advances in siRNA Delivery to T-cells: Potential Clinical Applications for Inflammatory Disease, Cancer and Infection. *Biochem. J.* 2013, 455, 133-47.

Goffinet, C.; Keppler, O. T. Efficient Nonviral Gene Delivery into Primary Lymphocytes from Rats and Mice. *FASEB J.* 2006, 20, 500-2.

Peer, D. Induction of Therapeutic Gene Silencing in Leukocyte-implicated Diseases by Targeted and Stabilized Nanoparticles: A Mini-Review. *J. Controlled Release.* 2010, 148, 63-8.

(Perise-Barrios, A. J.; Jimenez, J. L.; Dominguez-Soto, A.; de la Mata, F. J.; Corbi, A. L.; Gomez, R.; Munoz-Fernandez, M. A. Carbosilane Dendrimers as Gene Delivery Agents for The Treatment of HIV Infection. *J. Controlled Release.* 2014, 184, 51-7.

Tezgel, A. O.; Gonzalez-Perez, G.; Telfer, J. C.; Osborne, B. A.; Minter, L. M.; Tew, G. N. Novel Protein Transduction Domain Mimics as Nonviral Delivery Vectors for siRNA Targeting NOTCHI in Primary Human T cells. *Mol. Ther.* 2013, 21, 201-9.

Lee, J.; Yun, K. S.; Choi, C. S.; Shin, S. H.; Ban, H. S.; Rhim, T.; Lee, S. K.; Lee, K. Y. T cell-Specific siRNA Delivery Using Antibody-Conjugated Chitosan Nanoparticles. *Bioconjugate chem.* 2012, 23, 1174-80.

Zhou, J.; Neff, C. P.; Swiderski, P.; Li, H.; Smith, D. D.; Aboellail, T.; Remling-Mulder, L.; Akkina, R.; Rossi, J. J. Functional In vivo Delivery of Multiplexed Anti-HIV-1 siRNAs via A Chemically Synthesized Aptamer with a Sticky Bridge. *Mol. Ther.* 2013, 21, 192-200.

Neff, C. P.; Zhou, J.; Remling, L.; Kuruvilla, J.; Zhang, J.; Li, H.; Smith, D. D.; Swiderski, P.; Rossi, J. J.; Akkina, R. An Aptamer-siRNA Chimera Suppresses HIV-1 Viral Loads and Protects from Helper CD4(+) T cell Decline in Humanized Mice. *Sci. Transl. Med.* 2011, 3, 66ra6.

Gilleron, J.; Querbes, W.; Zeigerer, A.; Borodovsky, A.; Marsico, G.; Schubert, U.; Manygoats, K.; Seifert, S.; Andree, C.; Stoter, M. et al. Image-based Analysis of Lipid Nanoparticle-Mediated siRNA Delivery, Intracellular Trafficking and Endosomal Escape. *Nat. Biotechnol.* 2013, 31, 638-46.

Chen, S.; Tam, Y. Y.; Lin, P. J.; Leung, A. K.; Tam, Y. K.; Cullis, P. R. Development of Lipid Nanoparticle Formulations of siRNA for Hepatocyte Gene Silencing Following Subcutaneous Administration. *J. Controlled Release.* 2014, 196, 106-12.

Song, E.; Lee, S. K.; Wang, J.; Ince, N.; Ouyang, N.; Min, J.; Chen, J.; Shankar, P.; Lieberman, J. RNA interference Targeting Fas Protects Mice from Fulminant Hepatitis. *Nat. Med.* 2003, 9, 347-51.

He, W.; Bennett, M. J.; Luistro, L.; Carvajal, D.; Nevins, T.; Smith, M.; Tyagi, G.; Cai, J.; Wei, X.; Lin, T. A.; et al. Discovery of siRNA Lipid Nanoparticles to Transfect Suspension Leukemia Cells and Provide In vivo Delivery Capability. *Mol. Ther.* 2014, 22, 359-70.

Peer, D.; Karp, J. M.; Hong, S.; Farokhzad, O. C.; Margalit, R.; Langer, R.: Nanocarriers as An Emerging Platform for Cancer Therapy. *Nat. Nanotechnol.* 2007, 2, 751-60.

The invention claimed is:

1. A method for treating a leukocyte associated disease, wherein the leukocyte associated disease is lymphoma, leukemia or multiple myeloma and the leukocyte is selected from a B-cell and a T-cell, comprising the step of administering to a subject in need thereof a pharmaceutical composition comprising a particle for targeted delivery of a nucleic acid to a leukocyte, the particle comprising a lipid membrane comprising a cationic lipid, a membrane stabilizing lipid and a DSPE-PEG maleimide conjugated to a targeting moiety; and a nucleic acid molecule encapsulated within the particle,
wherein the targeting moiety is an antibody selected from the group consisting of an anti-CD38 antibody, an anti-CD4 antibody, an anti-CD8 antibody and an anti-CD3 antibody, or an antigen binding fragment thereof.

2. The method of claim 1, wherein the cationic lipid is selected from: DLinDMA, DLin-MC3-DMA, DLin-KC2-DMA, Di-oleyl-succinyl-serinyl-tobramycin, Di-oleyl-adipyltobramycin, Di-oleyl-suberyl-tobramycin, N,N-dimethyl-N',N'-di[(9Z, 12Z)-octadeca-9,12-dien-1-yl] ethane-1, 2-diamine, Di-oleyl-sebacyl-tobramycin, Di-oleyl-dithioglycolyl-tobramycin, monocationic lipid N-[1-(2,3-Dioleoyloxy)]-N,N,N-trimethylammonium propane (DOTAP), BCAT O-(2R-1,2-di-O-(1'Z, 9'Z-octadecadienyl)-glycerol)-3-N-(bis-2-aminoethyl)-carbamate, BGSC (Bis-guanidinium-spermidine-cholesterol), BGTC (Bis-guanidinium-tren-cholesterol), CDAN (N'-cholesteryl oxycarbony 1-3,7-diazanonane-1,9-diamine), CHDTAEA (Cholesteryl hemidithiodiglycolyl tris(amino(ethyl)amine), DCAT (O-(1,2-di-O-(9'Z-octadecanyl)-glycerol)-3-N-(bis-2-aminoethyl)-carbamate), DC-Chol (3B [N—(N', N'-dimethylaminoethane)-carbamoyl] cholesterol), DLKD (O,O'-Dilauryl N-lysylaspartate), DMKD (O,O'-Dimyristyl Nlysylaspartate), DOG (Diolcylglycerol, DOGS (Dioctadecylamidoglycylspermine), DOGSDSO (1,2-Dioleoyl-sn-glycero-3-succinyl-2-hydroxyethyl disulfide ornithine), DOPC (1,2-Dioleoylsn-glycero-3-phosphocholine), DOPE (1,2-Dioleoyl-sn-glycerol-3-phosphoethanolamine, DOSN (Dioleyl succinyl ethylthioneomycin), DOSP (Dioleyl succinyl paromomycin), DOST (Dioleyl succinyl tobramycin), 1,2-Uiolcoyl-3-trimethyl ammoniopropane, DOTMA (N'[1-(2,3-Dioleyloxy)propyl]-N,N,N-trimethvlammonium chloride), DPPES (Di-palmitoyl phosphatidyl ethanolamidosperminc), DDAB and DODAP, or any combination thereof.

3. The method of claim 1, wherein the membrane stabilizing lipid is selected from the group consisting of cholesterol, phospholipids, cephalins, sphingolipids and glycoglycerolipids.

4. The method of claim 1, wherein the lipid membrane further comprises phosphatidylamine selected from: 1,2-dilauroyl-L-phosphatidyl-ethanolamine (DLPE), 1,2-Dioleoyl-sn-glycero-3-phosphoethanolamine (DOPE) 1,2-Diphytanoyl-sn-glycero-3-phosphoethanolamine (DPhPE) 1,3-Dipalmitoyl-sn-glycero-2-phosphoethanolamine (1,3-DPPE) 10 1-Palmitoyl-3-oleoyl-sn-glycero-2-phosphoethanolamine (1,3-POPE), Biotin-Phosphatidylethanolamine, 1,2-Dimyristoyl-sn-glycero-3-phosphoethanolamine (DMPE), 1,2-Distearoyl-sn-glycero-3-phosphoethanolamine (DSPE), and Dipalmitoylphosphatidylethanolamine (DPPE).

5. The method of claim 1, wherein the particle further comprises an additional PEG derivative, wherein the PEG derivative is selected from: PEG-DMG, PEG-CDMA, 3-N-(-methoxy poly(ethylene glycol)2000)carbamoyl-1,2-dimyristyloxy-propylamine; PEG-cDSA, 3-N-(-methoxy poly(ethylene glycol)2000)carbamoyl-1,2-distearyloxy-propylamine, PEG-Amine, or combinations thereof.

6. The method of claim 1, wherein the lipid membrane comprises a cationic lipid selected from: DLin-MC3-DMA, DLinDMA and DLin-KC2-DMA; cholesterol; DSPC; and PEG-DMG.

7. The method of claim 1, wherein the lymphoma is selected from B-cell lymphoma and T-cell lymphoma.

8. The method of claim 7, wherein the B-cell lymphoma is selected from Hodgkin's lymphoma and non-Hodgkin's lymphoma.

9. The method of claim 7, wherein the B-cell lymphoma is Mantle cell lymphoma (MCL).

10. The method of claim 1, wherein the nucleic acid comprises an interfering RNA selected from the group consisting of siRNA, miRNA, shRNA, and antisense RNA, modified forms thereof, and combinations thereof.

11. The method of claim 10, wherein the nucleic acid molecule is siRNA.

12. The method of claim 11, wherein the siRNA is directed against a cell cycle regulator.

13. The method of claim 12, wherein the cell cycle regulator is selected from the group consisting of: Polo-like Kinase 1 (PLK), Cyclin D1, CHK1, Notch pathway genes, PDGFRA, EGFRVIII, PD-L1, RelB, STAT1, STAT3, MCL1, CKAP5, RRM1, SF3A1 and CDK11B, and a combination thereof.

14. The method of claim 13, wherein the cell cycle regulator is Cyclin D1.

15. The method of claim 1, wherein the administration is systemic.

* * * * *

```
SEQUENCE LISTING

<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: Chemically modified siRNAs sequences

<400> SEQUENCE: 1
cuggcugaau uucagagcad tsdt                                              24

<210> SEQ ID NO 2
<211> LENGTH: 24
<212> TYPE: DNA
<213> ORGANISM: Artificial Sequence
<220> FEATURE:
<223> OTHER INFORMATION: Chemically modified siRNAs sequence

<400> SEQUENCE: 2
ugcucugaaa uucagccagd tsdt                                              24

<210> SEQ ID NO 3
<211> LENGTH: 24
<212> TYPE: DNA
<213> ORGANISM: Artificial Sequence
<220> FEATURE:
<223> OTHER INFORMATION: Chemically modified siRNAs sequence

<400> SEQUENCE: 3
cuuacgcuga guacuucgad tsdt                                              24

<210> SEQ ID NO 4
<211> LENGTH: 24
<212> TYPE: DNA
<213> ORGANISM: Artificial Sequence
<220> FEATURE:
<223> OTHER INFORMATION: Chemically modified siRNAs sequence

<400> SEQUENCE: 4
ucgaaguacu cagcguaagd tsdt                                              24

<210> SEQ ID NO 5
<211> LENGTH: 21
```

```
<212> TYPE: DNA
<213> ORGANISM: Artificial Sequence
<220> FEATURE:
<223> OTHER INFORMATION: Chemically modified siRNAs sequence

<400> SEQUENCE: 5
guaggacucu cauucgggat t                                              21

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ccatcgtgtc atcaaggact tc                                             22

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gatgctcttt cctcctgtgc c                                              21

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tcttacacca tccactctgg gc                                             22

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gcttcgttgt ggtagctatg gtt                                            23

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gaggagcccc aacaacttcc                                                20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
```

```
gtccgggtca cacttgatca c                                              21

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cgcaagcatg ctcagacctt                                                20

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
tgcgatcatc gacggtgg                                                  18

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ctgaccatcg aaaaactgtg cat                                            23

<210> SEQ ID NO 15
<211> LENGTH: 17
<212> TYPE: DNA
<213> ORGANISM: Artificial Sequence
<220> FEATURE:
<223> OTHER INFORMATION: Primer

<400> SEQUENCE: 15
acctcccagt cccgcaa                                                   17

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tccagagagc cagtccatgc                                                20

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
cctgccacaa ttccatgct                                                 19

<210> SEQ ID NO 18
<211> LENGTH: 22
<212> TYPE: DNA
<213> ORGANISM: Artificial Sequence
```

```
<220> FEATURE:
<223> OTHER INFORMATION: Primer

<400> SEQUENCE: 18
accaagagag ttgtccgcag tg                                        22

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
tcatggcatt acggatggtc c                                         21
```